(12) United States Patent
O'Brien

(10) Patent No.: US 6,870,027 B2
(45) Date of Patent: Mar. 22, 2005

(54) METHODS FOR THE EARLY DIAGNOSIS OF OVARIAN CANCER

(76) Inventor: Timothy J. O'Brien, 2610 N. Pierce, Little Rock, AR (US) 72207

(*) Notice: Subject to any disclaimer, the term of this patent is extended or adjusted under 35 U.S.C. 154(b) by 186 days.

(21) Appl. No.: 10/172,597

(22) Filed: Jun. 14, 2002

(65) Prior Publication Data

US 2003/0180736 A1 Sep. 25, 2003

Related U.S. Application Data

(63) Continuation-in-part of application No. 09/835,948, filed on Apr. 16, 2001, now abandoned, which is a division of application No. 09/492,543, filed on Jan. 27, 2000, now Pat. No. 6,316,213, which is a continuation-in-part of application No. 09/039,211, filed on Mar. 14, 1998, now Pat. No. 6,303,318.
(60) Provisional application No. 60/041,404, filed on Mar. 19, 1997.

(51) Int. Cl.⁷ .......................... C07K 7/00; C07K 16/00; C07K 14/00
(52) U.S. Cl. .................. 530/300; 530/350; 530/328; 530/324
(58) Field of Search ................................. 530/300, 324, 530/328, 350

(56) References Cited

PUBLICATIONS

Bowie et al (Science, 1990,247:1306–1310).*
Akizawa et al (Peptide Chemistry, 1995, 33:305–308).*
Harlow and Lane, (Antibodies, A Laboratory Manual, 1988, Cold Spring Harbor Laboratory, New York, pp. 96–97).*

* cited by examiner

*Primary Examiner*—Susan Ungar
(74) *Attorney, Agent, or Firm*—Benjamin Aaron Adler

(57) ABSTRACT

The disclosed nucleic acid primer sets, used in combination with quantitative amplification (PCR) of tissue cDNA, can indicate the presence of specific proteases in a tissue sample. Specifically, the present invention relates to expression of PUMP-1 protease (matrix metalloprotease 7). The detected proteases are themselves specifically over-expressed in certain cancers, and their presence may serve for early detection of associated ovarian and other malignancies, and for the design of interactive therapies for cancer treatment.

2 Claims, 24 Drawing Sheets

1) Normal Ovary 2) Tumor
3) Normal Ovary 4) Tumor

1.    ↓    .15

VVTAAHCVYDLYLPK

16    .30

SWTIQVGLVSLLDNP    ↓ indicates the site of insert in TADG12

31    .45    H & D are the conserved regions of Serine protease.

APSHLVEKIVYHSKY 46    57

KPKRLGNDIALL (SEQ ID NO. 190)

```
   1   6    10                    53   57
___H CVY D LYL (SEQ ID NO.191)___D_____.
      *          ⇑                 *
``` site of 133 bp insert in TADG12

Fig. 15

SEQUENCE LISTING

```
<160> NUMBER OF SEQ ID NOS: 191

<210> SEQ ID NO 1
<211> LENGTH: 23
<212> TYPE: DNA
<213> ORGANISM: Artificial sequence
<220> FEATURE:
<221> NAME/KEY: primer_bind
<222> LOCATION: 6, 9, 12, 15, 18
<223> OTHER INFORMATION: sense oligonucleotide primer for amplifying
      serine proteases, n = Inosine

<400> SEQUENCE: 1
tgggtngtna cngcngcnca ytg                                          23

<210> SEQ ID NO 2
<211> LENGTH: 20
<212> TYPE: DNA
<213> ORGANISM: Artificial sequence
<220> FEATURE:
```

-continued

```
<221> NAME/KEY: primer_bind
<222> LOCATION: 3, 6, 9, 12, 15, 18
<223> OTHER INFORMATION: antisense oligonucleotide primer for amplifying
      serine proteases, n = Inosine

<400> SEQUENCE: 2
arnarngcna tntcnttncc                                                    20

<210> SEQ ID NO 3
<211> LENGTH: 20
<212> TYPE: DNA
<213> ORGANISM: Artificial sequence
<220> FEATURE:
<221> NAME/KEY: primer_bind
<222> LOCATION: 3, 6, 9, 12, 18
<223> OTHER INFORMATION: antisense oligonucleotide primer for amplifying
      serine proteases, n = Inosine

<400> SEQUENCE: 3
arnggnccnc cnswrtcncc                                                    20

<210> SEQ ID NO 4
<211> LENGTH: 24
<212> TYPE: DNA
<213> ORGANISM: Artificial sequence
<220> FEATURE:
<221> NAME/KEY: primer_bind
<222> LOCATION: 6, 15, 18
<223> OTHER INFORMATION: sense oligonucleotide primer for amplifying
      cysteine proteases, n = Inosine

<400> SEQUENCE: 4
carggncart gyggnwsntg ytgg                                               24

<210> SEQ ID NO 5
<211> LENGTH: 20
<212> TYPE: DNA
<213> ORGANISM: Artificial sequence
<220> FEATURE:
<221> NAME/KEY: primer_bind
<222> LOCATION: 3, 6, 15
<223> OTHER INFORMATION: antisense oligonucleotide primer for amplifying
      cysteine proteases, n = Inosine

<400> SEQUENCE: 5
tanccnccrt trcanccytc                                                    20

<210> SEQ ID NO 6
<211> LENGTH: 20
<212> TYPE: DNA
<213> ORGANISM: Artificial sequence
<220> FEATURE:
<221> NAME/KEY: primer_bind
<222> LOCATION: 3, 6, 12, 15, 18
<223> OTHER INFORMATION: sense oligonucleotide primer for amplifying
      metallo-proteases, n = Inosine

<400> SEQUENCE: 6
ccnmgntgyg gnrwnccnga                                                    20

<210> SEQ ID NO 7
<211> LENGTH: 17
<212> TYPE: DNA
<213> ORGANISM: Artificial sequence
<220> FEATURE:
<221> NAME/KEY: primer_bind
<222> LOCATION: 6, 9, 11
<223> OTHER INFORMATION: antisense oligonucleotide primer for amplifying
      metallo-proteases, n = Inosine
```

<400> SEQUENCE: 7
ttrtgnccna nytcrtg                                                17

<210> SEQ ID NO 8
<211> LENGTH: 20
<212> TYPE: DNA
<213> ORGANISM: Artificial sequence
<220> FEATURE:
<223> OTHER INFORMATION: sense oligonucleotide primer specific for
      hepsin

<400> SEQUENCE: 8
tgtcccgatg gcgagtgttt                                             20

<210> SEQ ID NO 9
<211> LENGTH: 20
<212> TYPE: DNA
<213> ORGANISM: Artificial sequence
<220> FEATURE:
<223> OTHER INFORMATION: antisense oligonucleotide primer specific for
      hepsin

<400> SEQUENCE: 9
cctgttggcc atagtactgc                                             20

<210> SEQ ID NO 10
<211> LENGTH: 20
<212> TYPE: DNA
<213> ORGANISM: Artificial sequence
<220> FEATURE:
<223> OTHER INFORMATION: sense oligonucleotide primer specific for SCCE

<400> SEQUENCE: 10
agatgaatga gtacaccgtg                                             20

<210> SEQ ID NO 11
<211> LENGTH: 20
<212> TYPE: DNA
<213> ORGANISM: Artificial sequence
<220> FEATURE:
<223> OTHER INFORMATION: antisense oligonucleotide primer specific for
      SCCE

<400> SEQUENCE: 11
ccagtaagtc cttgtaaacc                                             20

<210> SEQ ID NO 12
<211> LENGTH: 20
<212> TYPE: DNA
<213> ORGANISM: Artificial sequence
<220> FEATURE:
<223> OTHER INFORMATION: sense oligonucleotide primer specific for CompB

<400> SEQUENCE: 12
aagggacacg agagctgtat                                             20

<210> SEQ ID NO 13
<211> LENGTH: 20
<212> TYPE: DNA
<213> ORGANISM: Artificial sequence
<220> FEATURE:
<223> OTHER INFORMATION: antisense oligonucleotide primer specific for
      CompB

<400> SEQUENCE: 13

-continued aagtggtagt tggaggaagc                                         20

<210> SEQ ID NO 14
<211> LENGTH: 20
<212> TYPE: DNA
<213> ORGANISM: Artificial sequence
<220> FEATURE:
<223> OTHER INFORMATION: sense oligonucleotide primer specific for
      Cath-L

<400> SEQUENCE: 14
attggagaga gaaaggctac                                         20

<210> SEQ ID NO 15
<211> LENGTH: 20
<212> TYPE: DNA
<213> ORGANISM: Artificial sequence
<220> FEATURE:
<223> OTHER INFORMATION: antisense oligonucleotide primer specific for
      Cath-L

<400> SEQUENCE: 15
cttgggattg tacttacagg                                         20

<210> SEQ ID NO 16
<211> LENGTH: 20
<212> TYPE: DNA
<213> ORGANISM: Artificial sequence
<220> FEATURE:
<223> OTHER INFORMATION: sense oligonucleotide primer specific for
      PUMP-1

<400> SEQUENCE: 16
cttccaaagt ggtcacctac                                         20

<210> SEQ ID NO 17
<211> LENGTH: 20
<212> TYPE: DNA
<213> ORGANISM: Artificial sequence
<220> FEATURE:
<223> OTHER INFORMATION: antisense oligonucleotide primer specific for
      PUMP-1

<400> SEQUENCE: 17
ctagactgct accatccgtc                                         20

<210> SEQ ID NO 18
<211> LENGTH: 17
<212> TYPE: DNA
<213> ORGANISM: Artificial sequence
<220> FEATURE:
<223> OTHER INFORMATION: sense oligonucleotide primer specific for
      (-tubulin

<400> SEQUENCE: 18
tgcattgaca acgaggc                                            17

<210> SEQ ID NO 19
<211> LENGTH: 17
<212> TYPE: DNA
<213> ORGANISM: Artificial sequence
<220> FEATURE:
<223> OTHER INFORMATION: antisense oligonucleotide primer specific for
      (-tubulin

<400> SEQUENCE: 19
ctgtcttgac attgttg                                            17

```
<210> SEQ ID NO 20
<211> LENGTH: 20
<212> TYPE: DNA
<213> ORGANISM: Artificial sequence
<220> FEATURE:
<223> OTHER INFORMATION: sense oligonucleotide primer specific for
      Protease M

<400> SEQUENCE: 20
ctgtgatcca ccctgactat                                                    20

<210> SEQ ID NO 21
<211> LENGTH: 20
<212> TYPE: DNA
<213> ORGANISM: Artificial sequence
<220> FEATURE:
<223> OTHER INFORMATION: antisense oligonucleotide primer specific for
      Protease M

<400> SEQUENCE: 21
caggtggatg tatgcacact                                                    20

<210> SEQ ID NO 22
<211> LENGTH: 20
<212> TYPE: DNA
<213> ORGANISM: Artificial sequence
<220> FEATURE:
<223> OTHER INFORMATION: sense oligonucleotide primer specific for
      TADG-12

<400> SEQUENCE: 22
gcgcactgtg tttatgagat                                                    20

<210> SEQ ID NO 23
<211> LENGTH: 20
<212> TYPE: DNA
<213> ORGANISM: Artificial sequence
<220> FEATURE:
<223> OTHER INFORMATION: antisense oligonucleotide primer specific for
      TADG-12

<400> SEQUENCE: 23
ctctttggct tgtacttgct                                                    20

<210> SEQ ID NO 24
<211> LENGTH: 20
<212> TYPE: DNA
<213> ORGANISM: Artificial sequence
<220> FEATURE:
<223> OTHER INFORMATION: sense oligonucleotide primer specific for
      TADG-13

<400> SEQUENCE: 24
tgagggacat cattatgcac                                                    20

<210> SEQ ID NO 25
<211> LENGTH: 20
<212> TYPE: DNA
<213> ORGANISM: Artificial sequence
<220> FEATURE:
<223> OTHER INFORMATION: antisense oligonucleotide primer specific for
      TADG-13

<400> SEQUENCE: 25
caagttttcc ccataattgg                                                    20
```

```
<210> SEQ ID NO 26
<211> LENGTH: 20
<212> TYPE: DNA
<213> ORGANISM: Artificial sequence
<220> FEATURE:
<223> OTHER INFORMATION: sense oligonucleotide primer specific for
      TADG-14

<400> SEQUENCE: 26
acagtacgcc tgggagacca                                               20

<210> SEQ ID NO 27
<211> LENGTH: 20
<212> TYPE: DNA
<213> ORGANISM: Artificial sequence
<220> FEATURE:
<223> OTHER INFORMATION: antisense oligonucleotide primer specific for
      TADG-14

<400> SEQUENCE: 27
ctgagacggt gcaattctgg                                               20

<210> SEQ ID NO 28
<211> LENGTH: 1078
<212> TYPE: RNA
<213> ORGANISM: Artificial sequence
<220> FEATURE:
<223> OTHER INFORMATION: antisense RNA of PUMP-1

<400> SEQUENCE: 28
uauuugugua uguaacauuu auugacaucu acgcgcacug acaaagcuca              50
uagauggaau aagacacagu cacaccauaa aggaguuuaa ccaauaaaag              100
gagugaaaga cauucaaaaa ccaacugcaa uaaaaagggg ugacauaauu              150
gcuaaaugga guggaggaac agugcuuauc aauucugauu gugcaacaau              200
gauauacaau ccaaugaaug aaugaaugga uuucugccu gaaguuucua               250 uuucuuucuu gaauuacuuc ucuuuccaua uaguuucuga augccuuuaa               300
uaucauccug ggaaaguuua aaauuuuggg gaucuccauu uccauagguu              350
ggauacauca cugcauuagg aucagaggaa ugucccauac ccaaagaaug              400
gccaaguuca ugaguugcag cauacaggaa guuaaucccu agacugcuac              450
cauccgucca gcguucaucc ucaucgaagu gagcaucucc uccgagaccu              500
gucccaggcg caaaggcaug agccagcgug uuuccuggcc caucaaaugg              550
guaggagucc ccaugagcuc cucgcgcaaa gccaaucaug augucagcag              600
uuccccauac aacuuccug aaaugcaggg ggaucucuuu gccccacaug                650
uuuaaagccu uugacacuaa ucgauccacu guaauaugcg guaagucucg              700
aguauaugau acgauccugu aggugaccac uuuggaaguc cauuuugggc              750
uauuuggaaa uagugaguau ucugcaacau cuggcacucc acaucugggc              800
uucugcauua uuucuaugac gcgggaguuu aacauuccag uuauaggua g             850 gccaaagaau uuuugcaucu ccuugaguuu ggcuucuaaa cuguuggcau              900 uuuuguuuc ugaucauag agauaaaauc ucuugagaua guccgagcc                 950 uguucccacu guagcucacu caugccuccc gccuccugag gcagcggcag              1000
ggccaggcug ccaggcagca ggcacacagc acacagcacg gugagucgca              1050
uagcugccgu ccagagacaa uuguucuu                                      1078
```

<210> SEQ ID NO 29
<211> LENGTH: 1078
<212> TYPE: DNA
<213> ORGANISM: Homo sapiens
<220> FEATURE:
<223> OTHER INFORMATION: cDNA of PUMP-1

<400> SEQUENCE: 29

```
aagaacaatt gtctctggac ggcagctatg cgactcaccg tgctgtgtgc        50
tgtgtgcctg ctgcctggca gcctggccct gccgctgcct caggaggcgg       100
gaggcatgag tgagctacag tgggaacagg ctcaggacta tctcaagaga       150
ttttatctct atgactcaga aacaaaaaat gccaacagtt tagaagccaa       200
actcaaggag atgcaaaaat tctttggcct acctataact ggaatgttaa       250
actcccgcgt catagaaata atgcagaagc ccagatgtgg agtgccagat       300
gttgcagaat actcactatt tccaaatagc ccaaaatgga cttccaaagt       350
ggtcacctac aggatcgtat catatactcg agacttaccg catattcagg       400
tggatcgatt agtgtcaaag gctttaaaca tgtggggcaa agagatcccc       450
ctgcatttca ggaaagttgt atggggaact gctgacatca tgattggctt       500
tgcgcgagga gctcatgggg actcctaccc atttgatggg ccaggaaaca       550
cgctggctca tgcctttgcg cctgggacag gtctcggagg agatgctcac       600
ttcgatgagg atgaacgctg gacggatggt agcagtctag ggattaactt       650
cctgtatgct gcaactcatg aacttggcca ttctttgggt atgggacatt       700
cctctgatcc taatgcagtg atgtatccaa cctatggaaa tggagatccc       750
caaaattta acttcccca ggatgatatt aaaggcattc agaaactata       800
tggaaagaga agtaattcaa gaaagaaata gaaacttcag gcagaacatc       850
cattcattca ttcattggat tgtatatcat tgttgcacaa tcagaattga       900
taagcactgt tcctccactc catttagcaa ttatgtcacc cttttttatt       950
gcagttggtt tttgaatgtc tttcactcct tttattggtt aaactccttt      1000
atggtgtgac tgtgtcttat tccatctatg agctttgtca gtgcgcgtag      1050
atgtcaataa atgttacata cacaaata                              1078
```

<210> SEQ ID NO 30
<211> LENGTH: 9
<212> TYPE: PRT
<213> ORGANISM: Homo sapiens
<220> FEATURE:
<223> OTHER INFORMATION: Residues 208-216 of the PUMP-1 protein

<400> SEQUENCE: 30

Phe Leu Tyr Ala Ala Thr His Glu Leu
                5

<210> SEQ ID NO 31
<211> LENGTH: 9
<212> TYPE: PRT
<213> ORGANISM: Homo sapiens
<220> FEATURE:
<223> OTHER INFORMATION: Residues 134-142 of the PUMP-1 protein

<400> SEQUENCE: 31

Asn Met Trp Gly Lys Glu Ile Pro Leu

```
<210> SEQ ID NO 32
<211> LENGTH: 9
<212> TYPE: PRT
<213> ORGANISM: Homo sapiens
<220> FEATURE:
<223> OTHER INFORMATION: Residues 81-89 of the PUMP-1 protein

<400> SEQUENCE: 32

Ile Met Gln Lys Pro Arg Cys Gly Val
                5

<210> SEQ ID NO 33
<211> LENGTH: 9
<212> TYPE: PRT
<213> ORGANISM: Homo sapiens
<220> FEATURE:
<223> OTHER INFORMATION: Residues 10-18 of the PUMP-1 protein

<400> SEQUENCE: 33

Cys Leu Leu Pro Gly Ser Leu Ala Leu
                5

<210> SEQ ID NO 34
<211> LENGTH: 9
<212> TYPE: PRT
<213> ORGANISM: Homo sapiens
<220> FEATURE:
<223> OTHER INFORMATION: Residues 60-68 of the PUMP-1 protein

<400> SEQUENCE: 34

Lys Glu Met Gln Lys Phe Phe Gly Leu
                5

<210> SEQ ID NO 35
<211> LENGTH: 9
<212> TYPE: PRT
<213> ORGANISM: Homo sapiens
<220> FEATURE:
<223> OTHER INFORMATION: Residues 203-211 of the PUMP-1 protein

<400> SEQUENCE: 35

Ser Leu Gly Ile Asn Phe Leu Tyr Ala
                5

<210> SEQ ID NO 36
<211> LENGTH: 9
<212> TYPE: PRT
<213> ORGANISM: Homo sapiens
<220> FEATURE:
<223> OTHER INFORMATION: Residues 73-81 of the PUMP-1 protein

<400> SEQUENCE: 36

Met Leu Asn Ser Arg Val Ile Glu Ile
                5

<210> SEQ ID NO 37
<211> LENGTH: 9
<212> TYPE: PRT
<213> ORGANISM: Homo sapiens
<220> FEATURE:
<223> OTHER INFORMATION: Residues 4-12 of the PUMP-1 protein

<400> SEQUENCE: 37

Thr Val Leu Cys Ala Val Cys Leu Leu
                5
```

<210> SEQ ID NO 38
<211> LENGTH: 9
<212> TYPE: PRT
<213> ORGANISM: Homo sapiens
<220> FEATURE:
<223> OTHER INFORMATION: Residues 132-140 of the PUMP-1 protein

<400> SEQUENCE: 38

Ala Leu Asn Met Trp Gly Lys Glu Ile
                 5

<210> SEQ ID NO 39
<211> LENGTH: 9
<212> TYPE: PRT
<213> ORGANISM: Homo sapiens
<220> FEATURE:
<223> OTHER INFORMATION: Residues 109-117 of the PUMP-1 protein

<400> SEQUENCE: 39

Val Thr Tyr Arg Ile Val Ser Tyr Thr
                 5

<210> SEQ ID NO 40
<211> LENGTH: 9
<212> TYPE: PRT
<213> ORGANISM: Homo sapiens
<220> FEATURE:
<223> OTHER INFORMATION: Residues 127-135 of the PUMP-1 protein

<400> SEQUENCE: 40

Arg Leu Val Ser Lys Ala Leu Asn Met
                 5

<210> SEQ ID NO 41
<211> LENGTH: 9
<212> TYPE: PRT
<213> ORGANISM: Homo sapiens
<220> FEATURE:
<223> OTHER INFORMATION: Residues 154-162 of the PUMP-1 protein

<400> SEQUENCE: 41

Ile Met Ile Gly Phe Ala Arg Gly Ala
                 5

<210> SEQ ID NO 42
<211> LENGTH: 9
<212> TYPE: PRT
<213> ORGANISM: Homo sapiens
<220> FEATURE:
<223> OTHER INFORMATION: Residues 43-51 of the PUMP-1 protein

<400> SEQUENCE: 42

Tyr Leu Tyr Asp Ser Glu Thr Lys Asn
                 5

<210> SEQ ID NO 43
<211> LENGTH: 9
<212> TYPE: PRT
<213> ORGANISM: Homo sapiens
<220> FEATURE:
<223> OTHER INFORMATION: Residues 140-148 of the PUMP-1 protein

<400> SEQUENCE: 43

Ile Pro Leu His Phe Arg Lys Val Val
                 5

```
<210> SEQ ID NO 44
<211> LENGTH: 9
<212> TYPE: PRT
<213> ORGANISM: Homo sapiens
<220> FEATURE:
<223> OTHER INFORMATION: Residues 146-154 of the PUMP-1 protein

<400> SEQUENCE: 44

Lys Val Val Trp Gly Thr Ala Asp Ile
                5

<210> SEQ ID NO 45
<211> LENGTH: 9
<212> TYPE: PRT
<213> ORGANISM: Homo sapiens
<220> FEATURE:
<223> OTHER INFORMATION: Residues 36-44 of the PUMP-1 protein

<400> SEQUENCE: 45

Gln Asp Tyr Leu Lys Arg Phe Tyr Leu
                5

<210> SEQ ID NO 46
<211> LENGTH: 9
<212> TYPE: PRT
<213> ORGANISM: Homo sapiens
<220> FEATURE:
<223> OTHER INFORMATION: Residues 2-10 of the PUMP-1 protein

<400> SEQUENCE: 46

Arg Leu Thr Val Leu Cys Ala Val Cys
                5

<210> SEQ ID NO 47
<211> LENGTH: 9
<212> TYPE: PRT
<213> ORGANISM: Homo sapiens
<220> FEATURE:
<223> OTHER INFORMATION: Residues 201-209 of the PUMP-1 protein

<400> SEQUENCE: 47

Gly Ser Ser Leu Gly Ile Asn Phe Leu
                5

<210> SEQ ID NO 48
<211> LENGTH: 9
<212> TYPE: PRT
<213> ORGANISM: Homo sapiens
<220> FEATURE:
<223> OTHER INFORMATION: Residues 70-78 of the PUMP-1 protein

<400> SEQUENCE: 48

Ile Thr Gly Met Leu Asn Ser Arg Val
                5

<210> SEQ ID NO 49
<211> LENGTH: 9
<212> TYPE: PRT
<213> ORGANISM: Homo sapiens
<220> FEATURE:
<223> OTHER INFORMATION: Residues 205-213 of the PUMP-1 protein

<400> SEQUENCE: 49

Gly Ile Asn Phe Leu Tyr Ala Ala Thr
                5
```

```
<210> SEQ ID NO 50
<211> LENGTH: 9
<212> TYPE: PRT
<213> ORGANISM: Homo sapiens
<220> FEATURE:
<223> OTHER INFORMATION: Residues 4-12 of the PUMP-1 protein

<400> SEQUENCE: 50

Thr Val Leu Cys Ala Val Cys Leu Leu
                5

<210> SEQ ID NO 51
<211> LENGTH: 9
<212> TYPE: PRT
<213> ORGANISM: Homo sapiens
<220> FEATURE:
<223> OTHER INFORMATION: Residues 208-216 of the PUMP-1 protein

<400> SEQUENCE: 51

Phe Leu Tyr Ala Ala Thr His Glu Leu
                5

<210> SEQ ID NO 52
<211> LENGTH: 9
<212> TYPE: PRT
<213> ORGANISM: Homo sapiens
<220> FEATURE:
<223> OTHER INFORMATION: Residues 60-68 of the PUMP-1 protein

<400> SEQUENCE: 52

Lys Glu Met Gln Lys Phe Phe Gly Leu
                5

<210> SEQ ID NO 53
<211> LENGTH: 9
<212> TYPE: PRT
<213> ORGANISM: Homo sapiens
<220> FEATURE:
<223> OTHER INFORMATION: Residues 10-18 of the PUMP-1 protein

<400> SEQUENCE: 53

Cys Leu Leu Pro Gly Ser Leu Ala Leu
                5

<210> SEQ ID NO 54
<211> LENGTH: 9
<212> TYPE: PRT
<213> ORGANISM: Homo sapiens
<220> FEATURE:
<223> OTHER INFORMATION: Residues 134-142 of the PUMP-1 protein

<400> SEQUENCE: 54

Asn Met Trp Gly Lys Glu Ile Pro Leu
                5

<210> SEQ ID NO 55
<211> LENGTH: 9
<212> TYPE: PRT
<213> ORGANISM: Homo sapiens
<220> FEATURE:
<223> OTHER INFORMATION: Residues 8-16 of the PUMP-1 protein

<400> SEQUENCE: 55

Ala Val Cys Leu Leu Pro Gly Ser Leu
                5

<210> SEQ ID NO 56
```

```
<211> LENGTH: 9
<212> TYPE: PRT
<213> ORGANISM: Homo sapiens
<220> FEATURE:
<223> OTHER INFORMATION: Residues 146-154 of the PUMP-1 protein

<400> SEQUENCE: 56

Lys Val Val Trp Gly Thr Ala Asp Ile
                5

<210> SEQ ID NO 57
<211> LENGTH: 9
<212> TYPE: PRT
<213> ORGANISM: Homo sapiens
<220> FEATURE:
<223> OTHER INFORMATION: Residues 73-81 of the PUMP-1 protein

<400> SEQUENCE: 57

Met Leu Asn Ser Arg Val Ile Glu Ile
                5

<210> SEQ ID NO 58
<211> LENGTH: 9
<212> TYPE: PRT
<213> ORGANISM: Homo sapiens
<220> FEATURE:
<223> OTHER INFORMATION: Residues 81-89 of the PUMP-1 protein

<400> SEQUENCE: 58

Ile Met Gln Lys Pro Arg Cys Gly Val
                5

<210> SEQ ID NO 59
<211> LENGTH: 9
<212> TYPE: PRT
<213> ORGANISM: Homo sapiens
<220> FEATURE:
<223> OTHER INFORMATION: Residues 66-74 of the PUMP-1 protein

<400> SEQUENCE: 59

Phe Gly Leu Pro Ile Thr Gly Met Leu
                5

<210> SEQ ID NO 60
<211> LENGTH: 9
<212> TYPE: PRT
<213> ORGANISM: Homo sapiens
<220> FEATURE:
<223> OTHER INFORMATION: Residues 147-155 of the PUMP-1 protein

<400> SEQUENCE: 60

Val Val Trp Gly Thr Ala Asp Ile Met
                5

<210> SEQ ID NO 61
<211> LENGTH: 9
<212> TYPE: PRT
<213> ORGANISM: Homo sapiens
<220> FEATURE:
<223> OTHER INFORMATION: Residues 212-220 of the PUMP-1 protein

<400> SEQUENCE: 61

Ala Thr His Glu Leu Gly His Ser Leu
                5

<210> SEQ ID NO 62
<211> LENGTH: 9
```

```
<212> TYPE: PRT
<213> ORGANISM: Homo sapiens
<220> FEATURE:
<223> OTHER INFORMATION: Residues 178-186 of the PUMP-1 protein

<400> SEQUENCE: 62

His Ala Phe Ala Pro Gly Thr Gly Leu
                5

<210> SEQ ID NO 63
<211> LENGTH: 9
<212> TYPE: PRT
<213> ORGANISM: Homo sapiens
<220> FEATURE:
<223> OTHER INFORMATION: Residues 205-213 of the PUMP-1 protein

<400> SEQUENCE: 63

Gly Ile Asn Phe Leu Tyr Ala Ala Thr
                5

<210> SEQ ID NO 64
<211> LENGTH: 9
<212> TYPE: PRT
<213> ORGANISM: Homo sapiens
<220> FEATURE:
<223> OTHER INFORMATION: Residues 22-30 of the PUMP-1 protein

<400> SEQUENCE: 64

Gln Glu Ala Gly Gly Met Ser Glu Leu
                5

<210> SEQ ID NO 65
<211> LENGTH: 9
<212> TYPE: PRT
<213> ORGANISM: Homo sapiens
<220> FEATURE:
<223> OTHER INFORMATION: Residues 112-120 of the PUMP-1 protein

<400> SEQUENCE: 65

Arg Ile Val Ser Tyr Thr Arg Asp Leu
                5

<210> SEQ ID NO 66
<211> LENGTH: 9
<212> TYPE: PRT
<213> ORGANISM: Homo sapiens
<220> FEATURE:
<223> OTHER INFORMATION: Residues 167-175 of the PUMP-1 protein

<400> SEQUENCE: 66

Tyr Pro Phe Asp Gly Pro Gly Asn Thr
                5

<210> SEQ ID NO 67
<211> LENGTH: 9
<212> TYPE: PRT
<213> ORGANISM: Homo sapiens
<220> FEATURE:
<223> OTHER INFORMATION: Residues 3-11 of the PUMP-1 protein

<400> SEQUENCE: 67

Leu Thr Val Leu Cys Ala Val Cys Leu
                5

<210> SEQ ID NO 68
<211> LENGTH: 9
<212> TYPE: PRT
```

```
<213> ORGANISM: Homo sapiens
<220> FEATURE:
<223> OTHER INFORMATION: Residues 140-148 of the PUMP-1 protein

<400> SEQUENCE: 68

Ile Pro Leu His Phe Arg Lys Val Val
                5

<210> SEQ ID NO 69
<211> LENGTH: 9
<212> TYPE: PRT
<213> ORGANISM: Homo sapiens
<220> FEATURE:
<223> OTHER INFORMATION: Residues 109-117 of the PUMP-1 protein

<400> SEQUENCE: 69

Val Thr Tyr Arg Ile Val Ser Tyr Thr
                5

<210> SEQ ID NO 70
<211> LENGTH: 9
<212> TYPE: PRT
<213> ORGANISM: Homo sapiens
<220> FEATURE:
<223> OTHER INFORMATION: Residues 225-233 of the PUMP-1 protein

<400> SEQUENCE: 70

Ser Ser Asp Pro Asn Ala Val Met Tyr
                5

<210> SEQ ID NO 71
<211> LENGTH: 9
<212> TYPE: PRT
<213> ORGANISM: Homo sapiens
<220> FEATURE:
<223> OTHER INFORMATION: Residues 78-86 of the PUMP-1 protein

<400> SEQUENCE: 71

Val Ile Glu Ile Met Gln Lys Pro Arg
                5

<210> SEQ ID NO 72
<211> LENGTH: 9
<212> TYPE: PRT
<213> ORGANISM: Homo sapiens
<220> FEATURE:
<223> OTHER INFORMATION: Residues 198-206 of the PUMP-1 protein

<400> SEQUENCE: 72

Trp Thr Asp Gly Ser Ser Leu Gly Ile
                5

<210> SEQ ID NO 73
<211> LENGTH: 9
<212> TYPE: PRT
<213> ORGANISM: Homo sapiens
<220> FEATURE:
<223> OTHER INFORMATION: Residues 238-246 of the PUMP-1 protein

<400> SEQUENCE: 73

Asn Gly Asp Pro Gln Asn Phe Lys Leu
                5

<210> SEQ ID NO 74
<211> LENGTH: 9
<212> TYPE: PRT
<213> ORGANISM: Homo sapiens
```

```
<220> FEATURE:
<223> OTHER INFORMATION: Residues 92-100 of the PUMP-1 protein

<400> SEQUENCE: 74

Val Ala Glu Tyr Ser Leu Phe Pro Asn
                5

<210> SEQ ID NO 75
<211> LENGTH: 9
<212> TYPE: PRT
<213> ORGANISM: Homo sapiens
<220> FEATURE:
<223> OTHER INFORMATION: Residues 35-43 of the PUMP-1 protein

<400> SEQUENCE: 75

Ala Gln Asp Tyr Leu Lys Arg Phe Tyr
                5

<210> SEQ ID NO 76
<211> LENGTH: 9
<212> TYPE: PRT
<213> ORGANISM: Homo sapiens
<220> FEATURE:
<223> OTHER INFORMATION: Residues 202-210 of the PUMP-1 protein

<400> SEQUENCE: 76

Ser Ser Leu Gly Ile Asn Phe Leu Tyr
                5

<210> SEQ ID NO 77
<211> LENGTH: 9
<212> TYPE: PRT
<213> ORGANISM: Homo sapiens
<220> FEATURE:
<223> OTHER INFORMATION: Residues 46-54 of the PUMP-1 protein

<400> SEQUENCE: 77

Asp Ser Glu Thr Lys Asn Ala Asn Ser
                5

<210> SEQ ID NO 78
<211> LENGTH: 9
<212> TYPE: PRT
<213> ORGANISM: Homo sapiens
<220> FEATURE:
<223> OTHER INFORMATION: Residues 87-95 of the PUMP-1 protein

<400> SEQUENCE: 78

Cys Gly Val Pro Asp Val Ala Glu Tyr
                5

<210> SEQ ID NO 79
<211> LENGTH: 9
<212> TYPE: PRT
<213> ORGANISM: Homo sapiens
<220> FEATURE:
<223> OTHER INFORMATION: Residues 248-256 of the PUMP-1 protein

<400> SEQUENCE: 79

Gln Asp Asp Ile Lys Gly Ile Gln Lys
                5

<210> SEQ ID NO 80
<211> LENGTH: 9
<212> TYPE: PRT
<213> ORGANISM: Homo sapiens
<220> FEATURE:
```

-continued

```
<223> OTHER INFORMATION: Residues 27-35 of the PUMP-1 protein

<400> SEQUENCE: 80

Met Ser Glu Leu Gln Trp Glu Gln Ala
                5

<210> SEQ ID NO 81
<211> LENGTH: 9
<212> TYPE: PRT
<213> ORGANISM: Homo sapiens
<220> FEATURE:
<223> OTHER INFORMATION: Residues 150-158 of the PUMP-1 protein

<400> SEQUENCE: 81

Gly Thr Ala Asp Ile Met Ile Gly Phe
                5

<210> SEQ ID NO 82
<211> LENGTH: 9
<212> TYPE: PRT
<213> ORGANISM: Homo sapiens
<220> FEATURE:
<223> OTHER INFORMATION: Residues 123-131 of the PUMP-1 protein

<400> SEQUENCE: 82

Ile Thr Val Asp Arg Leu Val Ser Lys
                5

<210> SEQ ID NO 83
<211> LENGTH: 9
<212> TYPE: PRT
<213> ORGANISM: Homo sapiens
<220> FEATURE:
<223> OTHER INFORMATION: Residues 108-116 of the PUMP-1 protein

<400> SEQUENCE: 83

Val Val Thr Tyr Arg Ile Val Ser Tyr
                5

<210> SEQ ID NO 84
<211> LENGTH: 9
<212> TYPE: PRT
<213> ORGANISM: Homo sapiens
<220> FEATURE:
<223> OTHER INFORMATION: Residues 54-62 of the PUMP-1 protein

<400> SEQUENCE: 84

Ser Leu Glu Ala Lys Leu Lys Glu Met
                5

<210> SEQ ID NO 85
<211> LENGTH: 9
<212> TYPE: PRT
<213> ORGANISM: Homo sapiens
<220> FEATURE:
<223> OTHER INFORMATION: Residues 163-171 of the PUMP-1 protein

<400> SEQUENCE: 85

His Gly Asp Ser Tyr Pro Phe Asp Gly
                5

<210> SEQ ID NO 86
<211> LENGTH: 9
<212> TYPE: PRT
<213> ORGANISM: Homo sapiens
<220> FEATURE:
<223> OTHER INFORMATION: Residues 10-18 of the PUMP-1 protein
```

```
<400> SEQUENCE: 86

Cys Leu Leu Pro Gly Ser Leu Ala Leu
                5

<210> SEQ ID NO 87
<211> LENGTH: 9
<212> TYPE: PRT
<213> ORGANISM: Homo sapiens
<220> FEATURE:
<223> OTHER INFORMATION: Residues 151-159 of the PUMP-1 protein

<400> SEQUENCE: 87

Thr Ala Asp Ile Met Ile Gly Phe Ala
                5

<210> SEQ ID NO 88
<211> LENGTH: 9
<212> TYPE: PRT
<213> ORGANISM: Homo sapiens
<220> FEATURE:
<223> OTHER INFORMATION: Residues 138-146 of the PUMP-1 protein

<400> SEQUENCE: 88

Lys Glu Ile Pro Leu His Phe Arg Lys
                5

<210> SEQ ID NO 89
<211> LENGTH: 9
<212> TYPE: PRT
<213> ORGANISM: Homo sapiens
<220> FEATURE:
<223> OTHER INFORMATION: Residues 137-145 of the PUMP-1 protein

<400> SEQUENCE: 89

Gly Lys Glu Ile Pro Leu His Phe Arg
                5

<210> SEQ ID NO 90
<211> LENGTH: 9
<212> TYPE: PRT
<213> ORGANISM: Homo sapiens
<220> FEATURE:
<223> OTHER INFORMATION: Residues 115-123 of the PUMP-1 protein

<400> SEQUENCE: 90

Ser Tyr Thr Arg Asp Leu Pro His Ile
                5

<210> SEQ ID NO 91
<211> LENGTH: 9
<212> TYPE: PRT
<213> ORGANISM: Homo sapiens
<220> FEATURE:
<223> OTHER INFORMATION: Residues 112-120 of the PUMP-1 protein

<400> SEQUENCE: 91

Arg Ile Val Ser Tyr Thr Arg Asp Leu
                5

<210> SEQ ID NO 92
<211> LENGTH: 9
<212> TYPE: PRT
<213> ORGANISM: Homo sapiens
<220> FEATURE:
<223> OTHER INFORMATION: Residues 66-74 of the PUMP-1 protein
```

```
<400> SEQUENCE: 92

Phe Gly Leu Pro Ile Thr Gly Met Leu
                5

<210> SEQ ID NO 93
<211> LENGTH: 9
<212> TYPE: PRT
<213> ORGANISM: Homo sapiens
<220> FEATURE:
<223> OTHER INFORMATION: Residues 37-45 of the PUMP-1 protein

<400> SEQUENCE: 93

Asp Tyr Leu Lys Arg Phe Tyr Leu Tyr
                5

<210> SEQ ID NO 94
<211> LENGTH: 9
<212> TYPE: PRT
<213> ORGANISM: Homo sapiens
<220> FEATURE:
<223> OTHER INFORMATION: Residues 51-59 of the PUMP-1 protein

<400> SEQUENCE: 94

Asn Ala Asn Ser Leu Glu Ala Lys Leu
                5

<210> SEQ ID NO 95
<211> LENGTH: 9
<212> TYPE: PRT
<213> ORGANISM: Homo sapiens
<220> FEATURE:
<223> OTHER INFORMATION: Residues 166-174 of the PUMP-1 protein

<400> SEQUENCE: 95

Ser Tyr Pro Phe Lys Gly Pro Gly Asn
                5

<210> SEQ ID NO 96
<211> LENGTH: 9
<212> TYPE: PRT
<213> ORGANISM: Homo sapiens
<220> FEATURE:
<223> OTHER INFORMATION: Residues 10-18 of the PUMP-1 protein

<400> SEQUENCE: 96

Cys Leu Leu Pro Gly Ser Leu Ala Leu
                5

<210> SEQ ID NO 97
<211> LENGTH: 9
<212> TYPE: PRT
<213> ORGANISM: Homo sapiens
<220> FEATURE:
<223> OTHER INFORMATION: Residues 4-12 of the PUMP-1 protein

<400> SEQUENCE: 97

Thr Val Leu Cys Ala Val Cys Leu Leu
                5

<210> SEQ ID NO 98
<211> LENGTH: 9
<212> TYPE: PRT
<213> ORGANISM: Homo sapiens
<220> FEATURE:
<223> OTHER INFORMATION: Residues 31-39 of the PUMP-1 protein

<400> SEQUENCE: 98
```

```
Gln Trp Glu Gln Ala Gln Asp Tyr Leu
                5

<210> SEQ ID NO 99
<211> LENGTH: 9
<212> TYPE: PRT
<213> ORGANISM: Homo sapiens
<220> FEATURE:
<223> OTHER INFORMATION: Residues 3-11 of the PUMP-1 protein

<400> SEQUENCE: 99

Leu Thr Val Leu Cys Ala Val Cys Leu
                5

<210> SEQ ID NO 100
<211> LENGTH: 9
<212> TYPE: PRT
<213> ORGANISM: Homo sapiens
<220> FEATURE:
<223> OTHER INFORMATION: Residues 212-220 of the PUMP-1 protein

<400> SEQUENCE: 100

Ala Thr His Glu Leu Gly His Ser Leu
                5

<210> SEQ ID NO 101
<211> LENGTH: 9
<212> TYPE: PRT
<213> ORGANISM: Homo sapiens
<220> FEATURE:
<223> OTHER INFORMATION: Residues 238-246 of the PUMP-1 protein

<400> SEQUENCE: 101

Asn Gly Asp Pro Gln Asn Phe Lys Leu
                5

<210> SEQ ID NO 102
<211> LENGTH: 9
<212> TYPE: PRT
<213> ORGANISM: Homo sapiens
<220> FEATURE:
<223> OTHER INFORMATION: Residues 44-52 of the PUMP-1 protein

<400> SEQUENCE: 102

Leu Tyr Asp Ser Glu Thr Lys Asn Ala
                5

<210> SEQ ID NO 103
<211> LENGTH: 9
<212> TYPE: PRT
<213> ORGANISM: Homo sapiens
<220> FEATURE:
<223> OTHER INFORMATION: Residues 235-243 of the PUMP-1 protein

<400> SEQUENCE: 103

Thr Tyr Gly Asn Gly Asp Pro Gln Asn
                5

<210> SEQ ID NO 104
<211> LENGTH: 9
<212> TYPE: PRT
<213> ORGANISM: Homo sapiens
<220> FEATURE:
<223> OTHER INFORMATION: Residues 243-251 of the PUMP-1 protein

<400> SEQUENCE: 104
```

-continued

Asn Phe Lys Leu Ser Gln Asp Asp Ile
                5

<210> SEQ ID NO 105
<211> LENGTH: 9
<212> TYPE: PRT
<213> ORGANISM: Homo sapiens
<220> FEATURE:
<223> OTHER INFORMATION: Residues 8-16 of the PUMP-1 protein

<400> SEQUENCE: 105

Ala Val Cys Leu Leu Pro Gly Ser Leu
                5

<210> SEQ ID NO 106
<211> LENGTH: 9
<212> TYPE: PRT
<213> ORGANISM: Homo sapiens
<220> FEATURE:
<223> OTHER INFORMATION: Residues 12-20 of the PUMP-1 protein

<400> SEQUENCE: 106

Leu Pro Gly Ser Leu Ala Leu Pro Leu
                5

<210> SEQ ID NO 107
<211> LENGTH: 9
<212> TYPE: PRT
<213> ORGANISM: Homo sapiens
<220> FEATURE:
<223> OTHER INFORMATION: Residues 58-66 of the PUMP-1 protein

<400> SEQUENCE: 107

Lys Leu Lys Glu Met Gln Lys Phe Phe
                5

<210> SEQ ID NO 108
<211> LENGTH: 9
<212> TYPE: PRT
<213> ORGANISM: Homo sapiens
<220> FEATURE:
<223> OTHER INFORMATION: Residues 201-209 of the PUMP-1 protein

<400> SEQUENCE: 108

Gly Ser Ser Leu Gly Ile Asn Phe Leu
                5

<210> SEQ ID NO 109
<211> LENGTH: 9
<212> TYPE: PRT
<213> ORGANISM: Homo sapiens
<220> FEATURE:
<223> OTHER INFORMATION: Residues 208-216 of the PUMP-1 protein

<400> SEQUENCE: 109

Phe Leu Tyr Ala Ala Thr His Glu Leu
                5

<210> SEQ ID NO 110
<211> LENGTH: 9
<212> TYPE: PRT
<213> ORGANISM: Homo sapiens
<220> FEATURE:
<223> OTHER INFORMATION: Residues 120-128 of the PUMP-1 protein

<400> SEQUENCE: 110

Leu Pro His Ile Thr Val Asp Arg Leu

<210> SEQ ID NO 111
<211> LENGTH: 9
<212> TYPE: PRT
<213> ORGANISM: Homo sapiens
<220> FEATURE:
<223> OTHER INFORMATION: Residues 12-20 of the PUMP-1 protein

<400> SEQUENCE: 111

Leu Pro Gly Ser Leu Ala Leu Pro Leu
                5

<210> SEQ ID NO 112
<211> LENGTH: 9
<212> TYPE: PRT
<213> ORGANISM: Homo sapiens
<220> FEATURE:
<223> OTHER INFORMATION: Residues 8-16 of the PUMP-1 protein

<400> SEQUENCE: 112

Ala Val Cys Leu Leu Pro Gly Ser Leu
                5

<210> SEQ ID NO 113
<211> LENGTH: 9
<212> TYPE: PRT
<213> ORGANISM: Homo sapiens
<220> FEATURE:
<223> OTHER INFORMATION: Residues 84-92 of the PUMP-1 protein

<400> SEQUENCE: 113

Lys Pro Arg Cys Gly Val Pro Asp Val
                5

<210> SEQ ID NO 114
<211> LENGTH: 9
<212> TYPE: PRT
<213> ORGANISM: Homo sapiens
<220> FEATURE:
<223> OTHER INFORMATION: Residues 89-97 of the PUMP-1 protein

<400> SEQUENCE: 114

Val Pro Asp Val Ala Glu Tyr Ser Leu
                5

<210> SEQ ID NO 115
<211> LENGTH: 9
<212> TYPE: PRT
<213> ORGANISM: Homo sapiens
<220> FEATURE:
<223> OTHER INFORMATION: Residues 4-12 of the PUMP-1 protein

<400> SEQUENCE: 115

Thr Val Leu Cys Ala Val Cys Leu Leu
                5

<210> SEQ ID NO 116
<211> LENGTH: 9
<212> TYPE: PRT
<213> ORGANISM: Homo sapiens
<220> FEATURE:
<223> OTHER INFORMATION: Residues 178-186 of the PUMP-1 protein

<400> SEQUENCE: 116

His Ala Phe Ala Pro Gly Thr Gly Leu
                5

```
<210> SEQ ID NO 117
<211> LENGTH: 9
<212> TYPE: PRT
<213> ORGANISM: Homo sapiens
<220> FEATURE:
<223> OTHER INFORMATION: Residues 51-59 of the PUMP-1 protein

<400> SEQUENCE: 117

Asn Ala Asn Ser Leu Glu Ala Lys Leu
                 5

<210> SEQ ID NO 118
<211> LENGTH: 9
<212> TYPE: PRT
<213> ORGANISM: Homo sapiens
<220> FEATURE:
<223> OTHER INFORMATION: Residues 212-220 of the PUMP-1 protein

<400> SEQUENCE: 118

Ala Thr His Glu Leu Gly His Ser Leu
                 5

<210> SEQ ID NO 119
<211> LENGTH: 9
<212> TYPE: PRT
<213> ORGANISM: Homo sapiens
<220> FEATURE:
<223> OTHER INFORMATION: Residues 140-148 of the PUMP-1 protein

<400> SEQUENCE: 119

Ile Pro Leu His Phe Arg Lys Val Val
                 5

<210> SEQ ID NO 120
<211> LENGTH: 9
<212> TYPE: PRT
<213> ORGANISM: Homo sapiens
<220> FEATURE:
<223> OTHER INFORMATION: Residues 147-155 of the PUMP-1 protein

<400> SEQUENCE: 120

Val Val Trp Gly Thr Ala Asp Ile Met
                 5

<210> SEQ ID NO 121
<211> LENGTH: 9
<212> TYPE: PRT
<213> ORGANISM: Homo sapiens
<220> FEATURE:
<223> OTHER INFORMATION: Residues 208-216 of the PUMP-1 protein

<400> SEQUENCE: 121

Phe Leu Tyr Ala Ala Thr His Glu Leu
                 5

<210> SEQ ID NO 122
<211> LENGTH: 9
<212> TYPE: PRT
<213> ORGANISM: Homo sapiens
<220> FEATURE:
<223> OTHER INFORMATION: Residues 101-109 of the PUMP-1 protein

<400> SEQUENCE: 122

Ser Pro Lys Trp Thr Ser Lys Val Val
                 5
```

```
<210> SEQ ID NO 123
<211> LENGTH: 9
<212> TYPE: PRT
<213> ORGANISM: Homo sapiens
<220> FEATURE:
<223> OTHER INFORMATION: Residues 10-18 of the PUMP-1 protein

<400> SEQUENCE: 123

Cys Leu Leu Pro Gly Ser Leu Ala Leu
                5

<210> SEQ ID NO 124
<211> LENGTH: 9
<212> TYPE: PRT
<213> ORGANISM: Homo sapiens
<220> FEATURE:
<223> OTHER INFORMATION: Residues 3-11 of the PUMP-1 protein

<400> SEQUENCE: 124

Leu Thr Val Leu Cys Ala Val Cys Leu
                5

<210> SEQ ID NO 125
<211> LENGTH: 9
<212> TYPE: PRT
<213> ORGANISM: Homo sapiens
<220> FEATURE:
<223> OTHER INFORMATION: Residues 201-209 of the PUMP-1 protein

<400> SEQUENCE: 125

Gly Ser Ser Leu Gly Ile Asn Phe Leu
                5

<210> SEQ ID NO 126
<211> LENGTH: 9
<212> TYPE: PRT
<213> ORGANISM: Homo sapiens
<220> FEATURE:
<223> OTHER INFORMATION: Residues 134-142 of the PUMP-1 protein

<400> SEQUENCE: 126

Asn Met Trp Gly Lys Glu Ile Pro Leu
                5

<210> SEQ ID NO 127
<211> LENGTH: 9
<212> TYPE: PRT
<213> ORGANISM: Homo sapiens
<220> FEATURE:
<223> OTHER INFORMATION: Residues 112-120 of the PUMP-1 protein

<400> SEQUENCE: 127

Arg Ile Val Ser Tyr Thr Arg Asp Leu
                5

<210> SEQ ID NO 128
<211> LENGTH: 9
<212> TYPE: PRT
<213> ORGANISM: Homo sapiens
<220> FEATURE:
<223> OTHER INFORMATION: Residues 125-133 of the PUMP-1 protein

<400> SEQUENCE: 128

Val Asp Arg Leu Val Ser Lys Ala Leu
                5
```

```
<210> SEQ ID NO 129
<211> LENGTH: 9
<212> TYPE: PRT
<213> ORGANISM: Homo sapiens
<220> FEATURE:
<223> OTHER INFORMATION: Residues 66-74 of the PUMP-1 protein

<400> SEQUENCE: 129

Phe Gly Leu Pro Ile Thr Gly Met Leu
                5

<210> SEQ ID NO 130
<211> LENGTH: 9
<212> TYPE: PRT
<213> ORGANISM: Homo sapiens
<220> FEATURE:
<223> OTHER INFORMATION: Residues 134-142 of the PUMP-1 protein

<400> SEQUENCE: 130

Asn Met Trp Gly Lys Glu Ile Pro Leu
                5

<210> SEQ ID NO 131
<211> LENGTH: 9
<212> TYPE: PRT
<213> ORGANISM: Homo sapiens
<220> FEATURE:
<223> OTHER INFORMATION: Residues 56-64 of the PUMP-1 protein

<400> SEQUENCE: 131

Glu Ala Lys Leu Lys Glu Met Gln Lys
                5

<210> SEQ ID NO 132
<211> LENGTH: 9
<212> TYPE: PRT
<213> ORGANISM: Homo sapiens
<220> FEATURE:
<223> OTHER INFORMATION: Residues 101-109 of the PUMP-1 protein

<400> SEQUENCE: 132

Ser Pro Lys Trp Thr Ser Lys Val Val
                5

<210> SEQ ID NO 133
<211> LENGTH: 9
<212> TYPE: PRT
<213> ORGANISM: Homo sapiens
<220> FEATURE:
<223> OTHER INFORMATION: Residues 73-81 of the PUMP-1 protein

<400> SEQUENCE: 133

Met Leu Asn Ser Arg Val Ile Glu Ile
                5

<210> SEQ ID NO 134
<211> LENGTH: 9
<212> TYPE: PRT
<213> ORGANISM: Homo sapiens
<220> FEATURE:
<223> OTHER INFORMATION: Residues 84-92 of the PUMP-1 protein

<400> SEQUENCE: 134

Lys Pro Arg Cys Gly Val Pro Asp Val
                5

<210> SEQ ID NO 135
```

```
<211> LENGTH: 9
<212> TYPE: PRT
<213> ORGANISM: Homo sapiens
<220> FEATURE:
<223> OTHER INFORMATION: Residues 127-135 of the PUMP-1 protein

<400> SEQUENCE: 135

Arg Leu Val Ser Lys Ala Leu Asn Met
                5

<210> SEQ ID NO 136
<211> LENGTH: 9
<212> TYPE: PRT
<213> ORGANISM: Homo sapiens
<220> FEATURE:
<223> OTHER INFORMATION: Residues 105-113 of the PUMP-1 protein

<400> SEQUENCE: 136

Thr Ser Lys Val Val Thr Tyr Arg Ile
                5

<210> SEQ ID NO 137
<211> LENGTH: 9
<212> TYPE: PRT
<213> ORGANISM: Homo sapiens
<220> FEATURE:
<223> OTHER INFORMATION: Residues 51-59 of the PUMP-1 protein

<400> SEQUENCE: 137

Asn Ala Asn Ser Leu Glu Ala Lys Leu
                5

<210> SEQ ID NO 138
<211> LENGTH: 9
<212> TYPE: PRT
<213> ORGANISM: Homo sapiens
<220> FEATURE:
<223> OTHER INFORMATION: Residues 12-20 of the PUMP-1 protein

<400> SEQUENCE: 138

Leu Pro Gly Ser Leu Ala Leu Pro Leu
                5

<210> SEQ ID NO 139
<211> LENGTH: 9
<212> TYPE: PRT
<213> ORGANISM: Homo sapiens
<220> FEATURE:
<223> OTHER INFORMATION: Residues 120-128 of the PUMP-1 protein

<400> SEQUENCE: 139

Leu Pro His Ile Thr Val Asp Arg Leu
                5

<210> SEQ ID NO 140
<211> LENGTH: 9
<212> TYPE: PRT
<213> ORGANISM: Homo sapiens
<220> FEATURE:
<223> OTHER INFORMATION: Residues 178-186 of the PUMP-1 protein

<400> SEQUENCE: 140

His Ala Phe Ala Pro Gly Thr Gly Leu
                5

<210> SEQ ID NO 141
<211> LENGTH: 9
```

```
<212> TYPE: PRT
<213> ORGANISM: Homo sapiens
<220> FEATURE:
<223> OTHER INFORMATION: Residues 54-62 of the PUMP-1 protein

<400> SEQUENCE: 141

Ser Leu Glu Ala Lys Leu Lys Glu Met
                5

<210> SEQ ID NO 142
<211> LENGTH: 9
<212> TYPE: PRT
<213> ORGANISM: Homo sapiens
<220> FEATURE:
<223> OTHER INFORMATION: Residues 10-18 of the PUMP-1 protein

<400> SEQUENCE: 142

Cys Leu Leu Pro Gly Ser Leu Ala Leu
                5

<210> SEQ ID NO 143
<211> LENGTH: 9
<212> TYPE: PRT
<213> ORGANISM: Homo sapiens
<220> FEATURE:
<223> OTHER INFORMATION: Residues 208-216 of the PUMP-1 protein

<400> SEQUENCE: 143

Phe Leu Tyr Ala Ala Thr His Glu Leu
                5

<210> SEQ ID NO 144
<211> LENGTH: 9
<212> TYPE: PRT
<213> ORGANISM: Homo sapiens
<220> FEATURE:
<223> OTHER INFORMATION: Residues 125-133 of the PUMP-1 protein

<400> SEQUENCE: 144

Val Asp Arg Leu Val Ser Lys Ala Leu
                5

<210> SEQ ID NO 145
<211> LENGTH: 9
<212> TYPE: PRT
<213> ORGANISM: Homo sapiens
<220> FEATURE:
<223> OTHER INFORMATION: Residues 158-166 of the PUMP-1 protein

<400> SEQUENCE: 145

Phe Ala Arg Gly Ala His Gly Asp Ser
                5

<210> SEQ ID NO 146
<211> LENGTH: 9
<212> TYPE: PRT
<213> ORGANISM: Homo sapiens
<220> FEATURE:
<223> OTHER INFORMATION: Residues 36-44 of the PUMP-1 protein

<400> SEQUENCE: 146

Gln Asp Tyr Leu Lys Arg Phe Tyr Leu
                5

<210> SEQ ID NO 147
<211> LENGTH: 9
<212> TYPE: PRT
```

```
<213> ORGANISM: Homo sapiens
<220> FEATURE:
<223> OTHER INFORMATION: Residues 212-220 of the PUMP-1 protein

<400> SEQUENCE: 147

Ala Thr His Glu Leu Gly His Ser Leu
                5

<210> SEQ ID NO 148
<211> LENGTH: 9
<212> TYPE: PRT
<213> ORGANISM: Homo sapiens
<220> FEATURE:
<223> OTHER INFORMATION: Residues 116-124 of the PUMP-1 protein

<400> SEQUENCE: 148

Tyr Thr Arg Asp Leu Pro His Ile Thr
                5

<210> SEQ ID NO 149
<211> LENGTH: 9
<212> TYPE: PRT
<213> ORGANISM: Homo sapiens
<220> FEATURE:
<223> OTHER INFORMATION: Residues 62-70 of the PUMP-1 protein

<400> SEQUENCE: 149

Met Gln Lys Phe Phe Gly Leu Pro Ile
                5

<210> SEQ ID NO 150
<211> LENGTH: 9
<212> TYPE: PRT
<213> ORGANISM: Homo sapiens
<220> FEATURE:
<223> OTHER INFORMATION: Residues 159-167 of the PUMP-1 protein

<400> SEQUENCE: 150

Ala Thr Gly Ala His Gly Asp Ser Tyr
                5

<210> SEQ ID NO 151
<211> LENGTH: 9
<212> TYPE: PRT
<213> ORGANISM: Homo sapiens
<220> FEATURE:
<223> OTHER INFORMATION: Residues 30-38 of the PUMP-1 protein

<400> SEQUENCE: 151

Leu Gln Trp Glu Gln Ala Gln Asp Tyr
                5

<210> SEQ ID NO 152
<211> LENGTH: 9
<212> TYPE: PRT
<213> ORGANISM: Homo sapiens
<220> FEATURE:
<223> OTHER INFORMATION: Residues 196-204 of the PUMP-1 protein

<400> SEQUENCE: 152

Glu Arg Trp Thr Asp Gly Ser Ser Leu
                5

<210> SEQ ID NO 153
<211> LENGTH: 9
<212> TYPE: PRT
<213> ORGANISM: Homo sapiens
```

```
<220> FEATURE:
<223> OTHER INFORMATION: Residues 40-48 of the PUMP-1 protein

<400> SEQUENCE: 153

Lys Arg Phe Tyr Leu Tyr Asp Ser Glu
                5

<210> SEQ ID NO 154
<211> LENGTH: 9
<212> TYPE: PRT
<213> ORGANISM: Homo sapiens
<220> FEATURE:
<223> OTHER INFORMATION: Residues 1-9 of the PUMP-1 protein

<400> SEQUENCE: 154

Met Arg Leu Thr Val Leu Cys Ala Val
                5

<210> SEQ ID NO 155
<211> LENGTH: 9
<212> TYPE: PRT
<213> ORGANISM: Homo sapiens
<220> FEATURE:
<223> OTHER INFORMATION: Residues 144-152 of the PUMP-1 protein

<400> SEQUENCE: 155

Phe Arg Lys Val Val Trp Gly Thr Ala
                5

<210> SEQ ID NO 156
<211> LENGTH: 9
<212> TYPE: PRT
<213> ORGANISM: Homo sapiens
<220> FEATURE:
<223> OTHER INFORMATION: Residues 117-125 of the PUMP-1 protein

<400> SEQUENCE: 156

Thr Arg Asp Leu Pro His Ile Thr Val
                5

<210> SEQ ID NO 157
<211> LENGTH: 9
<212> TYPE: PRT
<213> ORGANISM: Homo sapiens
<220> FEATURE:
<223> OTHER INFORMATION: Residues 134-142 of the PUMP-1 protein

<400> SEQUENCE: 157

Asn Met Trp Gly Lys Glu Ile Pro Leu
                5

<210> SEQ ID NO 158
<211> LENGTH: 9
<212> TYPE: PRT
<213> ORGANISM: Homo sapiens
<220> FEATURE:
<223> OTHER INFORMATION: Residues 96-104 of the PUMP-1 protein

<400> SEQUENCE: 158

Ser Leu Phe Pro Asn Ser Pro Lys Trp
                5

<210> SEQ ID NO 159
<211> LENGTH: 9
<212> TYPE: PRT
<213> ORGANISM: Homo sapiens
<220> FEATURE:
```

```
<223> OTHER INFORMATION: Residues 62-70 of the PUMP-1 protein

<400> SEQUENCE: 159

Met Gln Lys Phe Phe Gly Leu Pro Ile
                5

<210> SEQ ID NO 160
<211> LENGTH: 9
<212> TYPE: PRT
<213> ORGANISM: Homo sapiens
<220> FEATURE:
<223> OTHER INFORMATION: Residues 35-43 of the PUMP-1 protein

<400> SEQUENCE: 160

Ala Gln Asp Tyr Leu Lys Arg Phe Tyr
                5

<210> SEQ ID NO 161
<211> LENGTH: 9
<212> TYPE: PRT
<213> ORGANISM: Homo sapiens
<220> FEATURE:
<223> OTHER INFORMATION: Residues 208-216 of the PUMP-1 protein

<400> SEQUENCE: 161

Phe Leu Tyr Ala Ala Thr His Glu Leu
                5

<210> SEQ ID NO 162
<211> LENGTH: 9
<212> TYPE: PRT
<213> ORGANISM: Homo sapiens
<220> FEATURE:
<223> OTHER INFORMATION: Residues 76-84 of the PUMP-1 protein

<400> SEQUENCE: 162

Ser Arg Val Ile Glu Ile Met Gln Lys
                5

<210> SEQ ID NO 163
<211> LENGTH: 9
<212> TYPE: PRT
<213> ORGANISM: Homo sapiens
<220> FEATURE:
<223> OTHER INFORMATION: Residues 126-134 of the PUMP-1 protein

<400> SEQUENCE: 163

Asp Arg Leu Val Ser Lys Ala Leu Asn
                5

<210> SEQ ID NO 164
<211> LENGTH: 9
<212> TYPE: PRT
<213> ORGANISM: Homo sapiens
<220> FEATURE:
<223> OTHER INFORMATION: Residues 60-68 of the PUMP-1 protein

<400> SEQUENCE: 164

Lys Glu Met Gln Lys Phe Phe Gly Leu
                5

<210> SEQ ID NO 165
<211> LENGTH: 9
<212> TYPE: PRT
<213> ORGANISM: Homo sapiens
<220> FEATURE:
<223> OTHER INFORMATION: Residues 58-66 of the PUMP-1 protein
```

```
<400> SEQUENCE: 165

Lys Leu Lys Glu Met Gln Lys Phe Phe
                5

<210> SEQ ID NO 166
<211> LENGTH: 9
<212> TYPE: PRT
<213> ORGANISM: Homo sapiens
<220> FEATURE:
<223> OTHER INFORMATION: Residues 256-264 of the PUMP-1 protein

<400> SEQUENCE: 166

Lys Leu Tyr Gly Lys Arg Ser Asn Ser
                5

<210> SEQ ID NO 167
<211> LENGTH: 9
<212> TYPE: PRT
<213> ORGANISM: Homo sapiens
<220> FEATURE:
<223> OTHER INFORMATION: Residues 85-93 of the PUMP-1 protein

<400> SEQUENCE: 167

Pro Arg Cys Gly Val Pro Asp Val Ala
                5

<210> SEQ ID NO 168
<211> LENGTH: 9
<212> TYPE: PRT
<213> ORGANISM: Homo sapiens
<220> FEATURE:
<223> OTHER INFORMATION: Residues 111-119 of the PUMP-1 protein

<400> SEQUENCE: 168

Tyr Arg Ile Val Ser Tyr Thr Arg Asp
                5

<210> SEQ ID NO 169
<211> LENGTH: 9
<212> TYPE: PRT
<213> ORGANISM: Homo sapiens
<220> FEATURE:
<223> OTHER INFORMATION: Residues 178-186 of the PUMP-1 protein

<400> SEQUENCE: 169

His Ala Phe Ala Pro Gly Thr Gly Leu
                5

<210> SEQ ID NO 170
<211> LENGTH: 9
<212> TYPE: PRT
<213> ORGANISM: Homo sapiens
<220> FEATURE:
<223> OTHER INFORMATION: Residues 87-95 of the PUMP-1 protein

<400> SEQUENCE: 170

Cys Gly Val Pro Asp Val Ala Glu Tyr
                5

<210> SEQ ID NO 171
<211> LENGTH: 9
<212> TYPE: PRT
<213> ORGANISM: Homo sapiens
<220> FEATURE:
<223> OTHER INFORMATION: Residues 202-210 of the PUMP-1 protein
```

<400> SEQUENCE: 171

Ser Ser Leu Gly Ile Asn Phe Leu Tyr
                5

<210> SEQ ID NO 172
<211> LENGTH: 9
<212> TYPE: PRT
<213> ORGANISM: Homo sapiens
<220> FEATURE:
<223> OTHER INFORMATION: Residues 79-87 of the PUMP-1 protein

<400> SEQUENCE: 172

Ile Glu Ile Met Gln Lys Pro Arg Cys
                5

<210> SEQ ID NO 173
<211> LENGTH: 9
<212> TYPE: PRT
<213> ORGANISM: Homo sapiens
<220> FEATURE:
<223> OTHER INFORMATION: Residues 60-68 of the PUMP-1 protein

<400> SEQUENCE: 173

Lys Glu Met Gln Lys Phe Phe Gly Leu
                5

<210> SEQ ID NO 174
<211> LENGTH: 9
<212> TYPE: PRT
<213> ORGANISM: Homo sapiens
<220> FEATURE:
<223> OTHER INFORMATION: Residues 225-233 of the PUMP-1 protein

<400> SEQUENCE: 174

Ser Ser Asp Pro Asn Ala Val Met Tyr
                5

<210> SEQ ID NO 175
<211> LENGTH: 9
<212> TYPE: PRT
<213> ORGANISM: Homo sapiens
<220> FEATURE:
<223> OTHER INFORMATION: Residues 47-55 of the PUMP-1 protein

<400> SEQUENCE: 175

Ser Glu Thr Lys Asn Ala Asn Ser Leu
                5

<210> SEQ ID NO 176
<211> LENGTH: 9
<212> TYPE: PRT
<213> ORGANISM: Homo sapiens
<220> FEATURE:
<223> OTHER INFORMATION: Residues 195-203 of the PUMP-1 protein

<400> SEQUENCE: 176

Asp Glu Arg Trp Thr Asp Gly Ser Ser
                5

<210> SEQ ID NO 177
<211> LENGTH: 9
<212> TYPE: PRT
<213> ORGANISM: Homo sapiens
<220> FEATURE:
<223> OTHER INFORMATION: Residues 214-222 of the PUMP-1 protein

<400> SEQUENCE: 177

```
His Glu Leu Gly His Ser Leu Gly Met
                5

<210> SEQ ID NO 178
<211> LENGTH: 9
<212> TYPE: PRT
<213> ORGANISM: Homo sapiens
<220> FEATURE:
<223> OTHER INFORMATION: Residues 22-30 of the PUMP-1 protein

<400> SEQUENCE: 178

Gln Glu Ala Gly Gly Met Ser Glu Leu
                5

<210> SEQ ID NO 179
<211> LENGTH: 9
<212> TYPE: PRT
<213> ORGANISM: Homo sapiens
<220> FEATURE:
<223> OTHER INFORMATION: Residues 249-257 of the PUMP-1 protein

<400> SEQUENCE: 179

Asp Asp Ile Lys Gly Ile Gln Lys Leu
                5

<210> SEQ ID NO 180
<211> LENGTH: 9
<212> TYPE: PRT
<213> ORGANISM: Homo sapiens
<220> FEATURE:
<223> OTHER INFORMATION: Residues 93-101 of the PUMP-1 protein

<400> SEQUENCE: 180

Ala Glu Tyr Ser Leu Phe Pro Asn Ser
                5

<210> SEQ ID NO 181
<211> LENGTH: 9
<212> TYPE: PRT
<213> ORGANISM: Homo sapiens
<220> FEATURE:
<223> OTHER INFORMATION: Residues 138-146 of the PUMP-1 protein

<400> SEQUENCE: 181

Lys Glu Ile Pro Leu His Phe Arg Lys

<210> SEQ ID NO 182
<211> LENGTH: 9
<212> TYPE: PRT
<213> ORGANISM: Homo sapiens
<220> FEATURE:
<223> OTHER INFORMATION: Residues 184-192 of the PUMP-1 protein

<400> SEQUENCE: 182

Thr Gly Leu Gly Gly Asp Ala His Phe
                5

<210> SEQ ID NO 183
<211> LENGTH: 9
<212> TYPE: PRT
<213> ORGANISM: Homo sapiens
<220> FEATURE:
<223> OTHER INFORMATION: Residues 200-208 of the PUMP-1 protein

<400> SEQUENCE: 183

Asp Gly Ser Ser Leu Gly Ile Asn Phe
```

<210> SEQ ID NO 184
<211> LENGTH: 9
<212> TYPE: PRT
<213> ORGANISM: Homo sapiens
<220> FEATURE:
<223> OTHER INFORMATION: Residues 35-43 of the PUMP-1 protein

<400> SEQUENCE: 184

Ala Gln Asp Tyr Leu Lys Arg Phe Tyr
                5

<210> SEQ ID NO 185
<211> LENGTH: 9
<212> TYPE: PRT
<213> ORGANISM: Homo sapiens
<220> FEATURE:
<223> OTHER INFORMATION: Residues 34-42 of the PUMP-1 protein

<400> SEQUENCE: 185

Gln Ala Gln Asp Tyr Leu Lys Arg Phe
                5

<210> SEQ ID NO 186
<211> LENGTH: 9
<212> TYPE: PRT
<213> ORGANISM: Homo sapiens
<220> FEATURE:
<223> OTHER INFORMATION: Residues 30-38 of the PUMP-1 protein

<400> SEQUENCE: 186

Leu Gln Trp Glu Gln Ala Gln Asp Tyr
                5

<210> SEQ ID NO 187
<211> LENGTH: 9
<212> TYPE: PRT
<213> ORGANISM: Homo sapiens
<220> FEATURE:
<223> OTHER INFORMATION: Residues 250-258 of the PUMP-1 protein

<400> SEQUENCE: 187

Asp Ile Lys Gly Ile Gln Lys Leu Tyr
                5

<210> SEQ ID NO 188
<211> LENGTH: 9
<212> TYPE: PRT
<213> ORGANISM: Homo sapiens
<220> FEATURE:
<223> OTHER INFORMATION: Residues 150-158 of the PUMP-1 protein

<400> SEQUENCE: 188

Gly Thr Ala Asp Ile Met Ile Gly Phe

<210> SEQ ID NO 189
<211> LENGTH: 9
<212> TYPE: PRT
<213> ORGANISM: Homo sapiens
<220> FEATURE:
<223> OTHER INFORMATION: Residues 37-45 of the PUMP-1 protein

<400> SEQUENCE: 189

Asp Tyr Leu Lys Arg Phe Tyr Leu Tyr

-continued

```
<210> SEQ ID NO 190
<211> LENGTH: 57
<212> TYPE: PRT
<213> ORGANISM: Homo sapiens
<220> FEATURE:
<223> OTHER INFORMATION: TADG-12 catalytic domain

<400> SEQUENCE: 190

Val Val Thr Ala Ala His Cys Val Tyr Asp Leu Tyr Leu Pro Lys
                 5                  10                  15

Ser Trp Thr Ile Gln Val Gly Leu Val Ser Leu Leu Asp Asn Pro
                20                  25                  30

Ala Pro Ser His Leu Val Glu Lys Ile Val Tyr His Ser Lys Tyr
                35                  40                  45

Lys Pro Lys Arg Leu Gly Asn Asp Ile Ala Leu Leu
                50                  55      57

<210> SEQ ID NO 191
<211> LENGTH: 8
<212> TYPE: PRT
<213> ORGANISM: Homo sapiens
<220> FEATURE:
<223> OTHER INFORMATION: site of 133 bp insert in the TADG-12 catalytic
      domain

<400> SEQUENCE: 191

His Cys Val Tyr Asp Leu Tyr Leu
                 5           8
```

METHODS FOR THE EARLY DIAGNOSIS OF OVARIAN CANCER

CROSS-REFERENCE TO RELATED APPLICATIONS

This is a continuation-in-part application which claims the benefit of priority under 35 USC §120 of U.S. Ser. No. 09/835,948, filed Apr. 16, 2001 now abandoned, which is a divisional application of Ser. No. 09/492,543 filed Jan. 27, 2000 now U.S. Pat. No. 6,316,213, which is a continuation-in-part and claims the benefit of priority under 35 USC §120 of U.S. Ser. No. 09/039,211, filed Mar. 14, 1998, now U.S. Pat. No. 6,303,318 which claims benefit of provisional patent application U.S. Ser. No. 60/041,404, filed Mar. 19, 1997, now abandoned.

BACKGROUND OF THE INVENTION

1. Field of the Invention

Generally, the present invention relates to the fields of molecular biology and medicine. More specifically, the present invention is in the field of cancer research, especially ovarian cancer diagnosis.

2. Background of the Invention

In order for malignant cells to grow, spread or metastasize, they must have the capacity to invade local host tissue, dissociate or shed from the primary tumor, enter and survive in the bloodstream, implant by invasion into the surface of the target organ and establish an environment conducive for new colony growth (including the induction of angiogenic and growth factors). During this progression, natural tissue barriers such as basement membranes and connective tissue have to be degraded. These barriers include collagen, laminin, fibronectin, proteoglycans and extracellular matrix glycoproteins. Degradation of these natural barriers, both those surrounding the primary tumor and at the sites of metastatic invasion, is believed to be brought about by the action of a matrix of extracellular proteases.

Proteases have been classified into four families: serine proteases, metallo-proteases, aspartic proteases and cysteine proteases. Many proteases have been shown to be involved in human disease processes and these enzymes are targets for the development of inhibitors as new therapeutic agents. Certain individual proteases are induced and overexpressed in a diverse group of cancers, and as such, are potential candidates for markers of early diagnosis and targets for possible therapeutic intervention. A group of examples are shown in Table 1.

There is a good body of evidence supporting the down-regulation or inhibition of individual proteases and the reduction in invasive capacity or malignancy. In work by Clark et al., inhibition of in vitro growth of human small cell lung cancer was demonstrated using a general serine protease inhibitor. More recently, Torres-Rosedo et al., [*Proc. Natl. Acad. Sci. USA.* 90, 7181–7185 (1993)] demonstrated an inhibition of hepatoma tumor cell growth using specific antisense inhibitors for the serine protease hepsin gene. Metastatic potential of melanoma cells has also been shown to be reduced in a mouse model using a synthetic inhibitor (batimastat) of metallo-proteases. Powell et al. [*Cancer Research*, 53, 417–422 (1993)] presented evidence to confirm that the expression of extracellular proteases in a non-metastatic prostate cancer cell line enhances their malignant progression. Specifically, enhanced metastasis was demonstrated after introducing and expressing the PUMP-1 metallo-protease gene. There is also a body of data to support the notion that expression of cell surface proteases on relatively non-metastatic cell types increases the invasive potential of such cells.

To date, ovarian cancer remains the number one killer of women with gynecologic malignant hyperplasia. Approximately 75% of women diagnosed with such cancers are already at an advanced stage (III and IV) of the disease at their initial diagnosis. During the past 20 years, neither diagnosis nor five-year survival rates have greatly improved for these patients. This is substantially due to the high percentage of high-stage initial detection of the disease. Therefore, the challenge remains to develop new markers that improve early diagnosis and thereby reduce the percentage of high-stage initial diagnoses. The ability to disengage from one tissue and re-engage the surface of another tissue is what provides for the morbidity and mortality associated with this disease. Therefore, extracellular proteases may be good candidates for markers of malignant ovarian hyperplasia.

Thus, the prior art is deficient in a tumor marker useful as an indicator of early disease, particularly for ovarian cancers. The present invention fulfills this long-standing need and desire in the art.

TABLE 1

Known proteases expressed in various cancers

| | Gastric | Brain | Breast | Ovarian |
|---|---|---|---|---|
| Serine Proteases: | uPA PAI-1 | uPA PAI-1 tPA | NES-1 uPA | NES-1 uPA PAI-2 |
| Cysteine Proteases: | Cathepsin B Cathepsin L | Cathepsin L | Cathepsin B Cathepsin L | Cathepsin B Cathepsin L |
| Metallo-proteases: | Matrilysin* Collagenase* Stromelysin-1* | Matrilysin Stromelysin Gelatinase B | Stromelysin-3 MMP-8 MMP-9 Gelatinase A | MMP-2 | uPA, Urokinase-type plasminogen activator;
tPA, Tissue-type plasminogen activator;
PAI-I, Plasminogen activator 0 inhibitors;
PAI-2, Plasminogen activator inhibitors;
NES-1, Normal epithelial cell-specific-1;
MMP, Matrix P metallo-protease.
*Overexpressed in gastrointestinal ulcers.

SUMMARY OF THE INVENTION

This invention allows for the detection of cancer, especially ovarian cancer, by screening for PUMP-1 (matrix metalloprotease 7) mRNA in tissue. PUMP-1 protease is shown herein to be specifically associated with the surface of 80 percent of ovarian and other tumors. Proteases are considered to be an integral part of tumor growth and metastasis, and therefore, markers indicative of their presence or absence are useful for the diagnosis of cancer. Furthermore, the present invention is useful for treatment (i.e., by inhibiting PUMP-1 or expression of PUMP-1), for targeted therapy, for vaccination, etc.

In one embodiment of the present invention, there is provided a method for detecting malignant hyperplasia in a biological sample by detecting PUMP-1 mRNA in the sample. The presence of the PUMP-1 mRNA in the sample is indicative of the presence of malignant hyperplasia, and the absence of the PUMP-1 mRNA in the sample is indicative of the absence of malignant hyperplasia.

In another embodiment of the present invention, there are provided methods of inhibiting expression of PUMP-1 in a cell by introducing into a cell a vector encoding an antisense PUMP-1 mRNA or an antibody that binds the PUMP-1 protein.

In yet another embodiment of the present invention, there is provided a method of targeted therapy to an individual, comprising the step of administering a compound to an individual, wherein the compound has a targeting moiety and a therapeutic moiety, wherein the targeting moiety is specific for PUMP-1.

In still yet another embodiment of the present invention, there are provided methods of vaccinating an individual against PUMP-1 or produce immune-activated cells directed toward PUMP-1 by inoculating an individual with a PUMP-1 protein or fragment thereof.

In still another embodiment of the present invention, there are provided compositions comprising immunogenic fragments of PUMP-1 protein or an oligonucleotide having a sequence complementary to SEQ ID No.29. Also embodied is a method of treating a neoplastic state in an individual in need of such treatment with an effective dose of the above-described oligonucleotide.

In another embodiment of the present invention, there is provided a method of screening for compounds that inhibit PUMP-1 activity, comprising the steps of contacting a sample with a compound, wherein the sample comprises PUMP-1 protein; and assaying for PUMP-1 protease activity. A decrease in the PUMP-1 protease activity in the presence of the compound relative to PUMP-1 protease activity in the absence of the compound is indicative of a compound that inhibits PUMP-1 activity.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 10 shows Northern blot analysis of hepsin expression in normal ovary and ovarian carcinomas.

FIG. 11 shows hepsin expression in normal (N), mucinous (M) and serous (S) low malignant potential (LMP) tumors and carcinomas (CA).

FIG. 15 shows the TADG-12 catalytic domain including an insert near the His 5'-end.

FIG. 20 shows immunohistochemical staining of PUMP-1 in normal ovary and ovarian tumor tissues.

DETAILED DESCRIPTION OF THE INVENTION

Figure 1:
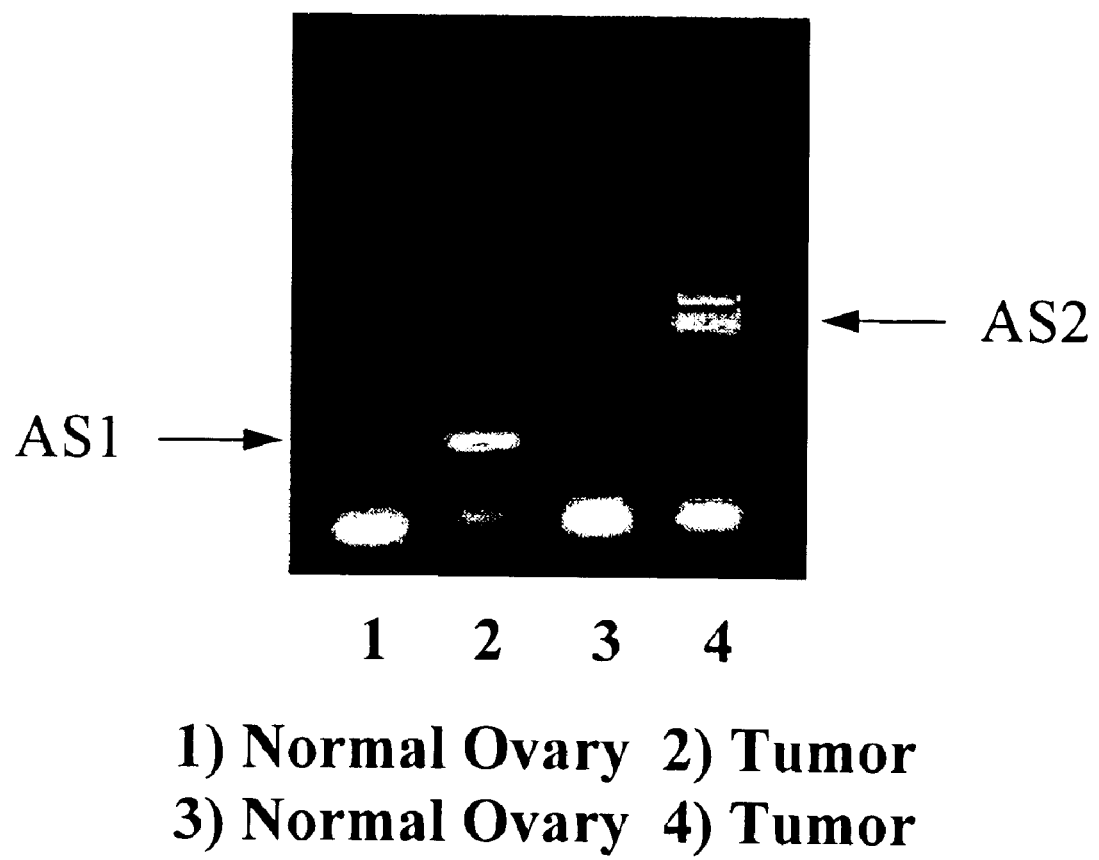
FIG. 1 shows agarose gel comparison of PCR products derived from normal and carcinoma cDNA.

This invention identifies PUMP-1 (matrix metalloprotease 7) protease as a marker for ovarian tumor cells. In various combinations with other proteases, PUMP-1 expression is characteristic of individual tumor types. Such information provides the basis for diagnostic tests (assays or immunohistochemistry) and prognostic evaluation (depending on the display pattern). Long-term treatment of tumor growth, invasion and metastasis has not succeeded with existing chemotherapeutic agents. Most tumors become resistant to drugs after multiple cycles of chemotherapy. The present invention identifies PUMP-1 as a new therapeutic intervention target utilizing either antibodies directed at the protease, antisense vehicles for downregulation or protease inhibitors for the design of new drugs.

A primary object of the present invention is a method for detecting the presence of malignant hyperplasia in a tissue sample. The cancer is detected by analyzing a biological sample for the presence of markers to proteases that are specific indicators of certain types of cancer cells. This object may be accomplished by isolating mRNA from a sample or by detection of proteins by polyclonal or preferably monoclonal antibodies. When using mRNA detection, the method may be carried out by converting the isolated mRNA to cDNA according to standard methods; treating the converted cDNA with amplification reaction reagents (such as cDNA PCR reaction reagents) in a container along with an appropriate mixture of nucleic acid primers selected from the list in Table 2; reacting the contents of the container to produce amplification products; and analyzing the amplification products to detect the presence of malignant hyperplasia markers in the sample. The analyzing step may be accomplished using Northern Blot analysis to detect the presence of malignant hyperplasia markers in the amplification product. Northern Blot analysis is known in the art. The analysis step may be further accomplished by quantatively detecting the presence of malignant hyperplasia marker in the amplification products, and comparing the quantity of marker detected against a panel of expected values for known presence or absence in normal and malignant tissue derived using similar primers.

The present invention also provides various nucleic acid sequences that are useful in the methods disclosed herein. These nucleic acid sequences are listed in Table 2. It is anticipated that these nucleic acid sequences be used in mixtures to accomplish the utility of this invention. The skilled artisan may be able to develop other nucleic acid sequences and mixtures thereof to accomplish the benefit of this invention, but it is advantageous to have the sequences listed in Table 2 available without undue experimentation.

The present invention provides a method for detecting malignant hyperplasia in a biological sample, comprising the steps of isolating mRNA from the sample; and detecting PUMP-1 mRNA in the sample. The presence of the PUMP-1 mRNA in the sample is indicative of the presence of malignant hyperplasia, wherein the absence of the PUMP-1 mRNA in the sample is indicative of the absence of malignant hyperplasia. This method may further comprise the step of comparing the PUMP-1 mRNA to reference information, wherein the comparison provides a diagnosis and/or determines a treatment of the malignant hyperplasia. A typical means of detection of PUMP-1 mRNA is by PCR amplification, which, preferably, uses primers shown in SEQ ID No. 16 and SEQ ID No. 17. Representative biological samples are blood, urine, saliva, tears, interstitial fluid, ascites fluid, tumor tissue biopsy and circulating tumor cells.

The present invention is further directed toward a method of inhibiting expression of PUMP-1 in a cell, comprising the step of introducing into a cell a vector comprises a PUMP-1 gene operably linked in opposite orientation to elements necessary for expression, wherein expression of the vector produces PUMP-1 antisense mRNA in the cell. The PUMP-1 antisense mRNA hybridizes to endogenous PUMP-1 mRNA, thereby inhibiting expression of PUMP-1 in the cell.

The present invention is still further directed toward a method of inhibiting a PUMP-1 protein in a cell, comprising the step of introducing an antibody into a cell, wherein the antibody is specific for a PUMP-1 protein or a fragment thereof. Binding of the antibody to PUMP-1 inhibits the PUMP-1 protein. Preferably, the PUMP-1 fragment is a 9-residue fragment up to a 20-residue fragment, and more preferably, the 9-residue fragment is SEQ ID Nos. 30, 31, 32, 33, 50, 51, 70, 110, 111, 150, 151 and 152.

The present invention is also directed toward a method of targeted therapy to an individual, comprising the step of administering a compound to an individual, wherein the compound has a targeting moiety and a therapeutic moiety, and wherein the targeting moiety is specific for PUMP-1. Preferably, the targeting moiety is an antibody specific for PUMP-1 or a ligand or ligand binding domain that binds PUMP-1. Likewise, the therapeutic moiety is preferably a radioisotope, a toxin, a chemotherapeutic agent, an immune stimulant or cytotoxic agent. Generally, the individual suffers from a disease such as ovarian cancer, lung cancer, prostate cancer, colon cancer or another cancer in which hepsin is overexpressed.

The present invention is additionally directed toward a method of vaccinating an individual against PUMP-1, comprising the steps of inoculating an individual with a PUMP-1 protein or fragment thereof. Inoculation with the PUMP-1 protein, or fragment thereof, elicits an immune response in the individual, thereby vaccinating the individual against PUMP-1. Generally, this method is applicable when the individual has cancer, is suspected of having cancer or is at risk of getting cancer. Sequences of preferred PUMP-1 proteins or fragment thereof are shown in SEQ ID Nos. 30, 31, 32, 33, 50, 51, 70, 110, 111, 150, 151 and 152.

The present invention is yet directed toward a method of producing immune-activated cells directed toward PUMP-1, comprising the steps of exposing immune cells to PUMP-1 protein or fragment thereof. Typically, exposure to PUMP-1 protein or fragment thereof activates the immune cells, thereby producing immune-activated cells directed toward PUMP-1. Generally, the immune-activated cells are B-cells, T-cells and/or dendritic cells. Preferably, the PUMP-1 fragment is a 9-residue fragment up to a 20-residue fragment, and more preferably, the 9-residue fragment is SEQ ID Nos. 30, 31, 32, 33, 50, 51, 70, 110, 111, 150, 151 and 152. Oftentimes, the dendritic cells are isolated from an individual prior to exposure and then reintroduced into the individual subsequent to the exposure. Typically, the individual has cancer, is suspected of having cancer or is at risk of getting cancer.

The present invention is further directed toward an immunogenic composition, comprising an immunogenic fragment of PUMP-1 protein and an appropriate adjuvant. Preferably, the fragment is a 9-residue fragment up to a 20-residue fragment, and more preferably, the 9-residue fragment is SEQ ID Nos. 30, 31, 32, 33, 50, 51, 70, 110, 111, 150, 151 and 152.

The present invention is further directed toward an oligonucleotide having a sequence complementary to SEQ ID No.29 or a frgament thereof. The present invention further provides a composition comprising the above-described oligonucleotide and a physiologically acceptable carrier, and a method of treating a neoplastic state in an individual in need of such treatment, comprising the step of administering to the individual an effective dose of the above-described oligonucleotide. Typically, the neoplastic state may be ovarian cancer, breast cancer, lung cancer, colon cancer, prostate cancer or another cancer in which PUMP-1 is overexpressed.

The present invention is still further directed toward a method of screening for compounds that inhibit PUMP-1 activity, comprising the steps of contacting a sample with a compound, wherein the sample comprises PUMP-1 protein; and assaying for PUMP-1 protease activity. A decrease in the PUMP-1 protease activity in the presence of the compound relative to PUMP-1 protease activity in the absence of the compound is indicative of a compound that inhibits PUMP-1 activity.

It will be apparent to one skilled in the art that various substitutions and modifications may be made to the invention disclosed herein without departing from the scope and spirit of the invention.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. 1985); "Transcription and Translation" (B. D. Hames & S. J. Higgins eds. 1984); "Animal Cell Culture" (R. I. Freshney, ed. 1986); "Immobilized Cells And Enzymes" (IRL Press, 1986); B. Perbal, "A Practical Guide To Molecular Cloning" (1984).

Therefore, if appearing herein, the following terms shall have the definitions set out below.

As used herein, the term "cDNA" shall refer to the DNA copy of the mRNA transcript of a gene.

As used herein, the term "PCR" refers to the polymerase chain reaction that is the subject of U.S. Pat. Nos. 4,683,195 and 4,683,202 to Mullis, as well as other improvements now known in the art.

The present invention comprises a vector comprising a DNA sequence which encodes a PUMP-1 protein, wherein said vector is capable of replication in a host, and comprises, in operable linkage: a) an origin of replication; b) a promoter; and c) a DNA sequence coding for said PUMP-1 protein. Preferably, the vector of the present invention contains a portion of the DNA sequence shown in SEQ ID No. 28 or 29. Vectors may be used to amplify and/or express nucleic acid encoding a PUMP-1 protein, a fragment of PUMP-1 protein, or an antisense PUMP-1 mRNA.

An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites and sequences which control the termination of transcription and translation. Methods which are well known to those skilled in the art can be used to construct expression vectors containing appropriate transcriptional and translational control signals. See, for example, techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

As used herein, the term "host" is meant to include not only prokaryotes but also eukaryotes such as yeast, plant and animal cells. A recombinant DNA molecule or gene which encodes a human PUMP-1 protein of the present invention can be used to transform a host using any of the techniques commonly known to those of ordinary skill in the art. Especially preferred is the use of a vector containing coding sequences for the gene which encodes a human PUMP-1 protein of the present invention for purposes of prokaryote transformation. Prokaryotic hosts may include *E. coli, S. tymphimurium, Serratia marcescens* and *Bacillus subtilis*. Eukaryotic hosts include yeasts such as *Pichia pastoris*, mammalian cells and insect cells.

The term "oligonucleotide", as used herein, is defined as a molecule comprised of two or more ribonucleotides, preferably more than three. Its exact size will depend upon many factors, which, in turn, depend upon the ultimate function and use of the oligonucleotide. The term "primer", as used herein, refers to an oligonucleotide, whether occurring naturally (as in a purified restriction digest) or produced synthetically, and which is capable of initiating synthesis of a strand complementary to a nucleic acid when placed under appropriate conditions, i.e., in the presence of nucleotides and an inducing agent, such as a DNA polymerase, and at a suitable temperature and pH. The primer may be either single-stranded or double-stranded and must be sufficiently long to prime the synthesis of the desired extension product in the presence of the inducing agent. The exact length of the primer will depend upon many factors, including temperature, sequence and/or homology of primer and the method used. For example, in diagnostic applications, the oligonucleotide primer typically contains 15–25 or more nucleotides, depending upon the complexity of the target sequence, although it may contain fewer nucleotides.

The primers herein are selected to be "substantially" complementary to particular target DNA sequences. This means that the primers must be sufficiently complementary to hybridize with their respective strands. Therefore, the primer sequence need not reflect the exact sequence of the template. For example, a non-complementary nucleotide fragment (i.e., containing a restriction site) may be attached to the 5' end of the primer, with the remainder of the primer sequence being complementary to the strand. Alternatively, non-complementary bases or longer sequences can be interspersed into the primer, provided that the primer sequence has sufficient complementary with the sequence to hybridize therewith and form the template for synthesis of the extension product.

The probe to which the DNA of the invention hybridizes preferably consists of a sequence of at least 20 consecutive nucleotides, more preferably 40 nucleotides, even more preferably 50 nucleotides, and most preferably 100 nucleotides or more (up to 100%) of the coding sequence of the nucleotides listed in SEQ ID No. 29 or the complement thereof. Such a probe is useful for detecting expression of PUMP-1 in a cell by a method including the steps of (a) contacting mRNA obtained from the cell with a labeled PUMP-1 hybridization probe; and (b) detecting hybridization of the probe with the mRNA.

As used herein, "substantially pure DNA" means DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence, e.g., a fusion protein. Also included is a recombinant DNA which includes a portion of the nucleotides listed in SEQ ID No. 29 and which encodes an alternative splice variant of PUMP-1.

The DNA may have at least about 70% sequence identity to the coding sequence of the nucleotides listed in SEQ ID No. 29, preferably at least 75% (e.g., at least 80%); and most preferably at least 90%. The identity between two sequences is a direct function of the number of matching or identical positions. When a position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group (GCG), University of Wisconsin Biotechnology Center, 1710 University Avenue, Madison, Wis. 53705).

Further included in this invention are PUMP-1 proteins which are encoded, at least in part, by portions of SEQ ID No. 29, e.g., products of alternative mRNA splicing or alternative protein processing events, or in which a section of PUMP-1 sequence has been deleted. The fragment, or the intact PUMP-1 polypeptide, may be covalently linked to another polypeptide, e.g., one which acts as a label, a ligand or a means to increase antigenicity.

A substantially pure PUMP-1 protein may be obtained, for example, by extraction from a natural source; by expression of a recombinant nucleic acid encoding a PUMP-1 polypeptide; or by chemically synthesizing the protein. Purity can be measured by any appropriate method, e.g., column chromatography, such as immunoaffinity chromatography using an antibody specific for PUMP-1, polyacrylamide gel electrophoresis, or HPLC analysis. A protein is substantially free of naturally associated components when it is separated from at least some of those contaminants which accompany it in its natural state. Thus, a protein which is chemically synthesized or produced in a cellular system different from the cell from which it naturally originates will be, by definition, substantially free from its naturally associated components. Accordingly, substantially pure proteins include eukaryotic proteins synthesized in *E. coli*, other prokaryotes, or any other organism in which they do not naturally occur.

In addition to substantially full-length proteins, the invention also includes fragments (e.g., antigenic fragments) of the PUMP-1 protein. As used herein, "fragment," as applied to a polypeptide, will ordinarily be at least 10 residues, more typically at least 20 residues, and preferably at least 30 (e.g., 50) residues in length, but less than the entire, intact sequence. Fragments of the PUMP-1 protein can be generated by methods known to those skilled in the art, e.g., by enzymatic digestion of naturally occurring or recombinant PUMP-1 protein, by recombinant DNA techniques using an expression vector that encodes a defined fragment of PUMP-1, or by chemical synthesis. The ability of a candidate fragment to exhibit a characteristic of PUMP-1 (e.g., binding to an antibody specific for PUMP-1) can be assessed by methods known in the art. Purified PUMP-1 or antigenic fragments of PUMP-1 can be used to generate new antibodies or to test existing antibodies (e.g., as positive controls in a diagnostic assay) by employing standard protocols known to those skilled in the art. Included in this invention is polyclonal antisera generated by using PUMP-1 or a fragment of PUMP-1 as the immunogen in, e.g., rabbits. Standard protocols for monoclonal and polyclonal antibody production known to those skilled in this art are employed. The monoclonal antibodies generated by this procedure can be screened for the ability to identify recombinant PUMP-1 cDNA clones, and to distinguish them from other cDNA clones.

The invention encompasses not only an intact anti-PUMP-1 monoclonal antibody, but also an immunologically-active antibody fragment, e.g., a Fab or (Fab)$_2$ fragment; an engineered single chain Fv molecule; or a chimeric molecule, e.g., an antibody which contains the binding specificity of one antibody, e.g., of murine origin, and the remaining portions of another antibody, e.g., of human origin.

In one embodiment, the antibody, or a fragment thereof, may be linked to a toxin or to a detectable label, e.g., a radioactive label, non-radioactive isotopic label, fluorescent label, chemiluminescent label, paramagnetic label, enzyme label, or colorimetric label. Examples of suitable toxins include diphtheria toxin, Pseudomonas exotoxin A, ricin, and cholera toxin. Examples of suitable enzyme labels include malate hydrogenase, staphylococcal nuclease, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholinesterase, etc. Examples of suitable radioisotopic labels include $^3$H, $^{125}$I, $^{131}$I, $^{32}$P, $^{35}$S, $^{14}$C, etc.

Paramagnetic isotopes for purposes of in vivo diagnosis can also be used according to the methods of this invention. There are numerous examples of elements that are useful in magnetic resonance imaging. For discussions on in vivo nuclear magnetic resonance imaging, see, for example, Schaefer et al., (1989) *JACC* 14, 472–480; Shreve et al., (1986) *Magn. Reson. Med.* 3, 336–340; Wolf, G. L., (1984) *Physiol. Chem. Phys. Med. NMR* 16, 93–95; Wesbey et al., (1984) *Physiol. Chem. Phys. Med. NMR* 16, 145–155; Runge et al., (1984) *Invest. Radiol.* 19, 408–415. Examples of suitable fluorescent labels include a fluorescein label, an isothiocyalate label, a rhodamine label, a phycoerythrin label, a phycocyanin label, an allophycocyanin label, an ophthaldehyde label, a fluorescamine label, etc. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known and used by those of ordinary skill in the art. Typical techniques are described by Kennedy et al., (1976) *Clin. Chim. Acta* 70, 1–31; and Schurs et al., (1977) *Clin. Chim. Acta* 81, 1–40. Coupling techniques mentioned in the latter are the glutaraldehyde method, the periodate method, the dimaleimide method, the m-maleimidobenzyl-N-hydroxy-succinimide ester method. All of these methods are incorporated by reference herein.

Also within the invention is a method of detecting PUMP-1 protein in a biological sample, which includes the steps of contacting the sample with the labeled antibody, e.g., radioactively tagged antibody specific for PUMP-1, and determining whether the antibody binds to a component of the sample. Antibodies to the PUMP-1 protein can be used in an immunoassay to detect increased levels of PUMP-1 protein expression in tissues suspected of neoplastic transformation. These same uses can be achieved with Northern blot assays and analyses.

As described herein, the invention provides a number of diagnostic advantages and uses. For example, the PUMP-1 protein is useful in diagnosing cancer in different tissues since this protein is highly overexpressed in tumor cells. Antibodies (or antigen-binding fragments thereof) which bind to an epitope specific for PUMP-1 are useful in a method of detecting PUMP-1 protein in a biological sample for diagnosis of cancerous or neoplastic transformation. This method includes the steps of obtaining a biological sample (e.g., cells, blood, plasma, tissue, etc.) from a patient suspected of having cancer, contacting the sample with a labeled antibody (e.g., radioactively tagged antibody) specific for PUMP-1, and detecting the PUMP-1 protein using standard immunoassay techniques such as an ELISA. Antibody binding to the biological sample indicates that the sample contains a component which specifically binds to an epitope within PUMP-1.

Likewise, a standard Northern blot assay can be used to ascertain the relative amounts of PUMP-1 mRNA in a cell or tissue obtained from a patient suspected of having cancer, in accordance with conventional Northern hybridization techniques known to those of ordinary skill in the art. This Northern assay uses a hybridization probe, e.g., radiolabelled PUMP-1 cDNA, either containing the full-length, single stranded DNA having a sequence complementary to SEQ ID No. 29, or a fragment of that DNA sequence at least 20 (preferably at least 30, more preferably at least 50, and most preferably at least 100 consecutive nucleotides in length). The DNA hybridization probe can be labeled by any of the many different methods known to those skilled in this art.

The following examples are given for the purpose of illustrating various embodiments of the invention and are not meant to limit the present invention in any fashion:

EXAMPLE 1

Amplification of Serine Proteases Using Redundant and Specific Primers

Only cDNA preparations deemed free of genomic DNA were used for gene expression analysis. Redundant primers were prepared for serine proteases, metallo-proteases and cysteine protease. The primers were synthesized to consensus sequences of amino acid surrounding the catalytic triad for serine proteases, viz. histidine . . . aspartate . . . and serine. The sequences of both sense (histidine & aspartate) and antisense (aspartate and serine) redundant primers are shown in Table 2.

Several protease entities were identified and subcloned from PCR amplification of cDNA derived from serous cystadenocarcinomas. Therefore, the proteases described herein are reflective of surface activities for this type of carcinoma, the most common form of ovarian cancer. Applicant also shows PCR amplification bands of similar base pair size unique to the mucinous tumor type and the clear cell type. About 20–25% of ovarian cancers are classified as either mucinous, clear cell, or endometrioid.

To determine the identity of the PCR products, all the appropriate bands were ligated into Promega T-vector plasmid and the ligation product was used to transform JM109 cells (Promega) grown on selective media. After selection and culturing of individual colonies, plasmid DNA was isolated by means of the WIZARD MINIPREP™ DNA purification system (Promega). Inserts were sequenced using a Prism Ready Reaction Dydeoxy Terminators cycle sequencing kit (Applied Biosystems). Residual dye terminators were removed from the completed sequencing reaction using a CENTRISEP SPIN™ column (Princeton Separation), and samples were loaded into an Applied Biosystems Model 373A DNA sequencing system. The results of subcloning and sequencing for the serine protease primers are summarized in Table 3.

TABLE 2

PCR Primers

| | | 5'→3' | SEQ ID No. |
|---|---|---|---|
| Redundant Primers: | | | |
| Serine Protease (histidine) = S1 | | tgggtigtiacigcigcica(ct)t | 1 |
| Serine Protease (aspartic acid) = AS1 | | a(ag)ia(ag)igciatitcitticc | 2 |
| Serine Protease (serine) = AS11 | | a(ag)iggiccicci(cg)(ta)(ag)tcicc | 3 |
| Cysteine Protease - sense | | ca(ag)ggica(ag)tg(ct)ggi(ta)(cg)itg(ct)tgg | 4 |
| Cysteine Protease - antisense | | taiccicc(ag)tt(ag)caicc(ct)tc | 5 |
| Metallo Protease - sense | | cci(ac)gitg(tc)ggi(ga)(ta)icciga | 6 |
| Metallo Protease - antisense | | tt(ag)tgicciai(ct)tc(ag)tg | 7 |
| Specific Primers: | | | |
| Serine Protease (hepsin) | = sense | tgtcccgatggcgagtgttt | 8 |
| Serine Protease (hepsin) | = antisense | cctgttggccatagtactgc | 9 |
| Serine Protease (SCCE) | = sense | agatgaatgagtacaccgtg | 10 |
| Serine Protease (SCCE) | = antisense | ccagtaagtccttgtaaacc | 11 |
| Serine Protease (Comp B) | = sense | aagggacacgagagctgtat | 12 |
| Serine Protease (Comp B) | = antisense | aagtggtagttggaggaagc | 13 |
| Serine Protease (Protease M) | = sense | ctgtgatccaccctgactat | 20 |
| Serine Protease (Protease M) | = antisense | caggtggatgtatgcacact | 21 |
| Serine Protease (TADG12) | = sense (Ser10-s) | gcgcactgtgtttatgagat | 22 |
| Serine Protease (TADG12) | = antisense (Ser10-as) | ctctttggcttgtacttgct | 23 |
| Serine Protease (TADG13) | = sense | tgagggacatcattatgcac | 24 |
| Serine Protease (TADG13) | = antisense | caagttttccccataattgg | 25 |
| Serine Protease (TADG14) | = sense | acagtacgcctgggagacca | 26 |
| Serine Protease (TADG14) | = antisense | ctgagacggtgcaattctgg | 27 |
| Cysteine Protease (Cath-L) | = sense | attggagagagaaaggctac | 14 |
| Cysteine Protease (Cath-L) | = antisense | cttgggattgtacttacagg | 15 |
| Metallo Protease (PUMP1) | = sense | cttccaaagtggtcacctac | 16 |
| Metallo Protease (PUMP1) | = antisense | ctagactgctaccatccgtc | 17 |

TABLE 3

Serine protease candidates

| | Primer Set | Gene Candidate |
|---|---|---|
| Subclone | | |
| 1 | His-Ser | hepsin |
| 2 | His-Ser | SCCE |
| 3 | His-Ser | |
| Compliment B | | |
| 4 | His-Asp | Cofactor 1 |
| 5 | His-Asp | TADG-12* |
| 6 | His-Ser | TADG-13* |
| 7 | His-Ser | TADG-14* |
| 8 | His-Ser | Protease M |
| 9 | His-Ser | TADG-15* |

*indicates novel proteases

Sequencing of the PCR products derived from tumor cDNA confirms the potential candidacy of these genes. The three novel genes all have conserved residues within the catalytic triad sequence consistent with their membership in the serine protease family.

Applicant compared the PCR products amplified from normal and carcinoma cDNAs using sense-histidine and antisense-aspartate as well as sense-histidine and antisense-serine. The anticipated PCR products of approximately 200 bp and 500 bp for those pairs of primers were observed (aspartate is approximately 50–70 amino acids downstream from histidine, and serine is about 100–150 amino acids toward the carboxy end from histidine).

FIG. 1 shows a comparison of PCR products derived from normal and carcinoma cDNA as shown by staining in an agarose gel. Two distinct bands in Lane 2 were present in the primer pair sense-His/antisense ASP (AS1) and multiple bands of about 500 bp are noted in the carcinoma lane for the sense-His/antisense-Ser (AS2) primer pairs in Lane 4.

EXAMPLE 2
Northern Blots Analysis

Significant information can be obtained by examining the expression of these candidate genes by Northern blot. Analysis of normal adult multi-tissue blots offers the opportunity to identify normal tissues which may express the protease. Ultimately, if strategies for inhibition of proteases for therapeutic intervention are to be developed, it is essential to appreciate the expression of these genes in normal tissues.

Significant information is expected from Northern blot analysis of fetal tissue. Genes overexpressed in carcinomas are often highly expressed in organogenesis. As indicated, the hepsin gene cloned from hepatoma cells and overexpressed in ovarian carcinoma is overtly expressed in fetal liver. Hepsin gene expression was also detected in fetal kidney, and therefore, could be a candidate for expression in renal carcinomas.

Northern panels for examining expression of genes in a multi-tissue normal adult as well as fetal tissue are commercially available (CLONTECH). Such evaluation tools are not only important to confirm the overexpression of individual transcripts in tumor versus normal tissues, but also provides the opportunity to confirm transcript size, and to determine if alternate splicing or other transcript alteration may occur in ovarian carcinoma.

Northern blot analysis was performed as follows: 10 μg of mRNA was loaded onto a 1% formaldehyde-agarose gel, electrophoresed and blotted onto a HyBond-N+™ nylon membrane (Amersham). $^{32}$P-labeled cDNA probes were made using Prime-a-Gene Labeling System™ (Promega). The PCR products amplified by specific primers were used as probes. Blots were prehybridized for 30 min and then hybridized for 60 min at 68° C. with $^2$P-labeled cDNA probe in ExpressHyb™ Hybridization Solution (CLONTECH). Control hybridization to determine relative gel loading was accomplished using the β-tubulin probe.

Normal human tissues including spleen, thymus, prostate, testis, ovary, small intestine, colon, peripheral blood leukocyte, heart, brain, placenta, lung, liver, skeletal muscle, kidney, pancreas and normal human fetal tissues (Human Multiple Tissue Northern Blot; CLONTECH) were all examined using the same hybridization procedure.

Figure 2:
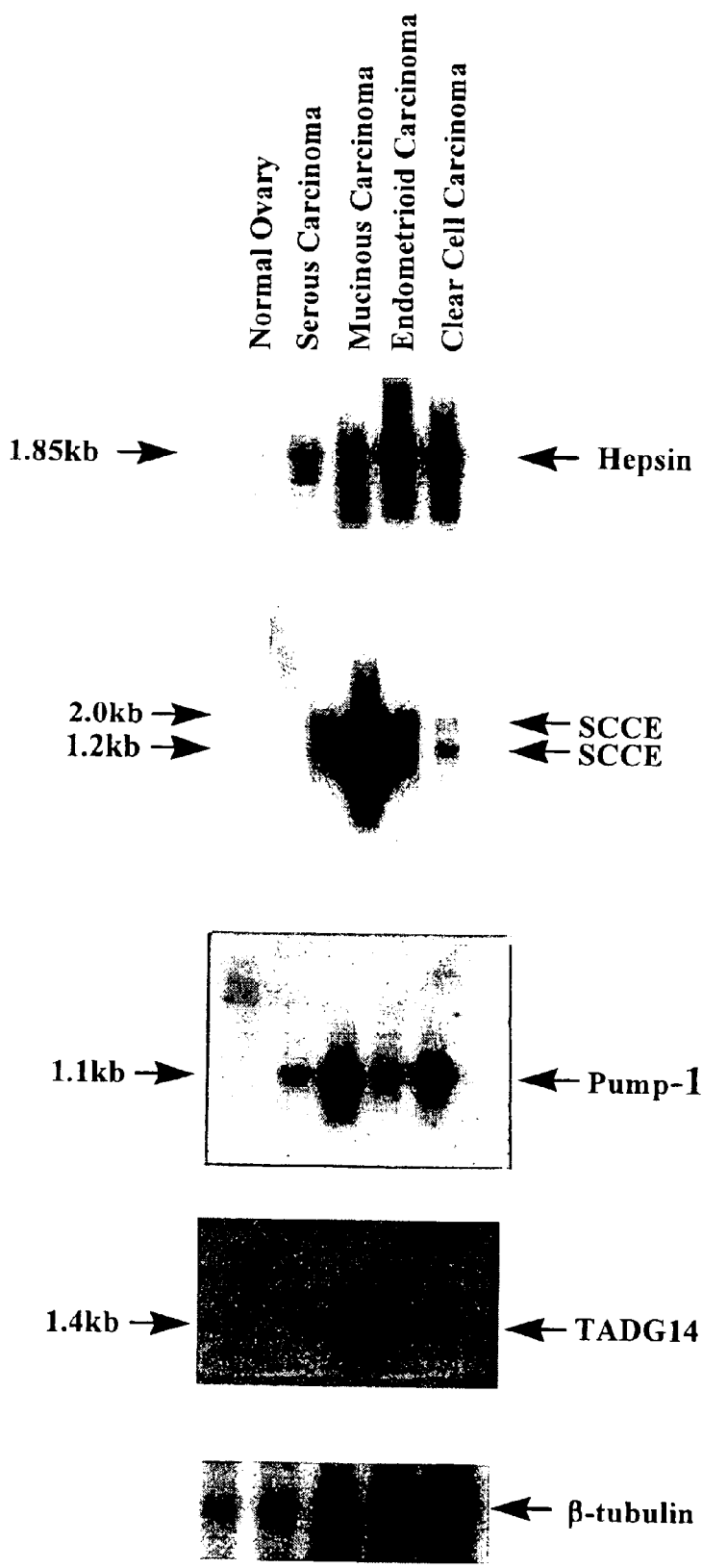
FIG. 2 shows Northern blot analysis of ovarian tumors using hepsin, SCCE, PUMP-1, TADG-14 and β-tubulin probes.

Experiments comparing PCR amplification in normal ovary and ovarian carcinoma suggested overexpression and/or alteration in mRNA transcript in tumor tissues. Northern blot analysis of TADG-14 confirms a transcript size of 1.4 kb and data indicate overexpression in ovarian carcinoma (FIG. 2). Isolation and purification using both PCR and a specific 250 bp PCR product to screen positive plaques yielded a 1.2 kb clone of TADG-14. Other proteases were amplified by the same method using the appropriate primers from Table 2.

EXAMPLE 3
PCR Products Corresponding to Serine, Cysteine and Metallo-Proteases

Figure 3:
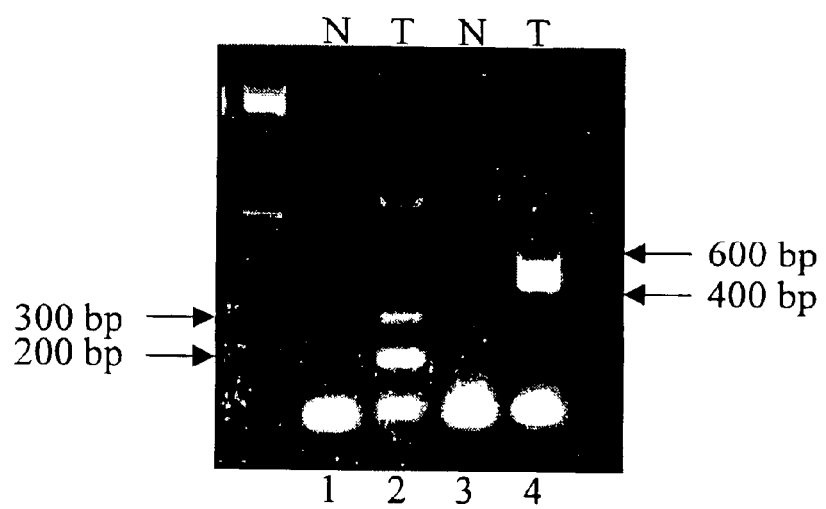
FIG. 3 shows amplification with serine protease redundant primers: histidine sense (S1) with aspartic acid antisense (AS1), using normal cDNA (Lane 1) and tumor cDNA (Lane 2); and histidine sense (S1) with serine antisense (AS2), using normal cDNA (Lane 3) and tumor cDNA (Lane 4).
Figure 4:
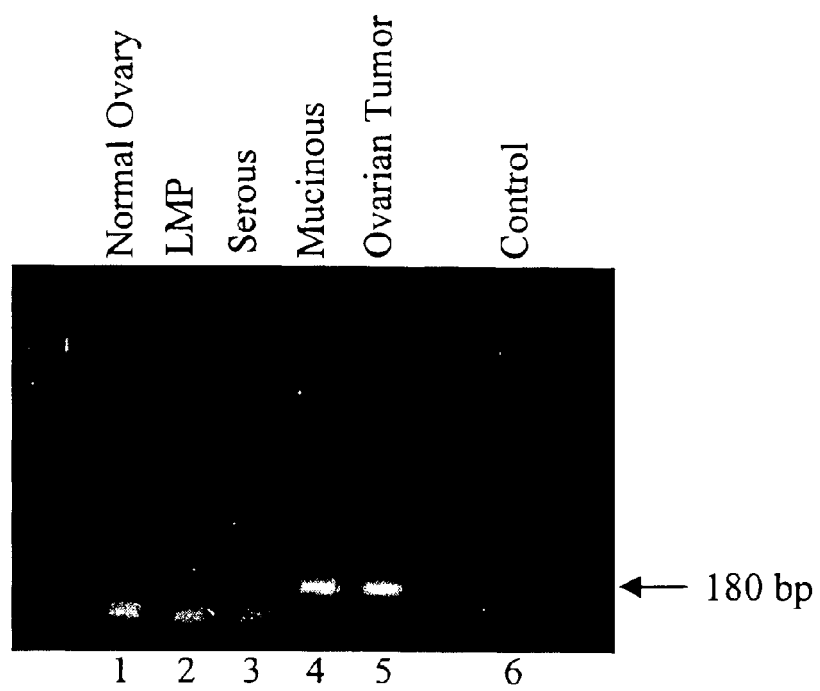
FIG. 4 shows amplification with cysteine protease redundant primers. Normal (Lane 1), low malignant potential (Lane 2), serious carcinoma (Lane 3), mucinous carcinoma (Lane 4), and clear cell carcinoma (Lane 5).
Figure 5:
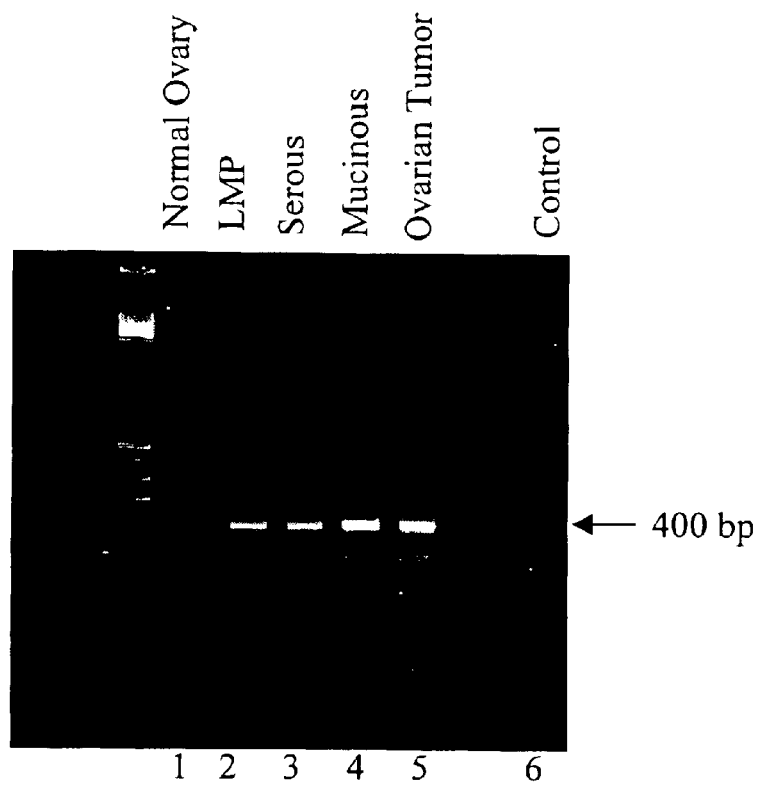
FIG. 5 shows amplification with metallo-protease redundant primers. Normal (Lane 1), low malignant potential (Lane 2), serious carcinoma (Lane 3), mucinous carcinoma (Lane 4), and clear cell carcinoma (Lane 5).
Figure 6:
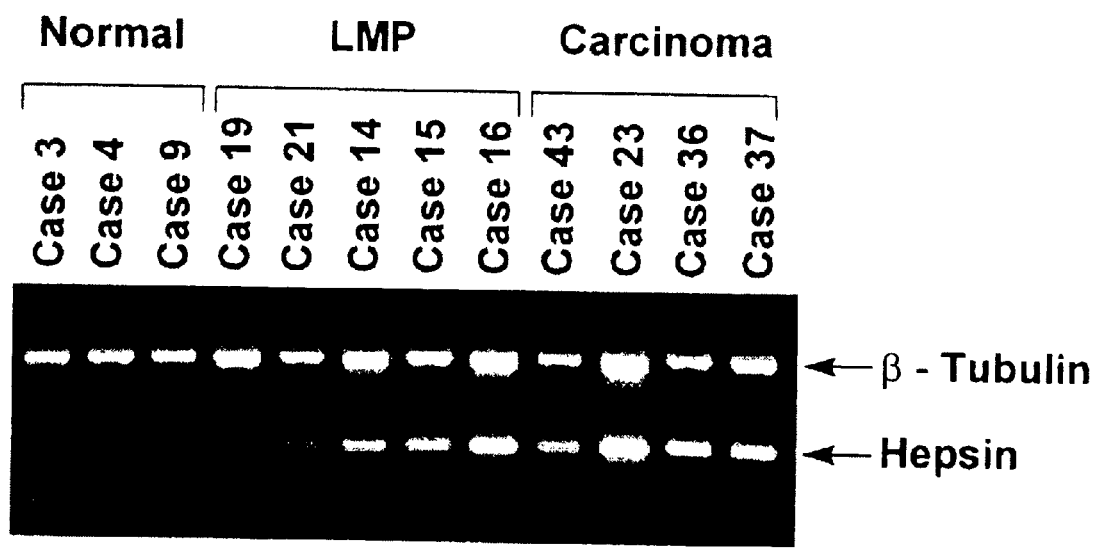
FIG. 6 shows amplification with specific primers directed towards the serine protease, hepsin. Expression in normal (Lanes 1–3), low malignant potential tumors (Lanes 4–8), and ovarian carcinomas (Lanes 9–12).
Figure 7:
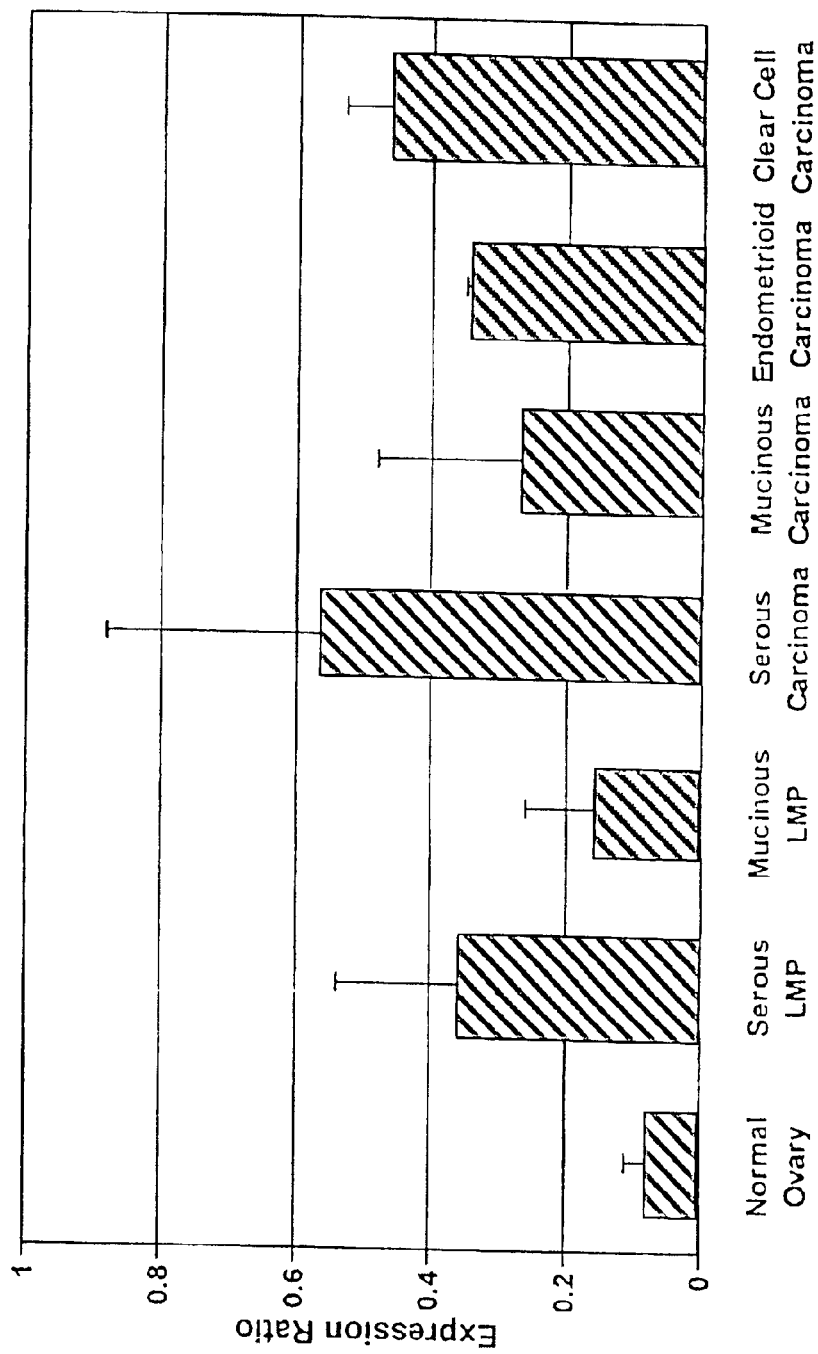
FIG. 7 shows hepsin expression levels in normal, low malignant potential tumors, and ovarian carcinomas. S=serious, M=mucinous, LMP=low malignant potential.
Figure 8:
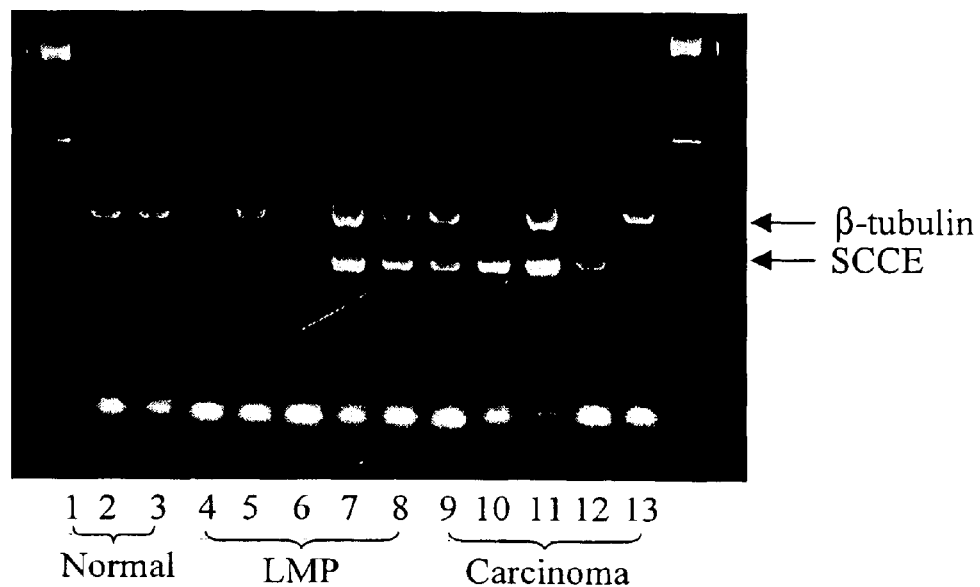
FIG. 8 shows serine protease stratum corneum chymotrypsin enzyme (SCCE) expression in normal, low malignant potential tumors, and ovarian carcinomas.
Figure 9:
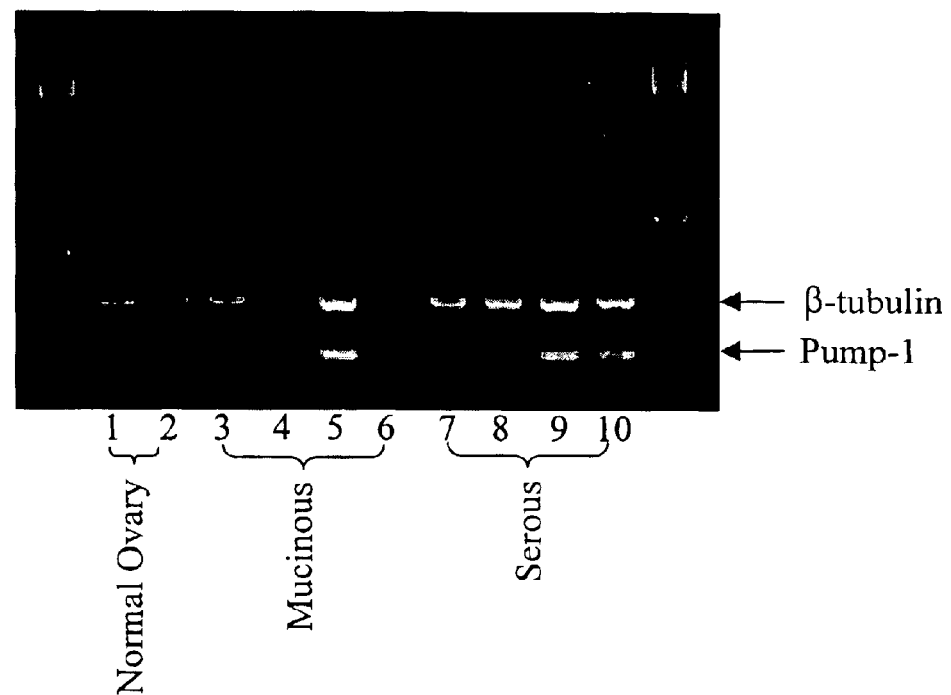
FIG. 9 shows metallo-protease PUMP-1 (MMP-7) gene expression in normal (lanes 1–2) and ovarian carcinomas tissue (Lanes 3–10).

Based on their unique expression in either low malignant potential tumors or carcinomas, PCR-amplified cDNA products were cloned and sequenced and the appropriate gene identified based upon nucleotide and amino acid sequences stored in the GCG and EST databases. FIGS. 3, 4 & 5 show the PCR product displays comparing normal and carcinomatous tissues using redundant primers for serine proteases (FIG. 3), for cysteine proteases (FIG. 4) and for metallo-proteases (FIG. 5). Note the differential expression in the carcinoma tissues versus the normal tissues. The proteases were identified using redundant cDNA primers (see Table 2) directed towards conserved sequences that are associated with intrinsic enzyme activity (for serine proteases, cysteine proteases and metallo-proteases) by comparing mRNA expression in normal, low malignant potential and overt ovarian carcinoma tissues according to Sakanari et al. [*Biochemistry* 86, 4863–4867 (1989)].

EXAMPLE 4
Serine Proteases

For the serine protease group, using the histidine domain primer sense, S1, in combination with antisense primer AS2, the following proteases were identified:

(a) Hepsin, a trypsin-like serine protease cloned from hepatoma cells shown to be a cell surface protease essential for the growth of hepatoma cells in culture and highly expressed in hepatoma tumor cells (FIG. 3, lane 4);

(b) Complement factor B protease (human factor IX), a protease involved in the coagulation cascade and associated with the production and accumulation of fibrin split products associated with tumor cells (FIG. 3, lane 4). Compliment factor B belongs in the family of coagulation factors X (Christmas factor). As part of the intrinsic pathway, compliment factor B catalyzes the proteolytic activation of coagulation factor X in the presence of $Ca^{2+}$ phospholipid and factor VIIIa e5; and (c) A stratum corneum chymotryptic enzyme (SCCE) serine protease involved in desquarnation of skin cells from the human stratum corneum (FIG. 3, lane 4).

SCCE is expressed in keratinocytes of the epidermis and functions to degrade the cohesive structures in the cornified layer to allow continuous skin surface shedding.

EXAMPLE 5
Cysteine Proteases

In the cysteine protease group, using redundant sense and anti-sense primers for cysteine proteases, one unique PCR product was identified by overexpression in ovarian carcinoma when compared to normal ovarian tissue (FIG. 4, lanes 3–5). Cloning and sequencing this PCR product identified a sequence of Cathepsin L, which is a lysomal cysteine protease whose expression and secretion is induced by malignant transformation, growth factors and tumor promoters. Many human tumors (including ovarian) express high levels of Cathepsin L. Cathepsin L cysteine protease belongs in the stromolysin family and has potent elastase and collagenase activities. Published data indicates increased levels in the serum of patients with mucinous cystadenocarcinoma of the ovary. It has not heretofore been shown to be expressed in other ovarian tumors.

EXAMPLE 6
Metallo-Proteases

Using redundant sense and anti-sense primers for the metallo-protease group, one unique PCR product was detected in the tumor tissue which was absent in normal ovarian tissue (FIG. 5, lanes 2–5). Subcloning and sequencing this product indicates it has complete homology in the appropriate region with the so-called PUMP-1 (MMP-7) gene. This zinc-binding metallo-protease is expressed as a proenzyme with a signal sequence and is active in gelatin and collagenase digestion. PUMP-1 has also been shown to be induced and overexpressed in 9 of 10 colorectal carcinomas compared to normal colon tissue, suggesting a role for this substrate in the progression of this disease.

EXAMPLE 7
Expression of PUMP-1

Using redundant primers to metal binding domains and conserved histidine domains, a differentially expressed PCR product identical to matrix metallo-protease 7 (MMP-7) was identified, herein called PUMP-1. Using specific primers for PUMP-1, PCR produced a 250 bp product for Northern blot analysis.

The mRNA overexpression of PUMP-1 was detected and determined using quantitative PCR. Quantitative PCR was performed generally according to the method of Noonan et al. [*Proc. Natl. Acad. Sci., USA,* 87:7160–7164 (1990)]. The following oligonucleotide primers were used:

PUMP-1 forward 5'-CTTCCAAAGTGGTCACCTAC-3' (SEQ ID No. 16), and PUMP-1 reverse 5'-CTAGACTGCTACCATCCGTC-3' (SEQ ID No. 17); and β-tubulin forward 5'-TGCATTGACAACGAGGC-3' (SEQ ID No. 18), and β-tubulin reverse 5'-CTGTCTTGA CATTGTTG-3' (SEQ ID No. 19).

β-tubulin was utilized as an internal control. The predicted sizes of the amplified genes were 250 bp for PUMP-1 and 454 bp for β-tubulin. The primer sequences used in this study were designed according to the cDNA sequences described by Leytus et al. [*Biochemistry,* 27, 1067–1074 (1988)] for PUMP-1, and Hall et al. [*Mol. Cell. Biol.,* 3, 854–862 (1983)] for β-tubulin.

The PCR reaction mixture consisted of cDNA derived from 50 ng of mRNA converted by conventional techniques, 5 pmol of sense and antisense primers for both the PUMP-1 gene and the β-tubulin gene, 200 μmol of dNTPs, 5 μCi of α-³²PdCTP and 0.25 units of Taq DNA polymerase with reaction buffer (Promega) in a final volume of 25 μl.

The target sequences were amplified in parallel with the β-tubulin gene. Thirty cycles of PCR were carried out in a Thermal Cycler (Perkin-Elmer Cetus). Each cycle of PCR included 30 sec of denaturation at 95° C., 30 sec of annealing at 63° C. and 30 sec of extension at 72° C. The PCR products were separated on 2% agarose gels and the radioactivity of each PCR product was determined by using a PhosphorImager™ (Molecular Dynamics). Student's t test was used for comparison of mean values.

Figures 17A, 17B, 17C:
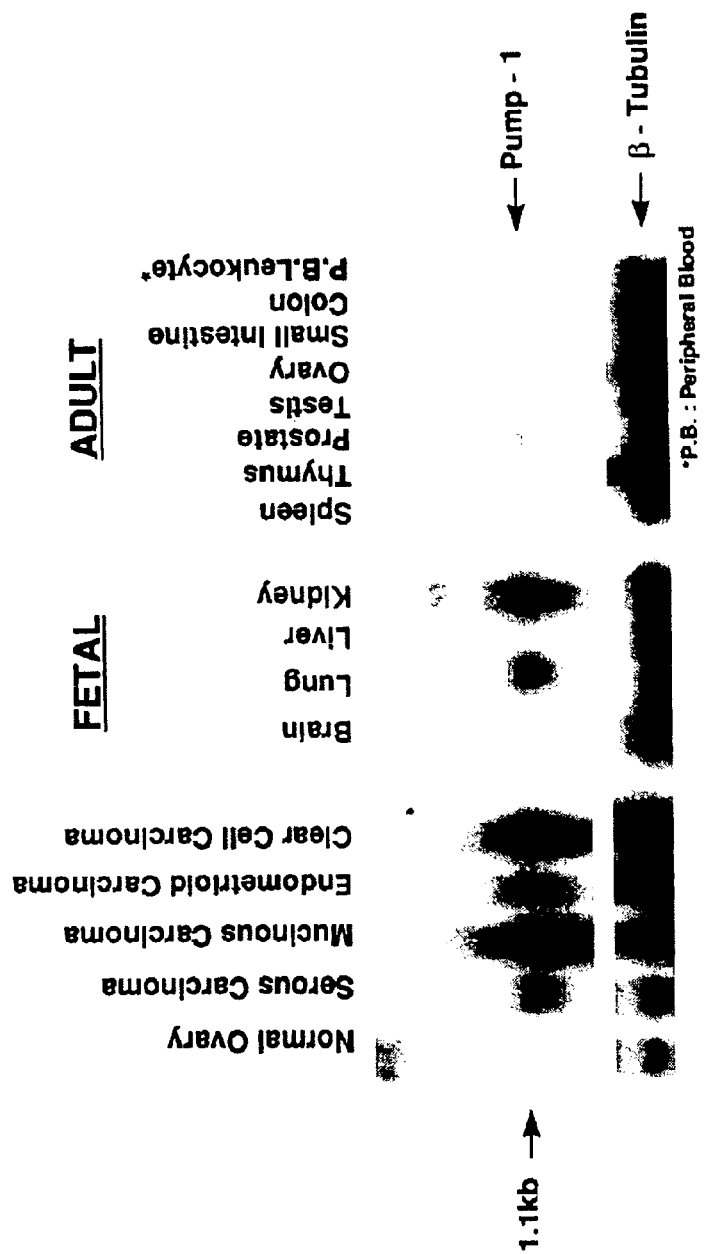
FIG. 17A shows Northern blot analysis of PUMP-1 mRNA from normal ovary and ovarian carcinomas. Lane 1, normal ovary; lane 2, serous carcinoma; lane 3, mucinous carcinoma; lane 4, endometrioid carcinoma; lane 5, clear cell carcinoma. PUMP-1 transcripts are detected only in carcinoma cases (lanes 2–5).
FIG. 17B shows that among normal human fetal tissues, fetal lung and fetal kidney show increased transcript.
FIG. 17C shows that PUMP-1 overexpression is not observed in normal human adult tissues. Slight expression above the background level is observed in the prostate.

To confirm the results of quantitative PCR and to identify the appropriate transcript size for PUMP-1, Northern blot hybridization was performed using representative samples of each histological type of carcinoma. As shown in FIG. 17A, Northern blot hybridization with a ³²P-labeled PUMP-1 probe revealed an intense band in carcinoma cases and no visible band in normal ovary. The size of the PUMP-1 transcript in carcinoma cases was approximately 1.1 Kb. Among normal human fetal tissues examined, fetal lung and fetal kidney showed increased transcript expression (FIG. 17B), on the other hand, PUMP-1 expression was not observed or was expressed at very low levels in normal human adult tissues, including spleen, thymus, prostate, testis, ovary, small intestine, colon and peripheral blood leukocyte (FIG. 17C).

Figure 18A:
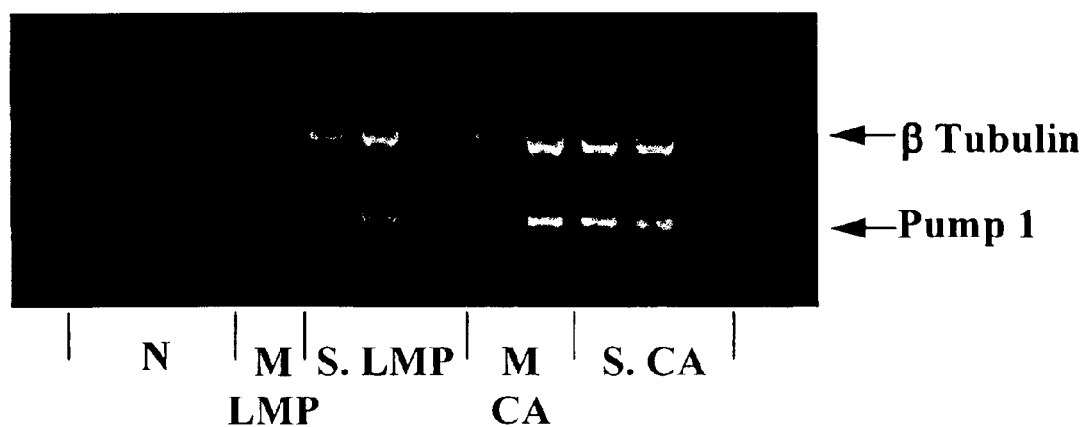
FIG. 18A shows quantitative PCR analysis of PUMP-1 expression. Cases 3, 4 an d9 are normal ovaries. Cases 19, 21, 14, 15 and 16 are LMP tumors. Cases 43, 23, 36 and 37 are ovarian carcinomas. Expression levels of PUMP-1 relative to β-tubulin are significantly elevated in 8 or 9 tumor cases compared to that or normal ovaries.
Figure 18B:
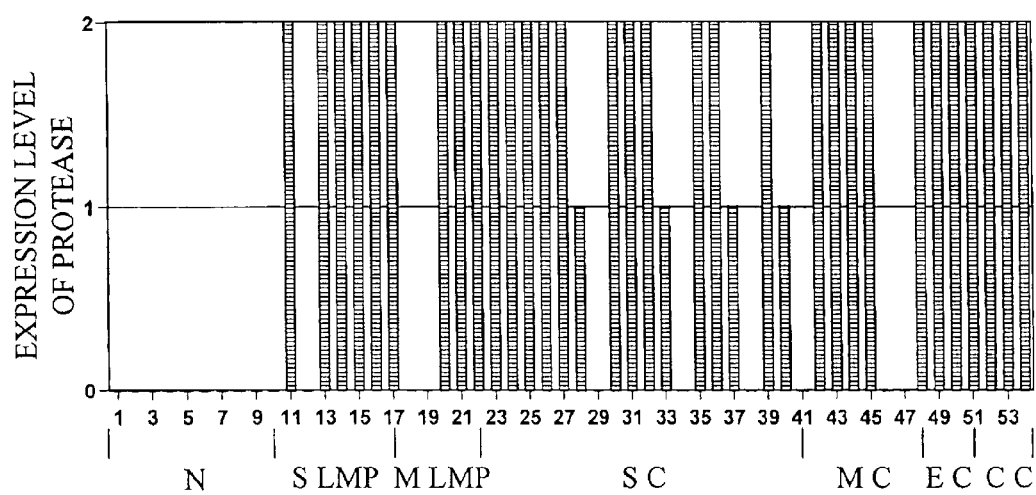
FIG. 18B shows the ratio of mRNA expression of PUMP-1 compared to the internal control β-tubulin in 10 normal and 44 ovarian carcinomas.
Figure 19:
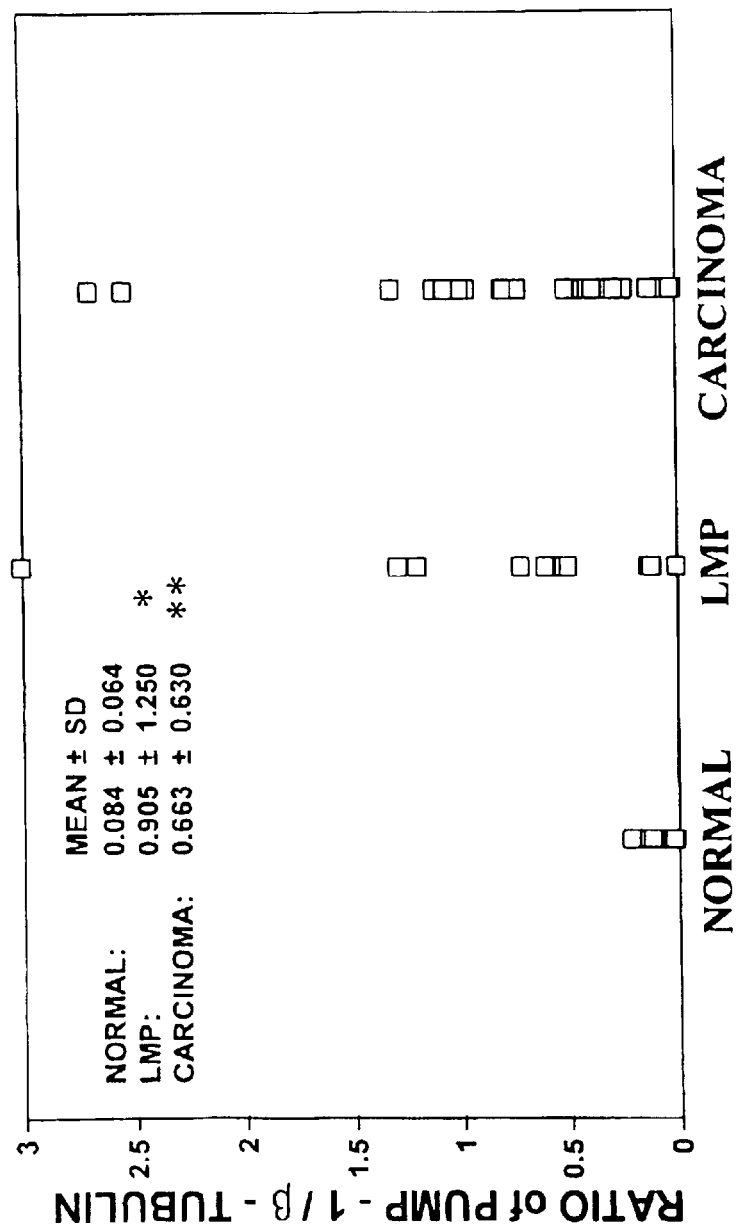
FIG. 19 shows the ratio of PUMP-1 expression to expression of β-tubulin in normal ovary, LMP tumors and ovarian carcinomas. PUMP-1 mRNA expression levels were significantly elevated in LMP tumor (p<0.05) and carcinoma (p<0.0001) compared to that in normal ovary. All 10 samples of individual normal ovary showed low levels of PUMP-1 expression.

Quantitative PCR comparing normal versus ovarian carcinoma expression of the PUMP-1 mRNA indicates that this gene is highly expressed in serous carcinomas, including most low malignant serous tumors, and is, again, expressed to a lesser extent in mucinous tumors (see FIGS. 18A & 18B). PUMP-1, however, is so far the protease most frequently found overexpressed in mucinous tumors (See Table 8).

A tumor tissue bank of fresh frozen tissue of ovarian carcinomas as shown in Table 4 was used for evaluation. Approximately 100 normal ovaries removed for medical reasons other than malignancy were obtained from surgery and were available as controls.

From the tumor bank, approximately 100 carcinomas were evaluated encompassing most histological sub-types of ovarian carcinoma, including borderline or low-malignant potential tumors and overt carcinomas. The approach included using mRNA prepared from fresh frozen tissue (both normal and malignant) to compare expression of genes in normal, low malignant potential tumors and overt carcinomas. The cDNA prepared from polyA⁺ mRNA was deemed to be genomic DNA-free by checking all preparations with primers that encompassed a known intron-exon splice site using both β-tubulin and p53 primers.

TABLE 4

| Ovarian cancer tissue bank | | | | |
|---|---|---|---|---|
| Stage | Total | Stage I/II | Stage III/IV | No |
| Serous | | | | |
| Malignant | 166 | 15 | 140 | 8 |
| LMP | 16 | 9 | 7 | 0 |
| Benign | 12 | 0 | 0 | 12 |
| Mucinous | | | | |
| Malignant | 26 | 6 | 14 | 6 |
| LMP | 28 | 25 | 3 | 0 |
| Benign | 3 | 0 | 0 | 3 |

TABLE 4-continued

| Ovarian cancer tissue bank | | | | |
|---|---|---|---|---|
| Stage | Total | Stage I/II | Stage III/IV | No |
| Endometrioid | | | | |
| Malignant | 38 | 17 | 21 | 0 |
| LMP | 2 | 2 | 0 | 0 |
| Benign | 0 | 0 | 0 | 0 |
| Other* | | | | |
| Malignant | 61 | 23 | 29 | 9 |
| LMP | 0 | 0 | 0 | 0 |
| Benign | 5 | 0 | 0 | 5 |

*Other category includes tumor types: Brenner's tumor, thecoma, teratoma, fibrothecoma, fibroma, granulosa cell, clear cell, germ cell, mixed mullerian, stromal, undifferentiated, and dysgerminoma.

The expression of the metallo-protease PUMP-1 gene in 10 normal ovaries, 12 low malignant potential (LMP) tumors, and 32 ovarian carcinoma (both mucinous and serous type) by quantitative PCR using PUMP-1-specific primers (see Table 2) was determined (primers directed toward the β-tubulin message were used as an internal standard) (Table 5). Using a cut-off level for overexpression of the mean for normal ovary +2SD, 9 of 12 LMP (75%) tumor cases and 26 of 32 (81%) carcinoma cases were above the cut-off value. PUMP-1 mRNA expression was significantly elevated in tumors compared to that in normal ovary for both LMP tumor (p<0.05) and carcinoma (p<0.0001). All 10 cases of normal ovaries showed relatively low levels of PUMP-1 mRNA expression.

Table 5 summarizes the data obtained on the histological type, stage, grade and mRNA overexpression of PUMP-1 in all the cases studied. Lymph node metastases were histopathologically proven in 5 cases and all these cases showed overexpression of PUMP-1. Also of note, all 5 cases of stage I carcinoma showed overexpression of PUMP-1. Overall, the expression ratio (mean±SD) for normal ovary was determined to be 0.084±0.065; for LMP tumors, 0.905±1.251; and for carcinomas, 0.663±0.630 (Table 6). From a histological point of view (Table 6), overexpression of PUMP-1 was observed in 21 of 26 (80.8%) serous tumors (6 of 7 LMP tumors and 15 of 19 carcinomas) and 8 of 12 (66.7%) mucinous tumors (3 of 5 LMP tumors and 5 of 7 carcinomas). For endometrioid and clear cell carcinomas, PUMP-1 was found to be overexpressed in all 6 cases examined.

Figure 20A:
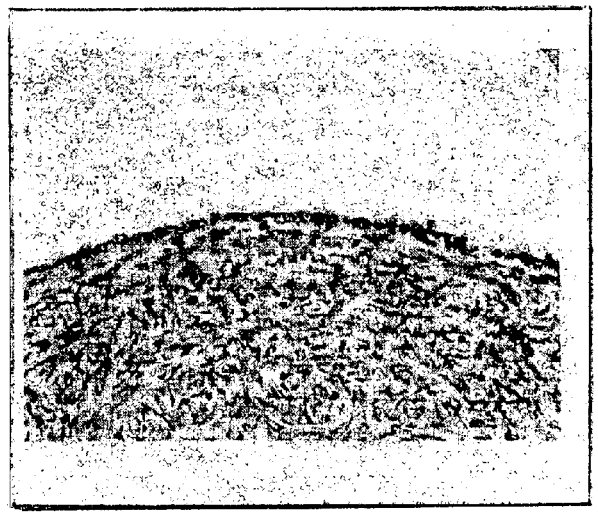
FIG. 20A shows normal ovarian epithelium shows no PUMP-1 immunoreactivity (x20).
Figure 20B:
FIG. 20B shows intense staining of secretory vessels in mucinous tumors (x20).
Figure 20C:
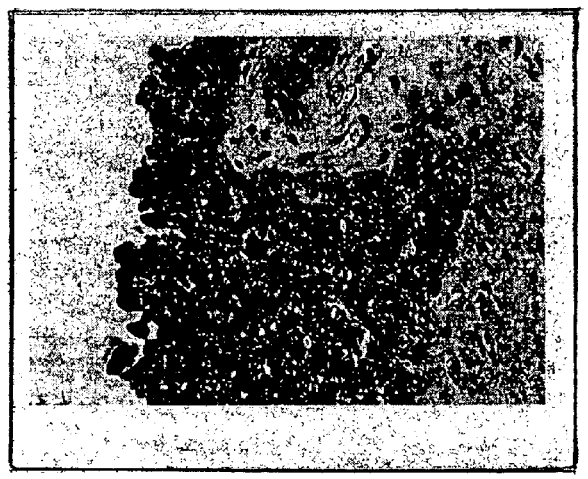
FIG. 20C shows cytoplasmic staining of PUMP-1 in serous tumors (x20).
Figure 20D:
FIG. 20D shows clear cell tumors (x100).
Figure 20E:
FIG. 20E shows secretion of PUMP-1 to the extracellular environment of endometrioid tumors (x100).

Examination of PUMP-1 antigen expression in normal and carcinomatous tissues by immunolocalization using both a peptide derived polyclonal antibody and a commercial monoclonal antibody (Calbiochem) confirmed the quantitative PCR data (Table 7). Little or no staining was observed in normal ovary (FIG. 20A), while intense tumor cell staining of secretory bodies could be detected in several mucinous tumors (e.g., FIG. 20B). Intense cytoplasmic staining was also observed in serous tumors (FIG. 20C), clear cell tumors (FIG. 20D) and a secreted product was most noticeable in endometrioid tumors (FIG. 20E).

TABLE 5

Patient Characteristics and Expression of PUMP-1 Gene

| Case | Histological type[a] | Stage/Grade | LN[b] | mRNA expression of PUMP-1[c] |
|---|---|---|---|---|
| 1 | normal ovary | | | n |
| 2 | normal ovary | | | n |
| 3 | normal ovary | | | n |
| 4 | normal ovary | | | n |
| 5 | normal ovary | | | n |
| 6 | normal ovary | | | n |
| 7 | normal ovary | | | n |
| 8 | normal ovary | | | n |
| 9 | normal ovary | | | n |
| 10 | normal ovary | | | n |
| 11 | S adenoma (LMP) | 1/1 | N | 4+ |
| 12 | S adenoma (LMP) | 1/1 | NE | n |
| 13 | S adenoma (LMP) | 1/1 | NE | 4+ |
| 14 | S adenoma (LMP) | 1/1 | N | 4+ |
| 15 | S adenoma (LMP) | 3/1 | P | 4+ |
| 16 | S adenoma (LMP) | 3/1 | P | 4+ |
| 17 | S adenoma (LMP) | 3/1 | P | 4+ |
| 18 | M adenoma (LMP) | 1/1 | NE | n |
| 19 | M adenoma (LMP) | 1/1 | N | n |
| 20 | M adenoma (LMP) | 1/1 | N | 4+ |
| 21 | M adenoma (LMP) | 1/1 | NE | 4+ |
| 22 | M adenoma (LMP) | 1/1 | NE | 4+ |
| 23 | S carcinoma | 1/2 | N | 4+ |
| 24 | S carcinoma | 1/3 | N | 4+ |
| 25 | S carcinoma | 3/1 | NE | 4+ |
| 26 | S carcinoma | 3/2 | NE | 4+ |
| 27 | S carcinoma | 3/2 | P | 4+ |
| 28 | S carcinoma | 3/2 | NE | 2+ |
| 29 | S carcinoma | 3/3 | NE | n |
| 30 | S carcinoma | 3/3 | NE | 4+ |
| 31 | S carcinoma | 3/3 | NE | 4+ |
| 32 | S carcinoma | 3/3 | NE | 4+ |
| 33 | S carcinoma | 3/3 | N | 2+ |
| 34 | S carcinoma | 3/3 | NE | n |
| 35 | S carcinoma | 3/3 | NE | 4+ |
| 36 | S carcinoma | 3/3 | NE | 4+ |
| 37 | S carcinoma | 3/3 | NE | 2+ |
| 38 | S carcinoma | 3/3 | N | n |
| 39 | S carcinoma | 3/2 | NE | 4+ |
| 40 | S carcinoma | 3/3 | NE | 2+ |
| 41 | S carcinoma | 3/2 | NE | n |
| 42 | M carcinoma | 1/2 | N | 4+ |
| 43 | M carcinoma | 2/2 | NE | 4+ |
| 44 | M carcinoma | 2/2 | N | 4+ |
| 45 | M carcinoma | 3/1 | NE | 4+ |
| 46 | M carcinoma | 3/2 | NE | n |
| 47 | M carcinoma | 3/2 | NE | n |
| 48 | M carcinoma | 3/3 | NE | 4+ |
| 49 | E carcinoma | 2/3 | N | 4+ |
| 50 | E carcinoma | 3/2 | NE | 4+ |
| 51 | E carcinoma | 3/3 | NE | 4+ |
| 52 | C carcinoma | 1/3 | N | 4+ |
| 53 | C carcinoma | 1/1 | N | 4+ |
| 54 | C carcinoma | 3/2 | P | 4+ |

[a]S, serous; M, mucinous; E, endometrioid; C, clear cell;
[b]LN, lymph node metastasis; P, positive; N, negative; NE, not examined;
[c]n, normal range = mean ±2SD; 2+, mean +2SD to +4SD; 4+, mean +4SD or greater.

TABLE 6

Overexpression of PUMP-1 in normal ovaries and ovarian tumors

| Type | N | PUMP-1 Overexpression | Ratio of PUMP-1 to β-tubulin |
|---|---|---|---|
| Normal | 10 | 0 (0%) | 0.084 ± 0.065 |
| LMP | 12 | 9 (75.0%) | 0.905 ± 1.251 |
| Serous | 7 | 6 (85.7%) | 1.301 ± 1.542 |
| Mucinous | 5 | 3 (60.0%) | 0.351 ± 0.269 |
| Carcinomous | 32 | 26 (81.3%) | 0.663 ± 0.630 |
| Serous | 19 | 15 (78.9%) | 0.675 ± 0.774 |
| Mucinous | 7 | 5 (71.4%) | 0.474 ± 0.337 |
| Endometrioid | 3 | 3 (100%) | 0.635 ± 0.224 |
| Clear Cell | 3 | 3 (100%) | 1.062 ± 0.060 |

TABLE 7

Expression of PUMP-1 protein by immunolocalization

| Histology | mRNA[a] | Protein[b] |
|---|---|---|
| Normal ovary | n | − |
| S Carcinoma | 4+ | + |
| S Carcinoma | 4+ | + |
| S Carcinoma | 4+ | + |
| S Carcinoma | 4+ | + |
| S Carcinoma | 2+ | + |
| S Carcinoma | n | − |
| S Carcinoma | 4+ | + |
| S Carcinoma | 2+ | + |
| S Carcinoma | n | − |
| M Carcinoma | n | − |
| C Carcinoma | 4+ | + |
| C Carcinoma | 4+ | + |
| C Carcinoma | 4+ | + |

[a]mRNA expression of PUMP-1 (see Table 5). n = low or no transcript detected by quantitative PCR. 2+/4+ = overexpression of PUMP-1 transcription by more than 2SD or 4SD over the normal level of PUMP-1 in normal ovary.
[b]+, >10% positive tumor cells; −, negative.

EXAMPLE 8
Summary of Proteases Detected Herein

Most of the proteases described herein were identified from the sense-His/antisense-Ser primer pair, yielding a 500 bp PCR product (FIG. 1, lane 4). Some of the enzymes are familiar, a short summary of each follows.

Hepsin

Hepsin is a trypsin-like serine protease cloned from hepatoma cells. Hepsin is an extracellular protease (the enzyme includes a secretion signal sequence) which is anchored in the plasma membrane by its amino terminal domain, thereby exposing its catalytic domain to the extracellular matrix. Hepsin has also been shown to be expressed in breast cancer cell lines and peripheral nerve cells. It has never before been associated with ovarian carcinoma. Specific primers for the hepsin gene were synthesized and the expression of hepsin examined using Northern blots of fetal tissue and ovarian tissue (both normal and ovarian carcinoma).

Figures 10A, 10B, 10C:
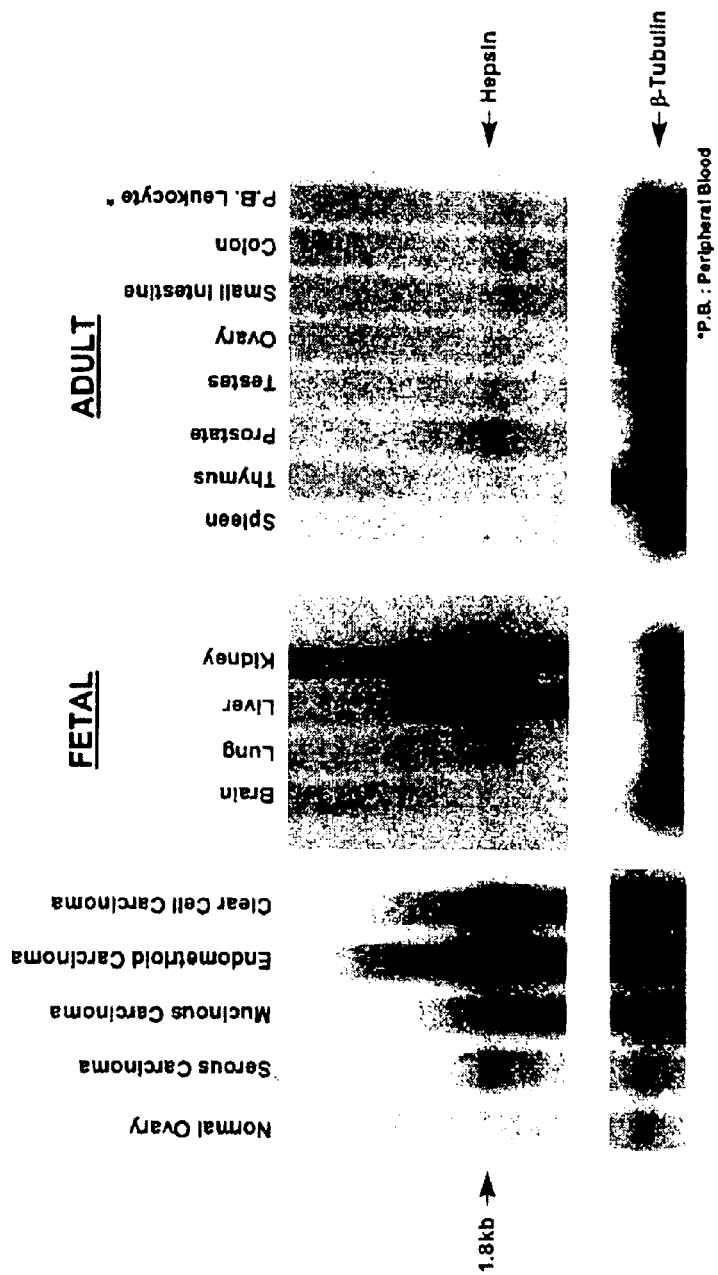
(FIG. 10A), lane 1, normal ovary (case 10); lane 2, serous carcinoma (case 35); lane 3, mucinous carcinoma (case 48); lane 4, endometrioid carcinoma (case 51); and lane 5, clear cell carcinoma (case 54). In cases 35, 51 and 54, more than a 10-fold increase in the hepsin 1.8 kb transcript abundance was observed. Northern blot analysis of hepsin in normal human fetal (FIG. 10B) and adult tissues (FIG. 10C). Significant overexpression of the hepsin transcript is noted in both fetal liver and fetal kidney. Notably, hepsin overexpression is not observed in normal adult tissue. Slight expression above the background level is observed in the adult prostate.

FIG. 10A shows that hepsin was expressed in fetal liver and fetal kidney as anticipated, but at very low levels or not at all in fetal brain and lung. FIG. 10B shows that hepsin was expressed in ovarian carcinomas of different histologic types, but not in normal ovary. The mRNA identified in both Northern blots was the appropriate size for the hepsin transcript. The expression of hepsin was examined in 10 normal ovaries and 44 ovarian tumors using specific primers to β-tubulin and hepsin in a quantitative PCR assay, and found it to be linear over 35 cycles. Expression is presented as the ratio of $^{32}$P-hepsin band to the internal control, the $^{32}$P-β-tubulin band.

Figure 11A:
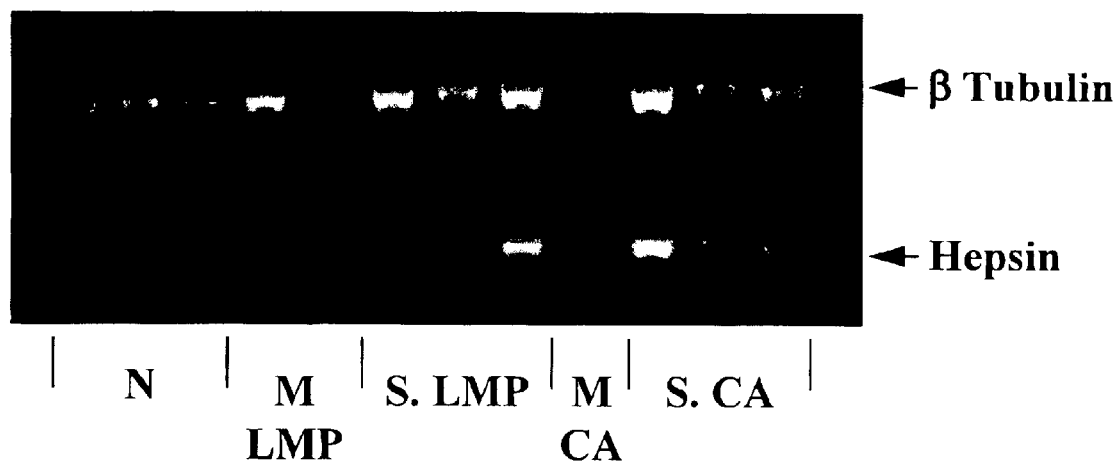
FIG. 11A shows quantitative PCR of hepsin and internal control β-tubulin.
Figure 11B:
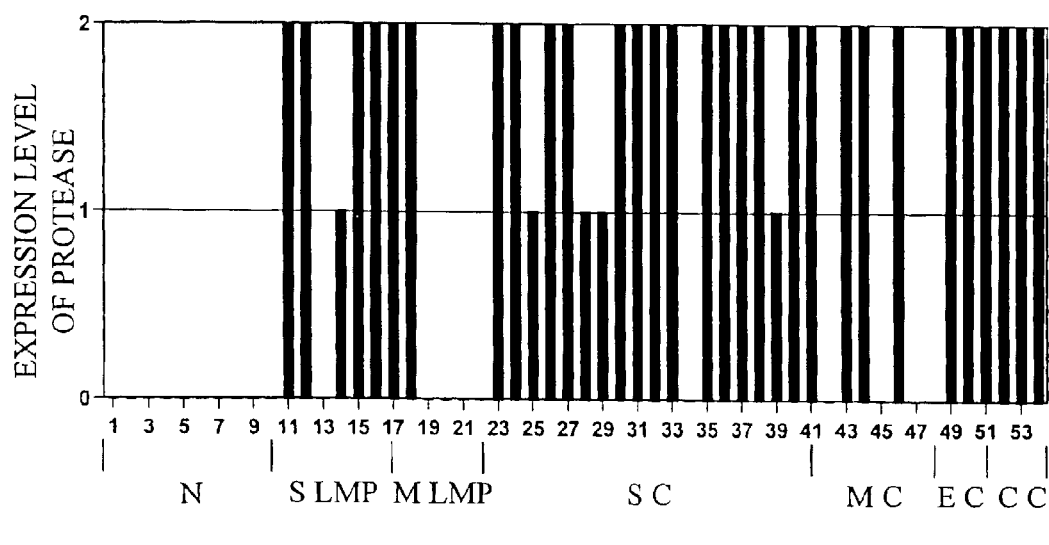
FIG. 11B shows a bar graph of expression of hepsin in 10 normal ovaries and 44 ovarian carcinoma samples.

FIGS. 11A & 11B show hepsin expression in normal (N), mucinous (M) and serous (S) low malignant potential (LMP)

tumors and carcinomas (CA). FIG. 11A shows quantitative PCR of hepsin and internal control β-tubulin. FIG. 11B shows a bar graph of expression of PUMP-1 in 10 normal ovaries and 44 ovarian carcinoma samples.

Hepsin mRNA is highly overexpressed in most histopathologic types of ovarian carcinomas including some low malignant potential tumors (see FIGS. 11A & 11B). Most noticeably, hepsin is highly expressed in serous, endometrioid and clear cell tumors tested. It is highly expressed in some mucinous tumors, but it is not overexpressed in the majority of such tumors.

Stratum Corneum Chymotrypsin Enzyme (SCCE)

The PCR product identified was the catalytic domain of the sense-His/antisense-Ser of the SCCE enzyme. This extracellular protease was cloned, sequenced and shown to be expressed on the surface of keratinocytes in the epidermis. SCCE is a chymotrypsin-like serine protease whose function is suggested to be in the catalytic degradation of intercellular cohesive structures in the stratum corneum layer of the skin. This degradation allows continuous shedding (desquamation) of cells from the skin surface. The subcellular localization of SCCE is in the upper granular layer in the stratum corneum of normal non-palmoplantar skin and in the cohesive parts of hypertrophic plantar stratum corneum. SCCE is exclusively associated with the stratum corneum and has not so far been shown to be expressed in any carcinomatous tissues.

Figure 12A:
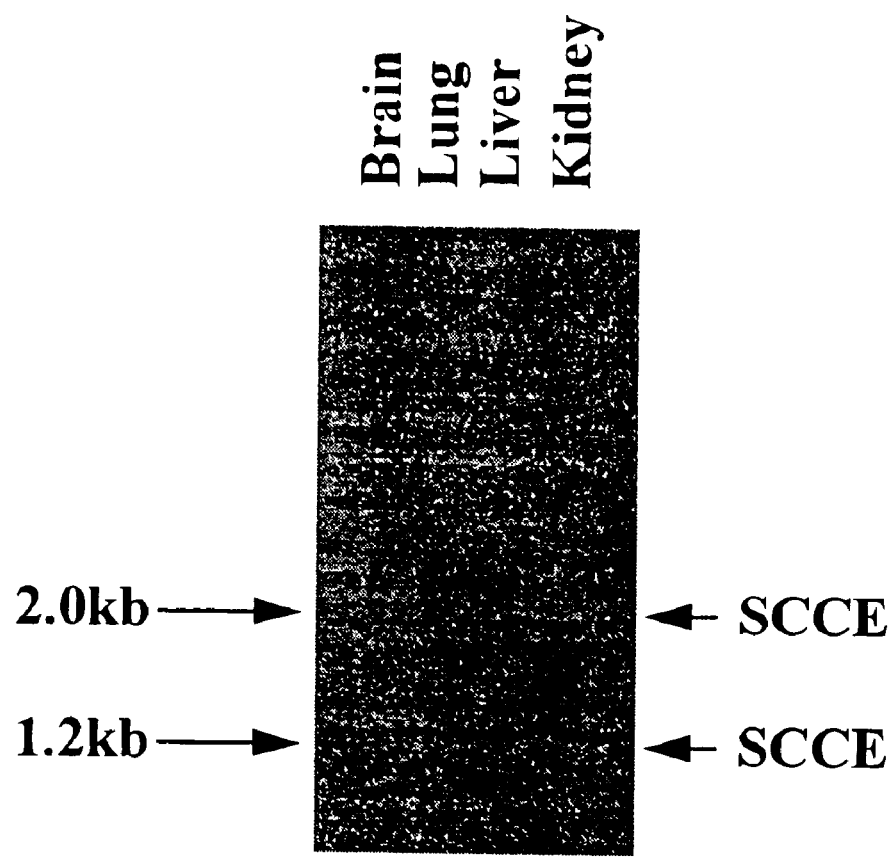
FIG. 12 shows northern blot analysis of mRNA expression of the SCCE gene in fetal tissue (FIG. 12A) and in ovarian tissue (FIG. 12B).
Figure 12B:
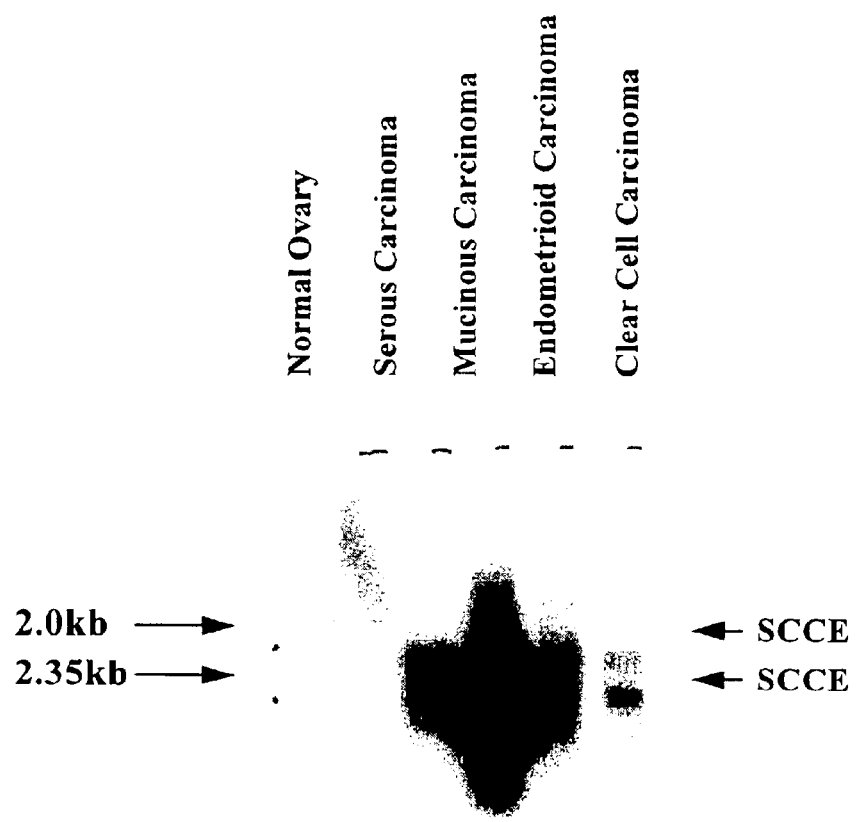

Northern blots were probed with the PCR product to determine expression of SCCE in fetal tissue and ovarian carcinoma (FIGS. 12A & 12B). Noticeably, detection of SCCE messenger RNA on the fetal Northern was almost non-existent (a problem with the probe or the blot was excluded by performing the proper controls). A faint band appeared in fetal kidney. On the other hand, SCCE mRNA is abundant in the ovarian carcinoma mRNA (FIG. 12B). Two transcripts of the correct size are observed for SCCE. The same panel of cDNA used for hepsin analysis was used for SCCE expression.

No SCCE expression was detected in the normal ovary lane of the Northern blot. A comparison of all candidate genes, including a loading marker (β-tubulin), was shown to confirm that this observation was not a result of a loading bias. Quantitative PCR using SCCE primers, along with β-tubulin internal control primers, confirmed the overexpression of SCCE mRNA in carcinoma of the ovary with no expression in normal ovarian tissue (FIG. 13).

Figure 13A:
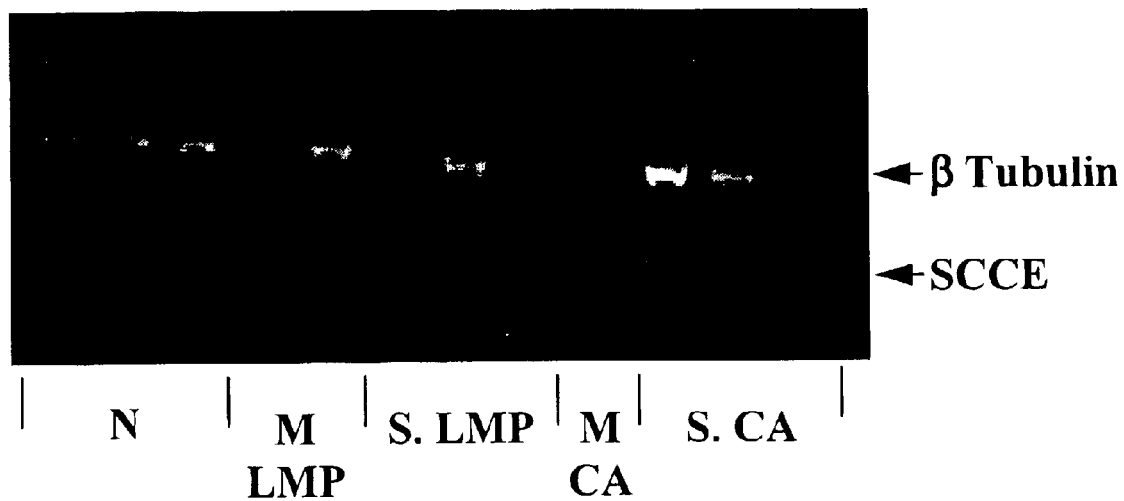
FIG. 13A shows a comparison of quantitative PCR of cDNA from normal ovary and ovarian carcinomas.
Figure 13B:
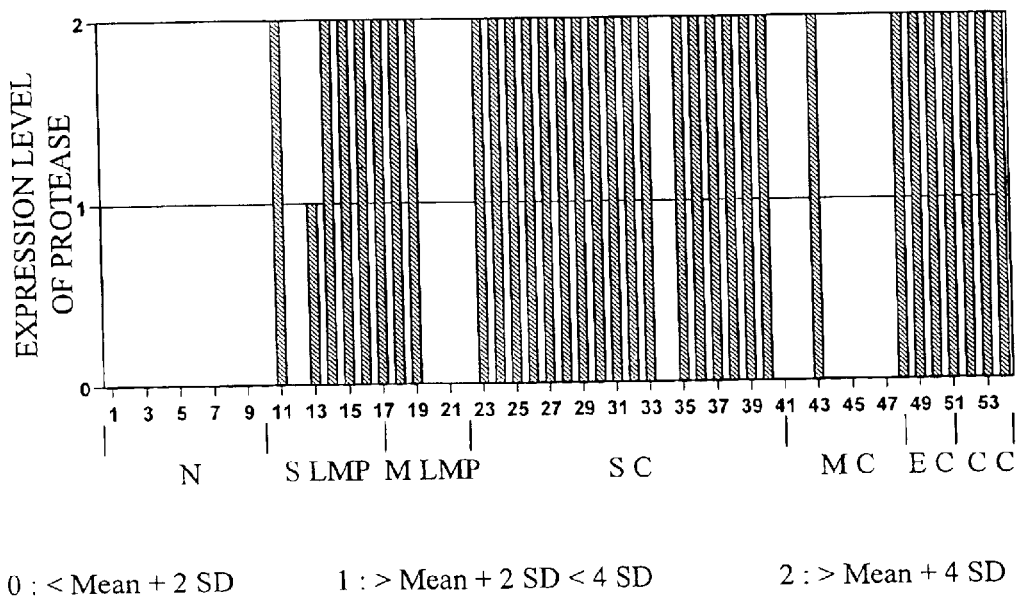
FIG. 13B shows a bar graph comparing the ratio of SCCE to β-tubulin in 10 normal and 44 ovarian carcinoma tissues.

FIG. 13A shows a comparison using quantitative PCR of SCCE cDNA from normal ovary and ovarian carcinomas. FIG. 13B shows the ratio of SCCE to the β-tubulin internal standard in 10 normal and 44 ovarian carcinoma tissues. Again, it is observed that SCCE is highly overexpressed in ovarian carcinoma cells. It is also noted that some mucinous tumors overexpress SCCE, but the majority do not.

Protease M

Figure 14:
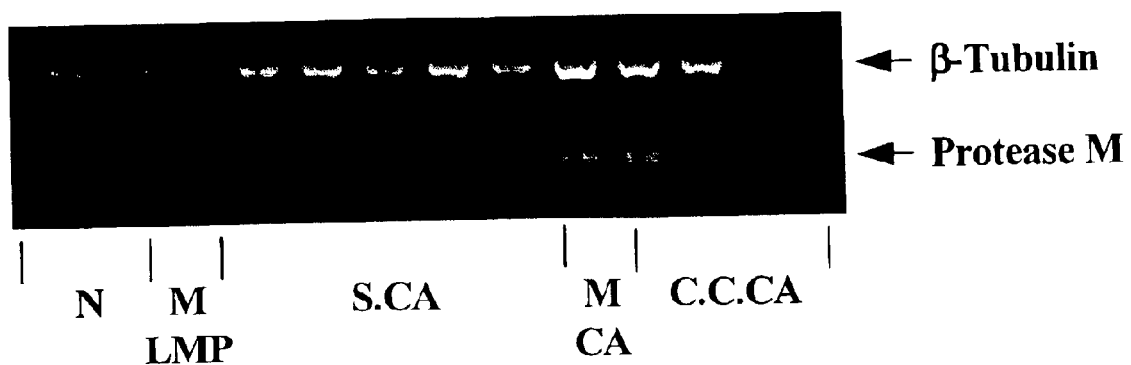
FIG. 14 shows a comparison by quantitative PCR of normal and ovarian carcinoma expression of mRNA for protease M.

Protease M was identified from subclones of the His--ser primer pair. This protease was first cloned by Anisowicz, et al., [*Molecular Medicine,* 2, 624–636 (1996)] and shown to be overexpressed in breast and ovarian carcinomas. A preliminary evaluation indicates that this enzyme is overexpressed in ovarian carcinoma (FIG. 14).

Cofactor I and Complement Factor B

Several serine proteases associated with the coagulation pathway were also subcloned. Examination of normal and ovarian carcinomas by quantitative PCR for expression of these enzymes, it was noticeable that this mRNA was not clearly overexpressed in ovarian carcinomas when compared to normal ovarian tissue. It should be noted that the same panel of tumors was used for the evaluation of each candidate protease.

TADG-12

TADG-12 was identified from the primer pairs, sense-His/antisense-Asp (see FIG. 1, lanes 1 & 2). Upon subcloning both PCR products in lane 2, the 200 bp product had a unique protease-like sequence not included in GenBank. This 200 bp product contains many of the conserved amino acids common for the His-Asp domain of the family of serine proteins. The second and larger PCR product (300 bp) was shown to have a high degree of homology with TADG-12 (His-Asp sequence), but also contained approximately 100 bp of unique sequence. Synthesis of specific primers and the sequencing of the subsequent PCR products from three different tumors demonstrated that the larger PCR product (present in about 50% of ovarian carcinomas) includes an insert of about 100 bp near the 5' end (and near the histidine) of the sequence. This insert may be a retained genomic intron because of the appropriate position of splice sites and the fact that the insert does not contain an open reading frame (see FIG. 15). This suggests the possibility of a splice site mutation which gives rise to retention of the intron, or a translocation of a sequence into the TADG-12 gene in as many as half of all ovarian carcinomas.

TADG-13 and TADG-14

Figure 16A:
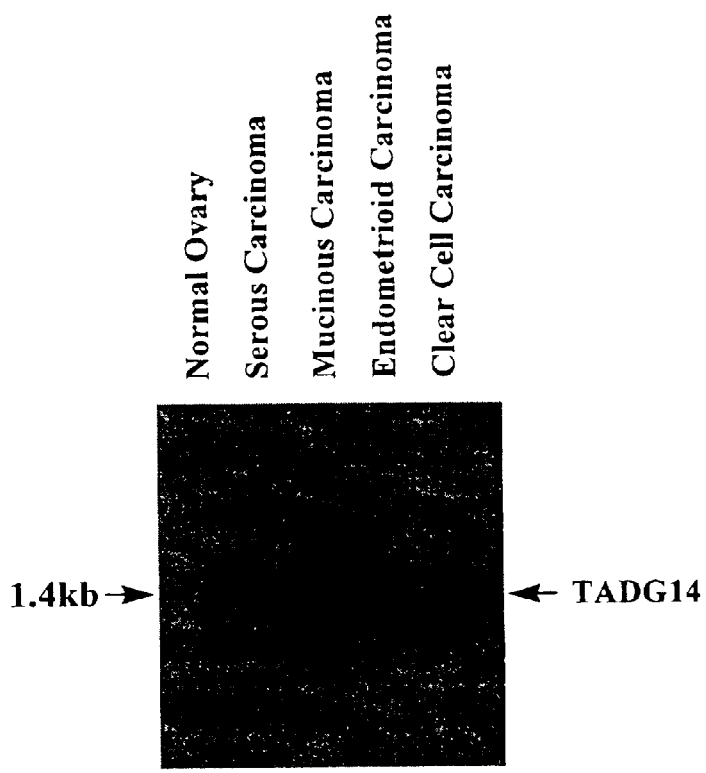
FIG. 16 shows northern blot analysis comparing TADG-14 expression in normal and ovarian carcinoma tissues (FIG. 16A), and preliminary quantitative PCR amplification of normal and carcinoma cDNAs using specific primers for TADG-14 (FIG. 16B).
Figure 16B:
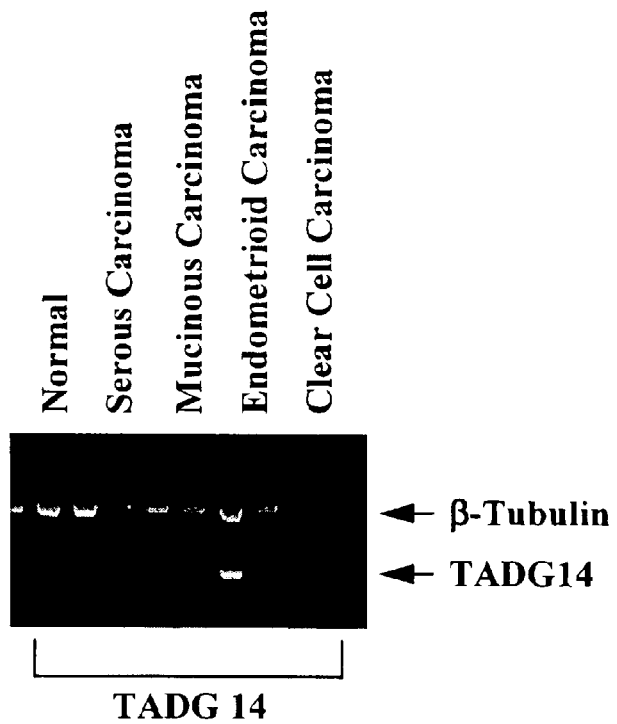

Specific primers were synthesized for TADG-13 and TADG-14 to evaluate expression of genes in normal and ovarian carcinoma tissue. Northern blot analysis of ovarian tissues indicates the transcript for the TADG-14 gene is approximately 1.4 kb and is expressed in ovarian carcinoma tissues (FIG. 16A) with no noticeable transcript presence in normal tissue. In quantitative PCR studies using specific primers, increased expression of TADG-14 in ovarian carcinoma tissues was noted compared to a normal ovary (FIG. 16B). The presence of a specific PCR product for TADG-14 in both an HeLa library and an ovarian carcinoma library was also confirmed. Several candidate sequences corresponding to TADG-14 have been screened and isolated from the HeLa library.

Clearly from sequence homology, these genes fit into the family of serine proteases. TADG-13 and -14 are, however, heretofore undocumented genes which the specific primers of the invention allow to be evaluated in normal and tumor cells, and with which the presence or absence of expression of these genes is useful in the diagnosis or treatment selection for specific tumor types.

Cathepsin-L

Figure 21:
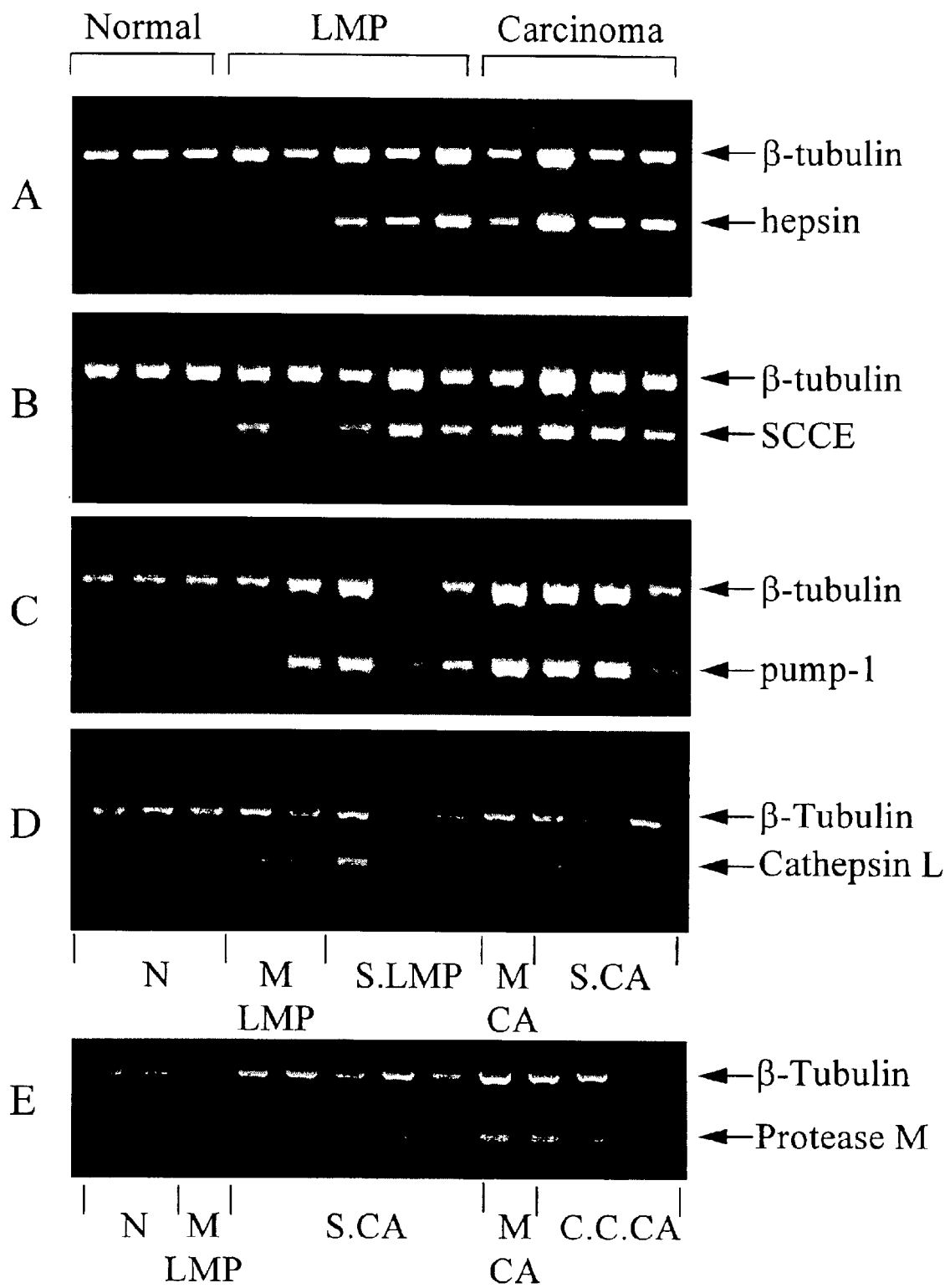
FIG. 21 shows a comparison of PCR amplified products for the hepsin, SCCE, protease M, PUMP-1 and Cathepsin L genes.

Using redundant cysteine protease primers to conserved domains surrounding individual cysteine and histidine residues, the cathepsin-L protease was identified in several serous carcinomas. An initial examination of the expression of cathepsin L in normal and ovarian tumor tissue indicates that transcripts for the cathepsin-L protease are present in both normal and tumor tissues (FIG. 21). However, its presence or absence in combination with other proteases of the present invention permits identification of specific tumor types and treatment choices.

EXAMPLE 9

Summary of Data

Redundant primers to conserved domains of serine, metallo-, and cysteine proteases have yielded a set of genes whose mRNAs are overexpressed in ovarian carcinoma. The genes which are clearly overexpressed include the serine proteases hepsin, SCCE, protease M TADG12, TADG14 and the metallo-protease PUMP-1 (see FIG. 21 and Table 8). Northern blot analysis of normal and ovarian carcinoma tissues, summarized in FIG. 14, indicated overexpression of hepsin, SCCE, PUMP-1 and TADG-14. A β-tubulin probe to control for loading levels was included.

For the most part, these proteins previously have not been associated with the extracellular matrix of ovarian carcinoma cells. No panel of proteases which might contribute to the growth, shedding, invasion and colony development of metastatic carcinoma has been previously described, including the three new candidate serine proteases which are herein disclosed. The establishment of an extracellular protease panel associated with either malignant growth or malignant potential offers the opportunity for the identification of diagnostic or prognostic markers and for therapeutic intervention through inhibition or down regulation of these proteases.

The availability of the instant gene-specific primers coding for the appropriate region of tumor specific proteases allows for the amplification of a specific cDNA probe using Northern and Southern analysis, and their use as markers to detect the presence of the cancer in tissue. The probes also allow more extensive evaluation of the expression of the gene in normal ovary versus low malignant potential tumor, as well as both high- and low-stage carcinomas. The evaluation of a panel of fresh frozen tissue from all the carcinoma subtypes (Table 4) allowed the determination of whether a protease is expressed predominantly in early stage disease or within specific carcinoma subtypes. It was also determined whether each genes' expression is confined to a particular stage in tumor progression and/or is associated with metastatic lesions. Detection of specific combinations of proteases is an identifying characteristic of the specific tumor types and yields valuable information for diagnoses and treatment selection. Particular tumor types may be more accurately diagnosed by the characteristic expression pattern of each specific tumor.

life indicates a stronger association with that peptide and the particular HLA molecule. The PUMP-1 peptides that strongly bind to an HLA allele are putative immunogens, and are used to innoculate an individual against PUMP-1.

TABLE 9

PUMP-1 peptide ranking

| HLA Type & Ranking | Start | Peptide | Predicted Dissociation$_{1/2}$ | SEQ ID No. |
|---|---|---|---|---|
| HLA A0201 | | | | |
| 1 | 208 | FLYAATHEL | 314.455 | 30 |
| 2 | 134 | NMWGKEIPL | 128.056 | 31 |
| 3 | 81 | IMQKPRCGV | 85.394 | 32 |
| 4 | 10 | CLLPGSLAL | 79.041 | 33 |
| 5 | 60 | KEMQKFFGL | 59.278 | 34 |
| 6 | 203 | SLGINFLYA | 51.916 | 35 |
| 7 | 73 | MLNSRVIEI | 40.792 | 36 |
| 8 | 4 | TVLCAVCLL | 15.907 | 37 |
| 9 | 132 | ALNMWGKEI | 10.433 | 38 |
| 10 | 109 | VTYRIVSYT | 7.122 | 39 |
| 11 | 127 | RLVSKALNM | 4.968 | 40 |
| 12 | 154 | IMIGFARGA | 4.636 | 41 |
| 13 | 43 | YLYDSETKN | 4.497 | 42 |
| 14 | 140 | IPLHFRKVV | 4.449 | 43 |
| 15 | 146 | KVVWGTADI | 3.195 | 44 |
| 16 | 36 | QDYLKRFYL | 3.029 | 45 |
| 17 | 2 | RLTVLCAVC | 2.037 | 46 |
| 18 | 201 | GSSLGINFL | 1.764 | 47 |
| 19 | 70 | ITGMLNSRV | 1.642 | 48 |
| 20 | 205 | GINFLYAAT | 1.537 | 49 |
| HLA A0205 | | | | |
| 1 | 4 | TVLCAVCLL | 84.000 | 50 |
| 2 | 208 | FLYAATHEL | 63.000 | 51 |

TABLE 8

Overexpression of proteases in ovarian tumors

| Type | N | PUMP-1 | SCCE | Pump-1 | Prot M |
|---|---|---|---|---|---|
| Normal | 10 | 0% (0/10) | 0% (0/10) | 0% (0/10) | 0% (0/10) |
| LMP | 12 | 58.3% (7/12) | 66.7% (8/12) | 75.0% (9/12) | 75% (9/12) |
| Serous | 7 | 85.7% (6/7) | 85.7% (6/7) | 85.7% (6/7) | 100% (7/7) |
| mucinous | 5 | 20.0% (1/5) | 40.0% (2/5) | 60% (3/5) | 40.0% (2/5) |
| Carcinoma | 32 | 84.4% (27/32) | 78.1% (25/32) | 81.3% (26/32) | 90.6% (29/32) |
| serous | 19 | 94.7% (18/19) | 89.5% (17/19) | 78.9% (15/19) | 94.7% (18/19) |
| mucinous | 7 | 42.9% (3/7) | 28.6% (2/7) | 71.4% (5/7) | 85.7% (6/7) |
| endometr. | 3 | 100% (3/3) | 100% (3/3) | 100% (3/3) | 100% (3/3) |
| clear cell | 3 | 100% (3/3) | 100% (3/3) | 100% (3/3) | 67.7% (2/3) |

EXAMPLE 10

Antisense PUMP-1

PUMP-1 is cloned and expressed in the opposite orientation such that an antisense RNA molecule (SEQ ID No. 28) is produced. For example, the antisense RNA is used to hybridize to the complementary RNA in the cell and thereby inhibit translation of PUMP-1 RNA into protein.

EXAMPLE 11

Peptide Ranking

For vaccine or immune stimulation, individual 9-mers to 11-mers of the PUMP-1 protein were examined to rank the binding of individual peptides to the top 8 haplotypes in the general population (Parker et al., (1994)). The computer program used for this analyses can be found at <http://www-bimas.dcrt.nih.gov/molbio/hla_bind/>. Table 9 shows the peptide ranking based upon the predicted half-life of each peptide's binding to a particular HLA allele. A larger half- TABLE 9-continued PUMP-1 peptide ranking

| HLA Type & Ranking | Start | Peptide | Predicted Dissociation$_{1/2}$ | SEQ ID No. |
|---|---|---|---|---|
| 3 | 60 | KEMQKFFGL | 21.168 | 52 |
| 4 | 10 | CLLPGSLAL | 21.000 | 53 |
| 5 | 134 | NMWGKEIPL | 21.000 | 54 |
| 6 | 8 | AVCLLPGSL | 14.000 | 55 |
| 7 | 146 | KVVWGTADI | 6.000 | 56 |
| 8 | 73 | MLNSRVIEI | 3.400 | 57 |
| 9 | 81 | IMQKPRCGV | 3.400 | 58 |
| 10 | 66 | FGLPITGML | 3.150 | 59 |
| 11 | 147 | VVWGTADIM | 2.550 | 60 |
| 12 | 212 | ATHELGHSL | 2.100 | 61 |

TABLE 9-continued

PUMP-1 peptide ranking

| HLA Type & Ranking | Start | Peptide | Predicted Dissociation$_{1/2}$ | SEQ ID No. |
|---|---|---|---|---|
| 13 | 178 | HAFAPGTGL | 2.100 | 62 |
| 14 | 205 | GINFLYAAT | 2.000 | 63 |
| 15 | 22 | QEAGGMSEL | 1.960 | 64 |
| 16 | 112 | RIVSYTRDL | 1.680 | 65 |
| 17 | 167 | YPFDGPGNT | 1.350 | 66 |
| 18 | 3 | LTVLCAVCL | 1.190 | 67 |
| 19 | 140 | IPLHFRKVV | 1.020 | 68 |
| 20 | 109 | VTYRIVSYT | 1.020 | 69 |
| HLA A1 | | | | |
| 1 | 225 | SSDPNAVMY | 750.000 | 70 |
| 2 | 78 | VIEIMQKPR | 9.000 | 71 |
| 3 | 198 | WTDGSSLGI | 6.250 | 72 |
| 4 | 238 | NGDPQNFKL | 6.250 | 73 |
| 5 | 92 | VAEYSLFPN | 4.500 | 74 |
| 6 | 35 | AQDYLKRFY | 3.750 | 75 |
| 7 | 202 | SSLGINFLY | 3.750 | 76 |
| 8 | 46 | DSETKNANS | 2.700 | 77 |
| 9 | 87 | CGVPDVAEY | 2.500 | 78 |
| 10 | 248 | QDDIKGIQK | 2.500 | 79 |
| 11 | 27 | MSELQWEQA | 1.350 | 80 |
| 12 | 150 | GTADIMIGF | 1.250 | 81 |
| 13 | 123 | ITVDRLVSK | 1.000 | 82 |
| 14 | 108 | VVTYRIVSY | 1.000 | 83 |
| 15 | 54 | SLEAKLKEM | 0.900 | 84 |
| 16 | 163 | HGDSYPFDG | 0.625 | 85 |
| 17 | 10 | CLLPGSLAL | 0.500 | 86 |
| 18 | 151 | TADIMIGFA | 0.500 | 87 |
| 19 | 138 | KEIPLHFRK | 0.500 | 88 |
| 20 | 137 | GKEIPLHFR | 0.450 | 89 |
| HLA A24 | | | | |
| 1 | 115 | SYTRDLPHI | 50.000 | 90 |
| 2 | 112 | RIVSYTRDL | 12.000 | 91 |
| 3 | 66 | FGLPITGML | 10.080 | 92 |
| 4 | 37 | DYLKRFYLY | 9.000 | 93 |
| 5 | 51 | NANSLEAKL | 7.920 | 94 |
| 6 | 166 | SYPFKGPGN | 7.500 | 95 |
| 7 | 10 | CLLPGSLAL | 7.200 | 96 |
| 8 | 4 | TVLCAVCLL | 6.000 | 97 |
| 9 | 31 | QWEQAQDYL | 6.000 | 98 |
| 10 | 3 | LTVLCAVCL | 6.000 | 99 |
| 11 | 212 | ATHELGHSL | 5.760 | 100 |
| 12 | 238 | NGDPQNFKL | 5.280 | 101 |
| 13 | 44 | LYDSETKNA | 5.000 | 102 |
| 14 | 235 | TYGNGDPQN | 5.000 | 103 |
| 15 | 243 | NFKLSQDDI | 5.000 | 104 |
| 16 | 8 | AVCLLPGSL | 4.800 | 105 |
| 17 | 12 | LPGSLALPL | 4.800 | 106 |
| 18 | 58 | KLKEMQKFF | 4.800 | 107 |
| 19 | 201 | GSSLGINFL | 4.800 | 108 |
| 20 | 208 | FLYAATHEL | 4.400 | 109 |
| HLA B7 | | | | |
| 1 | 120 | LPHITVDRL | 80.000 | 110 |
| 2 | 12 | LPGSLALPL | 80.000 | 111 |
| 3 | 8 | AVCLLPGSL | 60.000 | 112 |
| 4 | 84 | KPRCGVPDV | 40.000 | 113 |
| 5 | 89 | VPDVAEYSL | 24.000 | 114 |
| 6 | 4 | TVLCAVCLL | 20.000 | 115 |
| 7 | 178 | HAFAPGTGL | 18.000 | 116 |
| 8 | 51 | NANSLEAKL | 12.000 | 117 |
| 9 | 212 | ATHELGHSL | 12.000 | 118 |
| 10 | 140 | IPLHFRKVV | 6.000 | 119 |
| 11 | 147 | VVWGTADIM | 5.000 | 120 |
| 12 | 208 | FLYAATHEL | 4.000 | 121 |
| 13 | 101 | SPKWTSKVV | 4.000 | 122 |
| 14 | 10 | CLLPGSLAL | 4.000 | 123 |
| 15 | 3 | LTVLCAVCL | 4.000 | 124 |
| 16 | 201 | GSSLGINFL | 4.000 | 125 |
| 17 | 134 | NMWGKEIPL | 4.000 | 126 |
| 18 | 112 | RIVSYTRDL | 4.000 | 127 |
| 19 | 125 | VDRLVSKAL | 4.000 | 128 |
| 20 | 66 | FGLPITGML | 4.000 | 129 |
| HLA B8 | | | | |
| 1 | 134 | NMWGKEIPL | 4.000 | 130 |
| 2 | 56 | EAKLKEMQK | 3.200 | 131 |
| 3 | 101 | SPKWTSKVV | 2.400 | 132 |
| 4 | 73 | MLNSRVIEI | 2.000 | 133 |
| 5 | 84 | KPRCGVPDV | 1.200 | 134 |
| 6 | 127 | RLVSKALNM | 1.000 | 135 |
| 7 | 105 | TSKVVTYRI | 1.000 | 136 |
| 8 | 51 | NANSLEAKL | 0.800 | 137 |
| 9 | 12 | LPGSLALPL | 0.800 | 138 |
| 10 | 120 | LPHITVDRL | 0.800 | 139 |
| 11 | 178 | HAFAPGTGL | 0.800 | 140 |
| 12 | 54 | SLEAKLKEM | 0.400 | 141 |
| 13 | 10 | CLLPGSLAL | 0.400 | 142 |
| 14 | 208 | FLYAATHEL | 0.400 | 143 |
| 15 | 125 | VDRLVSKAL | 0.400 | 144 |
| 16 | 158 | FARGAHGDS | 0.400 | 145 |
| 17 | 36 | QDYLKRFYL | 0.400 | 146 |
| 18 | 212 | ATHELGHSL | 0.300 | 147 |
| 19 | 116 | YTRDLPHIT | 0.300 | 148 |
| 20 | 62 | MQKFFGLPI | 0.300 | 149 |
| HLA B2702 | | | | |
| 1 | 159 | ATGAHGDSY | 200.000 | 150 |
| 2 | 30 | LQWEQAQDY | 100.00 | 151 |
| 3 | 196 | ERWTDGSSL | 90.000 | 152 |
| 4 | 40 | KRFYLDSE | 30.000 | 153 |
| 5 | 1 | MRLTVLCAV | 20.000 | 154 |
| 6 | 144 | FRKVVWGTA | 20.000 | 155 |
| 7 | 117 | TRDLPHITV | 20.000 | 156 |
| 8 | 134 | NMWGKEIPL | 7.500 | 157 |
| 9 | 96 | SLFPNSPKW | 7.500 | 158 |
| 10 | 62 | MQKFFGLPI | 6.000 | 159 |
| 11 | 35 | AQDYLKRFY | 6.000 | 160 |
| 12 | 208 | FLYAATHEL | 4.500 | 161 |
| 13 | 76 | SRVIEIMQK | 4.000 | 162 |
| 14 | 126 | DRLVSKALN | 3.000 | 163 |
| 15 | 60 | KEMQKFFGL | 2.700 | 164 |
| 16 | 58 | KLKEMQKFF | 2.700 | 165 |
| 17 | 256 | KLYGKRSNS | 2.250 | 166 |
| 18 | 85 | PRCGVPDVA | 2.000 | 167 |
| 19 | 111 | YRIVSYTRD | 2.000 | 168 |
| 20 | 178 | HAFAPGTGL | 1.500 | 169 |
| HLA B4403 | | | | |
| 1 | 87 | CGVPDVAEY | 36.000 | 170 |
| 2 | 202 | SSLGINFLY | 27.000 | 171 |
| 3 | 79 | IEIMQKPRC | 20.000 | 172 |
| 4 | 60 | KEMQKFFGL | 18.000 | 173 |
| 5 | 225 | SSDPNAVMY | 18.000 | 174 |
| 6 | 47 | SETKNANSL | 12.000 | 175 |
| 7 | 195 | DERWTDGSS | 12.000 | 176 |
| 8 | 214 | HELGHSLGM | 12.000 | 177 |
| 9 | 22 | QEAGGMSEL | 12.000 | 178 |
| 10 | 249 | DDIKGIQKL | 11.250 | 179 |
| 11 | 93 | AEYSLFPNS | 8.000 | 180 |
| 12 | 138 | KEIPLHFRK | 6.000 | 181 |
| 13 | 184 | TGLGGDAHF | 3.000 | 182 |
| 14 | 200 | DGSSLGINF | 3.000 | 183 |
| 15 | 35 | AQDYLKRFY | 3.000 | 184 |
| 16 | 34 | QAQDYLKRF | 2.250 | 185 |
| 17 | 30 | LQWEQAQDY | 2.250 | 186 |
| 18 | 250 | DIKGIQKLY | 2.025 | 187 |
| 19 | 150 | GTADIMIGF | 2.000 | 188 |
| 20 | 37 | DYLKRFYLY | 1.800 | 189 |

EXAMPLE 12

PUMP-1 Peptides as Target Epitopes for Human CD8+ Cytotoxic T Cells

Two computer programs were used to identify 9-mer peptides containing binding motifs for HLA class I molecules. The first, based on a scheme devised by Parker et at (1994), was developed by the Bioinformatics and Molecular Analysis Section (BIMAS) of the Center for Information Technology, NIH, and the second, known as SYFPEITHI, was formulated by Rammensee and colleagues at the University of Tubingen, Germany.

Peptides that possessed HLA A2.1 binding motifs were synthesized and tested directly for their ability to bind HLA A2. This technique employs T2 cells which are peptide transporter-deficient and thus express low endogenous HLA class I levels due to inability to load peptide and stabilize HLA class I folding for surface expression. It has been showed that addition of exogenous peptides capable of binding HLA A2.1 (A*0201) could increase the number of properly folded HLA A2.1 molecules on the cell surface, as revealed by flow cytometry (Nijman et al., 1993).

Peptides that possessed binding motifs for HLA class I molecules other than A2.1 can be tested directly for their ability to induce specific CD8+ CTL responses from normal adult donors as described below.

Monocyte-derived DC were generated from peripheral blood drawn from normal adult donors of the appropriate HLA type. Adherent monocytes were cultured in AIM-V (Gibco-BRL supplemented with GM-CSF and IL-4 according to standard techniques (Santin et al, 2000, 2001). After 5–6 days, DC maturation was induced by addition of $PGE_2$, IL-1β and TNFα for a further 48 h.

Mature DC were loaded with peptide ($2 \times 10^6$ DC with 50 µg/ml peptide in 1 ml serum-free AIM-V medium for 2 h at 37° C.) and washed once prior to culture with $1 \times 10^6$/ml peripheral blood mononuclear cells (PBMC) in AIM-V or AIM-V plus 5% human AB serum. The PBMC:DC ratio was between 20:1 and 30:1. After 7 days, responder T cells were restimulated with peptide-loaded, irradiated autologous DC or PBMC at responder:stimulator ratios between 10:1 and 20:1 or 1:1 and 1:10 respectively. At this point, cultures were supplemented with recombinant human IL-2 (10–100 U/ml), and fed with 50–75% changes of fresh medium plus IL-2 every 2–4 days. T cell lines were established and maintained by peptide restimulation every 14–21 days. Responder CD8+ T cells were purified by positive selection with anti-CD8-coupled magnetic beads (Dynal, Inc.) after the $2^{nd}$ or $3^{rd}$ antigen stimulation.

Peptide-specific cytotoxicity was tested in standard 5–6 h microwell $^{51}$Cr-release assays (Nazaruk et al, 1998). Autologous EBV-transformed lymphoblastoid cell lines (LCL) were loaded with peptide (50 µg/ml. 1 h at 37° C.) and subsequently $^{51}$Cr-labeled (50 µCi in 200–300 µl, 1 h at 37° C.). Peptide-loaded $^{51}$Cr-labeled LCL were incubated with CD8+ T cells at effector-target ration between 20:1 and 5:1. Cytotoxicity was recorded as percentage $^{51}$Cr released into culture supernatants.

PUMP-1 Peptide 208–216

Figure 22:
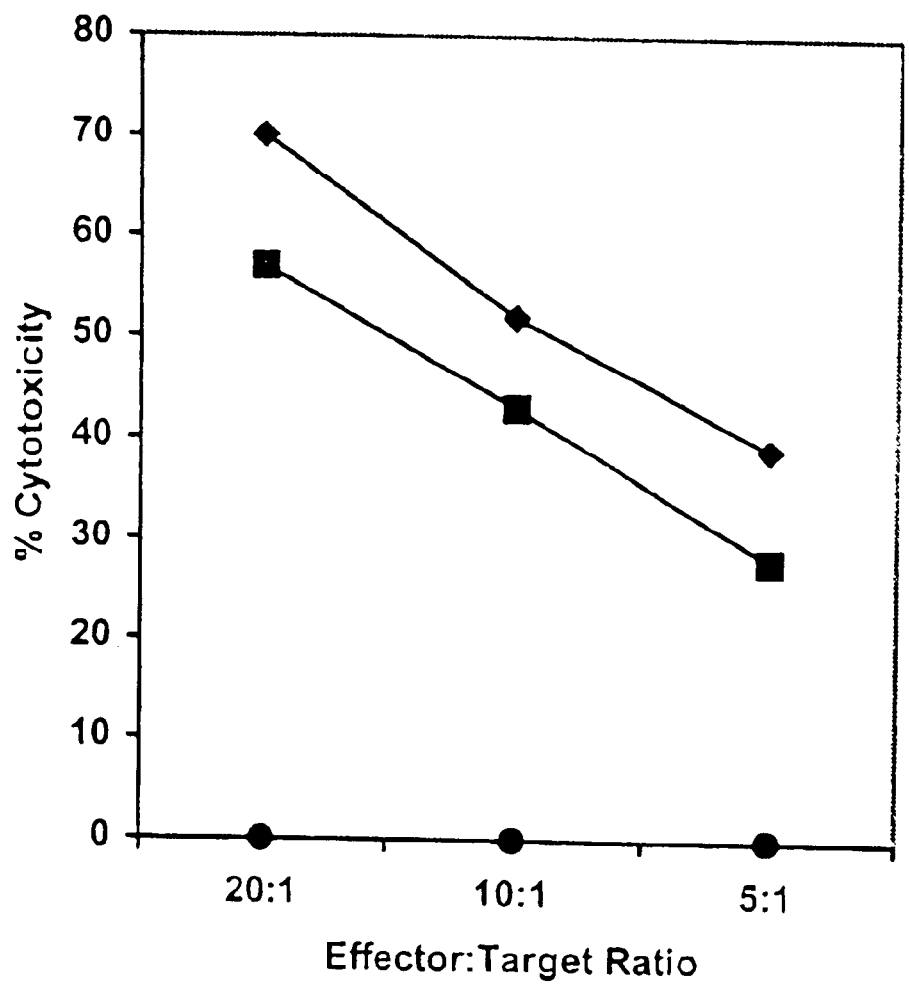
FIG. 22 shows CD8+ CTL recognition of PUMP-1 208–216 peptide in a 5 hr $^{51}$Cr release assay. Targets were autologous LCL (squares), allogeneic HLA A*0201-positive LCL (diamonds) or allogeneic HLA A*0201-negative LCL (circles) pulsed with 50 ug/ml of peptide. Control (i.e. unpulsed) LCL and K562 cells were not lysed.

PUMP-1 peptide 208–216 (SEQ ID No. 51) is an HLA A*0201-binding peptide, as revealed by upregulation of A*0201 expression in T2 cells (data not shown). CD8+ CTL specific for PUMP-1 208–216 killed peptide-loaded autologous LCL, but did not kill control, peptide-free LCL (FIG. 22). Heterologous HLA A*0201-expressing peptide-loaded LCL were efficiently killed, but targets lacking HLA A*0201 as well as natural killer-sensitive K562 cells were not killed.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An immunogenic composition, comprising a fragment of a matrix metalloprotease 7 protein encoded by nucleotide sequence SEQ ID NO: 29 and an appropriate adjuvant, wherein said fragment consist of 9 amino acids.

2. The immunogenic composition of claim 1, wherein said 9 amino acids long fragment is selected from the group consisting of SEQ ID Nos: 30, 31, 32, 33, 50, 51, 70, 110, 111, 150, 151 and 152.

* * * * *